US010722569B2

(12) United States Patent
Watnick

(10) Patent No.: US 10,722,569 B2
(45) Date of Patent: Jul. 28, 2020

(54) BACTERIAL BIOFILM MATRIX AS A PLATFORM FOR PROTEIN DELIVERY

(71) Applicant: Children's Medical Center Corporation, Boston, MA (US)

(72) Inventor: Paula I. Watnick, Waban, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/411,647

(22) PCT Filed: Jul. 3, 2013

(86) PCT No.: PCT/US2013/049337
§ 371 (c)(1),
(2) Date: Dec. 29, 2014

(87) PCT Pub. No.: WO2014/008406
PCT Pub. Date: Jan. 9, 2014

(65) Prior Publication Data
US 2015/0150959 A1    Jun. 4, 2015

Related U.S. Application Data

(60) Provisional application No. 61/780,079, filed on Mar. 13, 2013, provisional application No. 61/668,417, filed on Jul. 5, 2012.

(51) Int. Cl.
*A61K 39/02* (2006.01)
*A61K 47/69* (2017.01)
*A61K 38/47* (2006.01)
*A61K 39/00* (2006.01)

(52) U.S. Cl.
CPC ............ *A61K 39/107* (2013.01); *A61K 38/47* (2013.01); *A61K 39/02* (2013.01); *A61K 47/6901* (2017.08); *A61K 2039/52* (2013.01); *A61K 2039/55594* (2013.01); *A61K 2039/6006* (2013.01); *A61K 2039/6087* (2013.01); *A61K 2039/627* (2013.01); *C12Y 302/01014* (2013.01)

(58) Field of Classification Search
CPC ........ A61K 39/107; A61K 2039/55594; A61K 38/47; A61K 39/02; A61K 47/48776; A61K 2039/52; A61K 2039/6006; A61K 2039/6087; A61K 2039/627; C07K 14/28; C12Q 2600/158; C12Q 1/6837; C12Q 1/6876; C12Q 1/6883; C12Q 2600/142
See application file for complete search history.

(56) References Cited

U.S. PATENT DOCUMENTS

| | | | |
|---|---|---|---|
| 8,642,534 B2 | 2/2014 | Yildiz | |
| 2006/0235206 A1* | 10/2006 | Pier | C07K 14/1214 530/387.1 |
| 2011/0003734 A1* | 1/2011 | Yildiz | C07K 14/28 514/2.8 |
| 2011/0287443 A1* | 11/2011 | Retallack | C07K 14/34 435/7.1 |
| 2015/0150959 A1 | 6/2015 | Watnick | |
| 2015/0165019 A1 | 6/2015 | Del Giudice et al. | |

FOREIGN PATENT DOCUMENTS

| | | |
|---|---|---|
| WO | WO 2008/018903 A2 | 2/2008 |
| WO | WO 2012014073 A2 * | 2/2012 |
| WO | WO 2014/128555 A2 | 8/2014 |
| WO | WO 2015/095335 A1 | 6/2015 |

OTHER PUBLICATIONS

Krzych et al. J. Exp. Med. 162: 311-323, 1985.*
Svennerholm. Indian J. Med. Res. 133: 188-194, Feb. 2011.*
Chen et al. Infect. Immun. 66: 1648-1653, 1998.*
Dasgupta et al. Vaccine 12: 359-364, 1994, abstract.*
Absalon et al., A communal bacterial adhesin anchors biofilm and bystander cells to surfaces. PLoS Pathog. Aug. 2011;7(8):e1002210. doi: 10.1371/journal.ppat.1002210. Epub Aug. 25, 2011.
Absalon et al., The bacterial biofilm matrix as a platform for protein delivery. MBio. Jul. 17, 2012;3(4):e00127-12. doi: 10.1128/mBio.00127-12.
GenBank Accession No. NP-231522. Heidelberg et al., DNA sequence of both chromosomes of the cholera pathogen Vibrio cholera. Nature. 2000;406(6795):477-483. Dec. 17, 2014.
Giglio et al., Structural basis for biofilm formation via the Vibrio cholerae matrix protein RbmA. J Bacteriol. Jul. 2013;195(14):3277-86. doi: 10.1128/JB.00374-13. Epub May 17, 2013.
Heidelberg et al., DNA sequence of both chromosomes of the cholera pathogen Vibrio cholerae. Nature. Aug. 3, 2000;406(6795):477-84.
Kaper et al., Recombinant nontoxinogenic Vibrio cholerae strains as attenuated cholera vaccine candidates. Nature. Apr. 12-18, 1984;308(5960):655-8.

(Continued)

*Primary Examiner* — Sarvamangala Devi
(74) *Attorney, Agent, or Firm* — Wolf, Greenfield & Sacks, P.C.

(57) ABSTRACT

Some aspects of this disclosure provide engineered exopolysaccharide-associated proteins, engineered bacteria expressing such proteins, and engineered biofilms comprising such proteins. Some aspects of this disclosure provide methods for engineering exopolysaccharide-associated proteins, and for the generation of engineered bacteria and biofilms expressing or comprising such proteins. Some aspects of this disclosure provide compositions and methods useful for the generation of vaccines and the vaccination of subjects, for delivering molecules of interest to a target site, for example, a surface, for purification of molecules of interest, for example, from bioreactors comprising engineered bacteria as provided herein, and for bioremediation applications, such as the cleanup of environmental pollutants.

6 Claims, 6 Drawing Sheets

Specification includes a Sequence Listing.

(56) References Cited

OTHER PUBLICATIONS

Levine et al., Evaluation in humans of attenuated Vibrio cholerae El Tor Ogawa strain Texas Star-SR as a live oral vaccine. Infect Immun. Feb. 1984;43(2):515-22.
International Search Report and Written Opinion for International Application No. PCT/US17/38045 dated Dec. 22, 2017.
Silva et al., Vibrio cholerae Biofilms and Cholera Pathogenesis. PLoS Negl Trop Dis. Feb. 4, 2016;10(2):e0004330. doi: 10.1371/journal.pntd.0004330. eCollection Feb. 2016. Review.
U.S. Appl. No. 16/310,544, filed Dec. 17, 2018, Watnick et al.
EP 13813283.2, Sep. 14, 2018, European Examination Report.
EP 13813283.2, Mar. 14, 2019, European Office Action.
PCT/US2017/038045, Dec. 27, 2018, International Preliminary Report on Patentability.
EP 13813283.2, Dec. 4, 2015, Supplementary European Search Report.
PCT/US2013/049337, Dec. 18, 2013, Invitation to Pay Additional Fees.
PCT/US2013/049337, Mar. 4, 2014, International Search Report and Written Opinion.
PCT/US2013/049337, Jan. 15, 2015, International Preliminary Report on Patentability.

\* cited by examiner

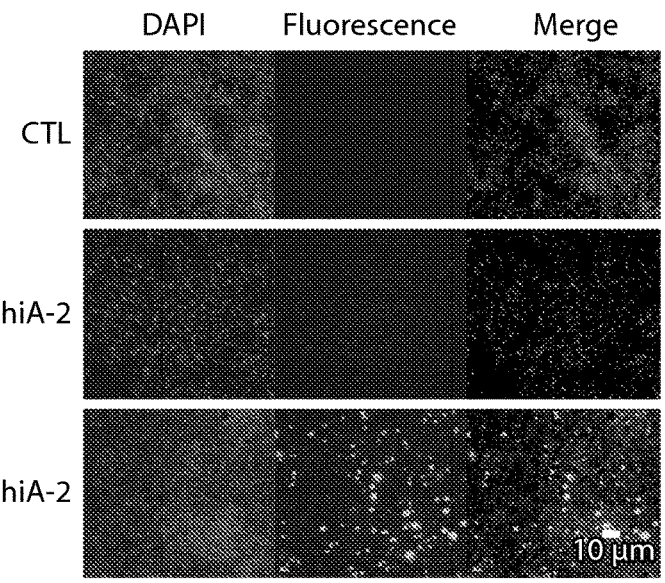
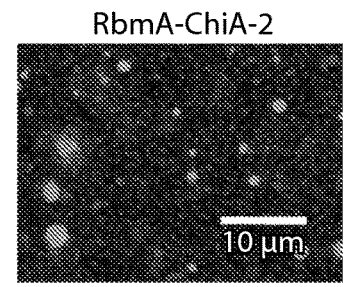
Fig. 2A
Fig. 2B
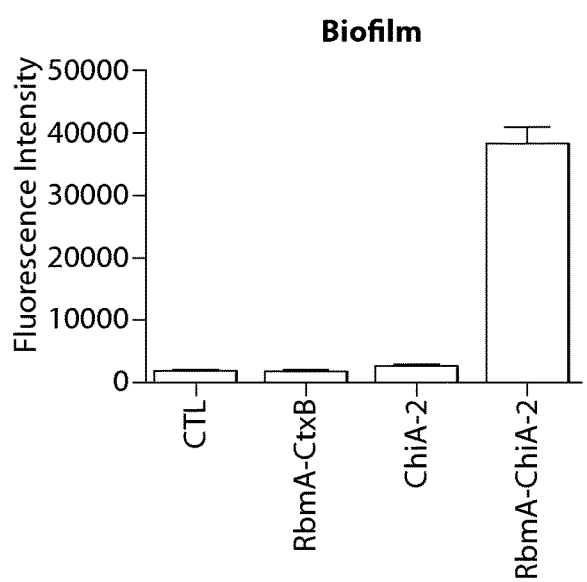
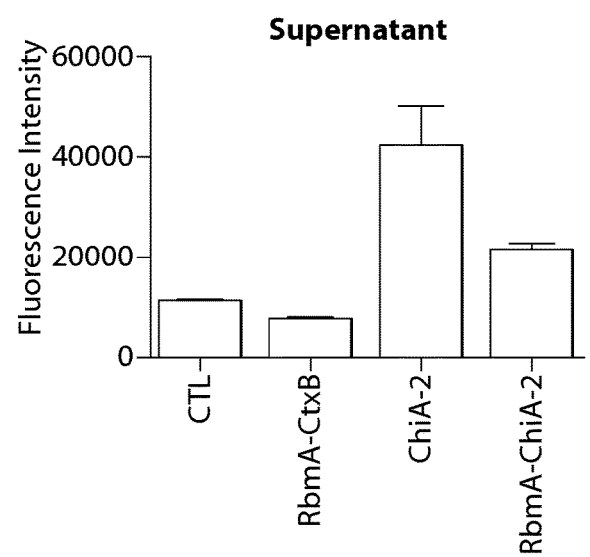
Fig. 2C
Fig. 2D

BACTERIAL BIOFILM MATRIX AS A PLATFORM FOR PROTEIN DELIVERY

RELATED APPLICATIONS

This application is a national stage filing under 35 U.S.C. 371 of International Application PCT/US2013/049337, filed Jul. 3, 2013, which claims priority under 35 U.S.C. § 119(e) to U.S. provisional patent application, U.S. Ser. No. 61/668, 417, filed Jul. 5, 2012, and entitled Bacterial Biofilm Matrix As A Platform For Antigen Presentation And Enzyme Delivery, and U.S. provisional patent application, U.S. Ser. No. 61/780,079, filed Mar. 13, 2013, entitled Bacterial Biofilm Matrix As A Platform For Antigen Presentation And Enzyme Delivery, the contents of which are incorporated by reference in their entirety. International Application PCT/US2013/049337 was published under PCT Article 21(2) in English.

GOVERNMENT LICENSE RIGHTS

This invention was made with U.S. government support under grant number AI50032 awarded by the National Institutes of Health (NIH). The U.S. government has certain rights in the invention.

BACKGROUND

Bacterial biofilm formation is the process by which bacteria adhere to surfaces to form single or multilayer structures. These biofilm structures are found on biotic surfaces such as the epithelia of animals and on abiotic surfaces such as those of mineral deposits, soil, walls of bioreactors, and air-water interfaces. The bacterial biofilm matrix is comprised of exopolysaccharide, proteins, and DNA.

SUMMARY

Bacterial biofilms, which are often described as "slime," have been vilified in medicine and industry. While much research has been performed to develop methods and materials that avoid the formation of biofilms on surfaces, e.g., on surfaces of medical devices or bioreactors, some aspects of this disclosure are based on the recognition that biofilms can be engineered to be useful in a number of biomedical and biotechnological applications.

In contrast to the conventional paradigm that biofilm exopolysaccharides function as the adhesive material that cements cell-surface and intercellular interactions, some aspects of this disclosure provide that biofilm exopolysaccharides actually serve as a scaffold for cellular proteins which mediate these adhesive interactions. Some aspects of this disclosure are based on the recognition that the cellular proteins mediating cell adhesion in biofilms are abundant in biofilms, and that these cellular proteins can be used to deliver heterologous molecules, e.g., enzymes, antigens, binding agents, detection agents, or small molecules, to biofilms in order to engineer novel biofilm functionalities.

Some aspects of this disclosure relate to the identification of several secreted proteins that are retained in the bacterial biofilm matrix by their association with the biofilm exopolysaccharide scaffold. As described in more detail elsewhere herein, these exopolysaccharide-associated proteins show different spatial distribution patterns within the biofilm. Some aspects of this disclosure are based on the recognition that such exopolysaccharide-associated proteins can be used to engineer biofilms for various applications, e.g., to serve as reservoirs for surface-active secreted proteins of biomedical, bioengineering, or biotechnological importance. Accordingly, some aspects of this disclosure provide that the biofilm matrix can be exploited, among other uses, as a vehicle for concentration of molecules, e.g., enzymes or antigens, on the surfaces of cells and as a delivery system targeting abiotic surfaces. Because of their affinity for surfaces, biofilms engineered according to aspects of this disclosure are also ideal vehicles for presentation of vaccine antigens and for delivery of enzymes of therapeutic or bioremediative importance to surfaces.

The technology described herein is broadly applicable, with envisioned applications ranging from vaccine development, treatment of digestive dysfunction, biotechnology (e.g., concentration, isolation, or purification of recombinant proteins from bioreactors), bioremediation (e.g., oil spill clean-up), molecular biology, and others.

Some aspects of this disclosure provide a composition comprising (i) a bacterium associated with an exopolysaccharide; (ii) an exopolysaccharide-associated protein, or an exopolysaccharide-binding fragment thereof; and (iii) a heterologous molecule conjugated to the exopolysaccharide-associated protein, or an exopolysaccharide-binding fragment thereof. In some embodiments, the heterologous molecule is a heterologous protein. In some embodiments, the heterologous protein is an enzyme, or an antigen. In some embodiments, the heterologous protein is fused to the exopolysaccharide-associated protein, or to the exopolysaccharide-binding fragment thereof, thus forming a fusion protein. In some embodiments, the fusion protein is encoded by a recombinant nucleic acid comprised in the bacterium. In some embodiments, the exopolysaccharide-associated protein is a secreted protein. In some embodiments, the exopolysaccharide-associated protein is an extracytoplasmic protein. In some embodiments, the exopolysaccharide-associated protein comprises a β-prism lectin domain, or a fragment thereof. In some embodiments, the exopolysaccharide-associated protein comprises an FG-GAP domain. In some embodiments, the exopolysaccharide-associated protein comprises a β-prism lectin domain flanked by an FG-GAP domain. In some embodiments, the exopolysaccharide-associated protein is a type I β-prism lectin domain-containing protein. In some embodiments, the exopolysaccharide-associated protein is Bap1, RbmA, RbmC, or HlyA. In some embodiments, the heterologous molecule comprises an antigen. In some embodiments, the antigen comprises an antigen of a pathogen. In some embodiments, the heterologous molecule comprises an enzyme. In some embodiments, the enzyme is a therapeutic enzyme. In some embodiments, the enzyme is selected from the group consisting of lactase, a pancreatic enzyme, an oil-degrading enzyme, beta-galactosidase, mucinase, cellulase, isomaltase, or alginase. In some embodiments, the heterologous molecule comprises a binding agent. In some embodiments, the binding agent is selected from the group comprising an antibody, an antigen-binding antibody fragment, a nanobody, an ScFv, an adnectin, a lectin, a ligand, or an affinity tag. In some embodiments, the heterologous molecule comprises a detection agent. In some embodiments, the composition further comprises a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion. In some embodiments, the bacterium is a gram-negative bacterium. In some embodiments, the bacterium is a gram-positive bacterium. In some embodiments, the bacterium is a non-pathogenic bacterium. In some embodiments, the bacterium is a *Vibrio* sp. bacterium. In some embodiments, the bacterium is a *Vibrio cholerae* bacterium. In some embodiments, the bacterium is an *E. coli* bacterium.

Some aspects of this disclosure provide a composition comprising (i) an exopolysaccharide-associated protein, or an exopolysaccharide-binding fragment thereof; and (ii) a heterologous molecule conjugated to the exopolysaccharide-associated protein, or an exopolysaccharide-binding fragment thereof. In some embodiments, the heterologous molecule comprises a heterologous protein. In some embodiments, the heterologous protein is an enzyme, or an antigen. In some embodiments, the heterologous protein is fused to the exopolysaccharide-associated protein, or to the exopolysaccharide-binding fragment thereof, thus forming a fusion protein. In some embodiments, the exopolysaccharide-associated protein is a secreted protein. In some embodiments, the exopolysaccharide-associated protein is an extracytoplasmic protein. In some embodiments, the exopolysaccharide-associated protein comprises a β-prism lectin domain, or a fragment thereof. In some embodiments, the exopolysaccharide-associated protein comprises an FG-GAP domain. In some embodiments, the exopolysaccharide-associated protein comprises a β-prism lectin domain flanked by an FG-GAP domain. In some embodiments, the exopolysaccharide-associated protein is a type I β-prism lectin domain-containing protein. In some embodiments, the exopolysaccharide-associated protein is Bap1 (SEQ ID NO: 1), RbmA (SEQ ID NO: 2), RbmC (SEQ ID NO: 3), or HlyA (SEQ ID NO: 4). In some embodiments, the heterologous molecule comprises an antigen. In some embodiments, the antigen comprises an antigen of a pathogen. In some embodiments, the heterologous molecule comprises an enzyme. In some embodiments, the enzyme is a therapeutic enzyme. In some embodiments, the enzyme is selected from the group consisting of lactase, a pancreatic enzyme, an oil-degrading enzyme, beta-galactosidase, mucinase, cellulase, isomaltase, or alginase. In some embodiments, the heterologous molecule comprises a binding agent. In some embodiments, the binding agent is selected from the group comprising an antibody, an antigen-binding antibody fragment, a nanobody, an ScFv, an adnectin, a lectin, a ligand, or an affinity tag. In some embodiments, the heterologous molecule comprises a detection agent. In some embodiments, the compositions further comprises a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion.

Some aspects of this disclosure provide a vaccine, comprising (i) a bacterium associated with an exopolysaccharide; (ii) an exopolysaccharide-associated protein, or an exopolysaccharide-binding fragment thereof, that binds the exopolysaccharide of (i); and (iii) an antigen conjugated to the exopolysaccharide-associated protein, or an exopolysaccharide-binding fragment thereof. In some embodiments, the exopolysaccharide-associated protein, or exopolysaccharide-binding fragment thereof, is fused to the antigen, thus forming a fusion protein. In some embodiments, the bacterium comprises a recombinant nucleic acid encoding the fusion protein. In some embodiments, the fusion protein is expressed by the bacterium. In some embodiments, the exopolysaccharide is an exopolysaccharide secreted by the bacterium. In some embodiments, the exopolysaccharide is bound by the bacterium. In some embodiments, the fusion protein is bound by the exopolysaccharide. In some embodiments, the antigen is an antigen of a pathogen. In some embodiments, the exopolysaccharide-associated protein is a secreted protein. In some embodiments, the exopolysaccharide-associated protein is an extracytoplasmic protein. In some embodiments, the exopolysaccharide-associated protein comprises a β-prism lectin domain, or a fragment thereof. In some embodiments, the exopolysaccharide-associated protein comprises an FG-GAP domain. In some embodiments, the exopolysaccharide-associated protein comprises a β-prism lectin domain flanked by an FG-GAP domain. In some embodiments, the exopolysaccharide-associated protein is a type I β-prism lectin domain-containing protein. In some embodiments, the exopolysaccharide-associated protein is Bap1 (SEQ ID NO: 1), RbmA (SEQ ID NO: 2), RbmC (SEQ ID NO: 3), or HlyA (SEQ ID NO: 4). In some embodiments, the vaccine further comprises an adjuvant. In some embodiments, the vaccine is a killed whole cell vaccine. In some embodiments, the bacterium is a pathogenic bacterium. In some embodiments, the bacterium is *Vibrio cholerae*. In some embodiments, the bacterium is *E. coli*. In some embodiments, the antigen comprises an antigen of a bacterial toxin. In some embodiments, the bacterial toxin is a cholera toxin. In some embodiments, the cholera toxin is the B subunit of cholera toxin (e.g., MIKLKFGVFFTVLLSSAYAHGTPQNITDLCAEYHNTQI-YTLNDKIFSYTESLAGKREM AIITFKNGAIFQVEVPG-SQHIDSQKKAIERMKDTLRIAYLTEAKVEKLCVWNN KTPHA IAAISMAN SEQ ID NO: 5). In some embodiments, the vaccine is administered to a subject. Accordingly, some embodiments provide a method of vaccinating a subject against a pathogen. In some embodiments, the method comprises administering to the subject an effective amount of a vaccine described herein. In some embodiments, the vaccine is administered in an amount sufficient to elicit an immune response against the bacterium and/or against the antigen. In some embodiments, the vaccine is administered in an amount sufficient to immunize the subject against the bacterium and/or against the antigen.

Some aspects of this disclosure provide a method for delivering a molecule to a target site, the method comprising delivering to the target site a bacterium associated with an exopolysaccharide that binds an exopolysaccharide-associated protein, or an exopolysaccharide-binding fragment thereof, wherein the exopolysaccharide-associated protein, or an exopolysaccharide-binding fragment thereof, binds the molecule. In some embodiments, the target site is a surface. In some embodiments, the target site is an air/water interface. In some embodiments, the heterologous molecule comprises a polypeptide. In some embodiments, the polypeptide is fused to the exopolysaccharide-associated protein or the exopolysaccharide binding protein fragment. In some embodiments, the bacterium comprises a recombinant nucleic acid encoding the polypeptide fused to the exopolysaccharide-associated protein or the exopolysaccharide binding protein fragment. In some embodiments, the molecule comprises a therapeutic protein. In some embodiments, the method comprises administering an effective amount of the bacterium to a subject. In some embodiments, the bacterium is a non-pathogenic bacterium. In some embodiments, the molecule is an enzyme and wherein the target site is a digestive organ of the subject. In some embodiments, the target site is the intestinal tract of the subject. In some embodiments, the molecule is lactase, a pancreatic enzyme, beta-galactosidase, mucinase, cellulase, isomaltase, or alginase. In some embodiments, the bacterium can colonize the intestinal tract of the subject. In some embodiments, the bacterium is administered orally. In some embodiments, the molecule is a mucus-digesting enzyme, and wherein the target site is the lung of the subject. In some embodiments, the mucus-digesting enzyme is mucinase or alginase. In some embodiments, the bacterium can colonize the lung of the subject. In some embodiments, the bacterium is administered via an aerosol. In some embodiments, the molecule is an enzyme that can digest a contaminant. In some embodiments, the contaminant is oil. In some embodiments, the molecule is an oil-digesting enzyme. In some embodiments, the target site is an environmental water-air interface.

Some aspects of this disclosure provide a bacterial biofilm comprising an engineered bacterium as described herein, for example, a bacterium associated with an exopolysaccharide that is bound by an exopolysaccharide-associated protein (or an exopolysaccharide-binding fragment thereof) conjugated to a heterologous molecule.

Some aspects of this disclosure provide a method for modifying the surface of a bacterium. In some embodiments, the method comprises contacting a bacterium associated with an exopolysaccharide with a composition comprising a heterologous molecule conjugated to an exopolysaccharide-associated protein or an exopolysaccharide-binding fragment thereof, wherein the exopolysaccharide-associated protein or the exopolysaccharide-binding fragment thereof binds to the exopolysaccharide. In some embodiments, the composition is a composition as described herein.

Some aspects of this disclosure provide a method of targeting a molecule to a biofilm. In some embodiments, the method comprises contacting a biofilm that comprises an exopolysaccharide with an exopolysaccharide-associated protein, or an exopolysaccharide-binding fragment thereof, conjugated to the molecule. In some embodiments, the biofilm comprises a pathogen and the molecule comprises a polypeptide toxic to the pathogen.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 1. An RbmA-CtxB fusion protein is retained in the biofilm matrix. (A) Immunofluorescent imaging of the distribution of RbmA-FLAG (RbmA) or RbmA-CtxB fusion protein (RbmA-CtxB) in a biofilm formed by wild-type $V.$ cholerae carrying a plasmid encoding this protein. RbmA-FLAG and the fusion protein were visualized with anti-FLAG and anti-CtxB antibodies, respectively. Bacterial DNA was stained with DAPI. A biofilm formed by wild-type $V.$ cholerae carrying an empty vector and developed with the anti-CtxB antibody (CTL) is included as a control. (B) An expanded view of the distributions of RbmA-FLAG and RbmA-CtxB in the biofilm.

FIG. 2. An enzymatically active RbmA-ChiA-2-FLAG fusion protein is retained in the biofilm matrix. (A) Immunofluorescent imaging of the distribution of ChiA-2-FLAG or RbmA-ChiA-2-FLAG in a biofilm formed by wild-type *V. cholerae* carrying a plasmid encoding each of these proteins. The proteins were visualized with an anti-FLAG antibody. Bacterial DNA was stained with DAPI. As a control, a biofilm formed by wildtype *V. cholerae* carrying an empty vector was developed with an anti-FLAG antibody (CTL). (B) An expanded view of the distribution of RbmA-ChiA-2-FLAG in the biofilm. Chitinase activity measured in the biofilms (C) and supernatants (D) of wild-type *V. cholerae* carrying an empty vector (CTL) or a plasmid encoding RbmA-CtxB (RbmACtxB), ChiA-2-FLAG (ChiA-2), or RbmA-ChiA-2-FLAG (RbmA-ChiA-2). The chitinase activity in the biofilm of the strain expressing RbmA-ChiA-2-FLAG was approximately 40 times higher. This difference was statistically significantly different from that in all other biofilms ($p \leq 0.0003$). Similarly, chitinase activity in the supernatants of strains expressing either RbmA-ChiA-2-FLAG or ChiA-2-FLAG was significantly different from that of strains carrying the control vector ($p=0.007$ and $p=0.0215$, respectively) or the RbmA-CtxB fusion ($p=0.0025$ or $p=0.0149$, respectively). The difference in chitinase activity between the supernatants of the strains expressing RbmA-ChiA-2-FLAG and ChiA-2-FLAG was not significantly different ($p=0.07$).

FIG. 3. A *V. cholerae* Δbap1ΔrbmAΔrbmC triple mutant does not make a biofilm but can recruit the chitinase activity of RbmA-ChiA-2-FLAG to the cell surface. (A) Quantification of biofilms formed by wild-type *V. cholerae* (WT), an exopolysaccharide mutant (ΔvpsL), and a Δbap1ΔrbmAΔrbmC mutant (triple) carrying either an empty vector (pCTL) or a plasmid encoding RbmA (pRbmA), and (B) the pellicle formed by a Δbap1ΔrbmAΔrbmC mutant carrying either an empty vector (CTL) or plasmids encoding RbmA-FLAG (RbmA), RbmA-CtxB (RbmA-CtxB), ChiA-2-FLAG (ChiA-2), or RbmA-ChiA-2-FLAG (RbmA-ChiA-2). Chitinase activity in the cellular fraction (C) and supernatants (D) of *V. cholerae* Δbap1ΔrbmAΔrbmC mutant carrying an empty vector or a plasmid encoding RbmA-CtxB, ChiA-2-FLAG, or RbmA-ChiA-2-FLAG. Chitinase activity in the cellular fraction of the mutant expressing RbmA-ChiA-2-FLAG was significantly different from strains expressing all other recombinant proteins ($p<0.0001$). The chitinase activity in the supernatants of mutants expressing ChiA-2-FLAG and RbmA-ChiA-2-FLAG was significantly different from those of the mutant carrying an empty vector ($p=0.034$ and $p=0.0172$) and the mutant expressing RbmA-CtxB ($p=0.039$ and $p=0.0215$). The difference in chitinase activity between the supernatants of the strains expressing RbmA-ChiA-2-FLAG and ChiA-2-FLAG was not significantly different ($p=0.535$).

FIG. 4. Structures of β-prism domain proteins: (A) In Bap1 and RbmC, the β-prism domain is surrounded by FG-GAP domains that likely form a β-propeller. HlyA consists of spatially separated cytolysin, β-trefoil, and β-prism domains. (B) Crystal structure of HlyA.

FIG. 5. Bap1 and RbmC are required for anchoring of the biofilm to a surface, while RbmA stabilizes intercellular attachments. Wild-type *V. cholerae* as well as ΔvpsL, ΔrbmA, Δbap1ΔrbmC, and rescued Δbap1ΔrbmC mutant biofilms undisturbed (U), after shaking (S), or after vortexing (V). A ΔrbmA biofilm is dispersed by vortexing, while the Δbap1ΔrbmC mutant falls to the bottom of the tube when shaken gently.

FIG. 6. Distinct distributions of the proteins RbmA and Bap1 in the biofilm matrix: Immunofluorescent analysis of biofilms formed by strains containing a chromosomally encoded affinity tag at the C-terminus of RbmA (A) or Bap1 (B). Immunofluorescence shows that RbmA is distributed throughout the biofilm, while Bap1 is concentrated at the surface. (C) Fluorescent intensity plotted as a function of biofilm height (Z-axis) for each of these biofilms.

DETAILED DESCRIPTION

Introduction

Figure 3A:
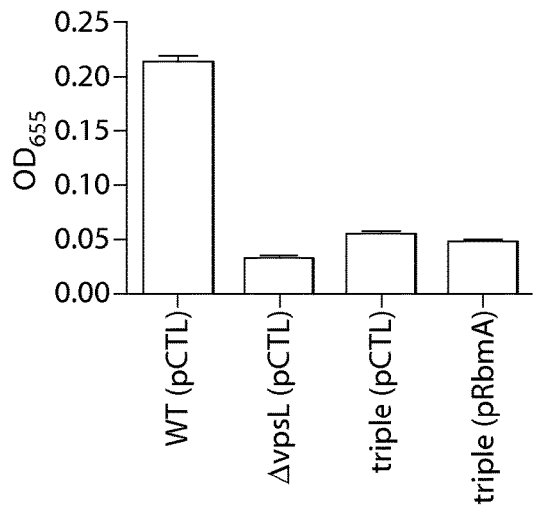

The occurrence of surface-associated bacterial structures known as biofilms is viewed as an undesirable phenomenon in the context of many biomedical and biotechnological applications. Biofilm formation can lead to failure of biomedical devices, to greatly reduced continuous production times and yields in production-scale bioreactors, and to many other detrimental consequences. Accordingly, biofilms are the target of intense antimicrobial research efforts.

In contrast to the conventional paradigm that biofilms are undesirable contaminants, some aspect of this disclosure provide that biofilms can be engineered to confer novel structural and/or functional characteristics upon them, making them useful tools in many biomedical and biotechnological applications. For example, as described in more detail herein, engineered biofilms, bacteria, and biofilm-associated proteins provided herein are useful for vaccine development and production, isolation and purification of bioreactor products, delivery of molecules to a target site in vivo, and bioremediation applications, such as cleaning up environmental pollutants.

This paradigm shift away from the view that biofilms are undesirable contaminants and towards the view that biofilms can be engineered to serve highly desirable purposes in a variety of applications is based, in part, on the recognition of how biofilms form and maintain their structure and their adhesion to surfaces. In contrast to the conventional view that exopolysaccharides shed by bacteria in a biofilm function as the "glue" that mediates adhesion of the cells within the biofilm to each other and also adhesion of the biofilm to a surface, some aspects of this disclosure provide that biofilm exopolysaccharides function in a different way. Namely, as described in more detail herein, biofilm exopolysaccharides provide a scaffold to which cellular proteins, secreted by or expressed on the surface of the cells within the biofilm, adhere. These cellular proteins are referred to herein as exopolysaccharide-associated proteins.

Some aspects of this disclosure are based on the recognition that the cellular proteins mediating cell adhesion in biofilms, exopolysaccharide-associated proteins, are abundant in biofilms, and that different exopolysaccharide-associated proteins exhibit different spatial distributions throughout a given biofilm. Some aspects of this disclosure relate to the identification and characterization of several secreted or extracytoplasmic proteins that are retained in the bacterial biofilm matrix by their association with the biofilm exopolysaccharide scaffold. Some aspects of this disclosure provide engineered exopolysaccharide-associated proteins, for example conjugated with a heterologous molecule, e.g., a protein, an enzyme, antigen, binding agent, detection agent, or small molecules. Such engineered exopolysaccharide-associated proteins can be used to deliver heterologous molecules to biofilms, for example, in order to engineer novel biofilm functionalities and structures. Depending on the spatial distribution of a given exopolysaccharide-associated protein, a heterologous molecule can be delivered to the surface, the interior, or evenly throughout a given biofilm according to some aspects of this disclosure.

Some aspects of this disclosure are based on the recognition that engineered exopolysaccharide-associated proteins in bacteria, as provided herein, can be used to engineer biofilms for various applications, e.g., to serve as reservoirs for surface-active secreted proteins of biomedical, bioengineering, or biotechnological importance. Accordingly, some aspects of this disclosure provide that the biofilm matrix can be exploited, among other uses, as a vehicle for concentration of molecules, e.g., enzymes or antigens, on the surfaces of cells and as a delivery system targeting abiotic surfaces. Because of their affinity for surfaces, biofilms engineered according to aspects of this disclosure are also ideal vehicles for presentation of vaccine antigens and for delivery of enzymes of therapeutic or bioremediative importance to surfaces.

Some aspects of this disclosure provide engineered exopolysaccharide-associated proteins, engineered bacteria expressing such proteins, and engineered biofilms comprising such proteins. Some aspects of this disclosure provide methods for engineering exopolysaccharide-associated proteins, and for the generation of engineered bacteria and biofilms expressing or comprising such proteins. Some aspects of this disclosure provide compositions and methods useful for the generation of vaccines and the vaccination of subjects, for delivering molecules of interest to a target site, for example, a surface, for purification of molecules of interest, for example, from bioreactors comprising engineered bacteria as provided herein, and for bioremediation applications, such as the cleanup of environmental pollutants.

The technology described herein is broadly applicable to any biofilm comprising an exopolysaccharide scaffold and exopolysaccharide-associated proteins mediating cell-cell adhesion and/or cell-surface adhesion within the biofilm. Accordingly, exemplary envisioned applications range from, without limitation, therapeutic and prophylactic medical uses, e.g., vaccine development and treatment of digestive dysfunction, to biotechnological uses (e.g., concentration, isolation, or purification of recombinant proteins or other products from bioreactors), to bioremediation (e.g., oil spill clean-up), to molecular biology, and others. For example, the technology described herein represents an economical and versatile new platform for delivery of protein antigens or immune adjuvants in whole cell vaccines. For another example, the technology described herein can be used to deliver functional proteins to surfaces. For instance, a commensal bacterium such as *E. coli* or a commonly used probiotic might be used to deliver a digestive enzyme, for example, lactase or a pancreatic enzyme, to the intestinal brush border of a subject with a deficiency in the digestive enzyme, (e.g., subjects with lactase deficiency or cystic fibrosis). A nonpathogenic bacterium colonizing the lung of a cystic fibrosis patient might be re-engineered according to some aspects of this disclosure to deliver mucinase or alginase, thus helping to clear biofilm-associated *Pseudomonas aeruginosa* from the lung. For another example, the technology described herein can be used to deliver enzymes that are useful in the digestion of an environmental pollutant, e.g., oil, to contaminated surfaces, e.g., polluted water-air surfaces of lakes or oceans. For yet another example, secreted proteins destined for purification, e.g., from a culture in a production-scale bioreactor, could be fused to an exopolysaccharide-associated protein. Cells expressing such a fusion protein would retain the secreted protein and could be used as a "biocolumn." Such cells could be grown, either in suspension or as a biofilm, and subsequently pelleted to isolate the secreted protein of interest. If the fusion protein comprises a protease cleavage site separating the secreted protein of interest from the exopolysaccharide-associated protein, the protein of interest can be released from the bacterial pellet by protease digestion and subsequent elution.

Some aspects of this disclosure demonstrate the feasibility of an application of the bacterial biofilm matrix exopolysaccharide as a scaffold for localization and presentation of proteins and for delivery of functional enzymes to surfaces. The "proof of principle" experiments in the diarrheal pathogen *V. cholerae* described in more detail in the Examples section herein can be extended to other bacteria that also form biofilms incorporating structural exopolysaccharides and exopolysaccharide-associated proteins. Such bacteria include, for example, other biofilm-forming diarrheal pathogens [10-13]. However, it will be understood by those of skill in the art that the inventive concepts described herein can be applied to any biofilm matrix exhibiting similar characteristics to the biofilms specifically described. Additional applications of the technology provided herein will be apparent to those of skill in the art based on the instant disclosure. The exemplary embodiments listed above serve to illustrate the versatility of the instantly disclosed technology. The disclosure is not limited in this respect.

The term bacterium refers to a prokaryotic microorganism from the taxon Bacteria. Names of bacteria described herein are provided according to international rules for the naming of bacteria and taxonomic categories and for the ranking of them in the International Code of Nomenclature of Bacteria by the International Committee on Systematic Bacteriology (ICSB).

The term Gram staining refers to a method of staining bacteria developed by Hans Christian Gram, which allows differentiating bacterial species into two large groups (Gram-positive and Gram-negative, see, e.g., Gram, H C (1884). *Über die isolierte Färbung der Schizomyceten in Schnitt-and Trockenpräparaten* (German). Fortschritte der Medizin 2: 185-189. English translation in: Brock, T. D. (1999). Milestones in Microbiology 1546-1940 (2 ed.). ASM Press. pp. 215-218. ISBN 1-55581-142-6); the contents of each of which are incorporated herein in their entirety). Gram staining detects peptidoglycan in Gram positive bacteria via crystal violet staining. Gram-positive bacteria retain crystal violet, resulting in a purple/blue color. In some embodiments, Gram staining also utilizes a counter stain, e.g., fuchsine or safranin, for detecting Gram-negative bacteria, typically resulting in a pink/red color.

The term gram-negative, in the context of bacteria, refers to bacteria that are not stained dark blue or violet by Gram staining, because they cannot retain the crystal-violet stain used in Gram staining. In some embodiments of Gram staining, a counterstain is used (e.g., safranin or fuchsine) that is retained by Gram-negative bacteria, staining them red or pink. Some Gram-negative bacteria are pathogens in humans, for example, some species of *Escherichia* sp., *Enterobacter* sp. (e.g., *Enterobacter cloacae*), *Salmonella* sp. (e.g., *Salmonella enteritidis, Salmonella typhi*), *Shigella* sp., *Pseudomonas* sp. (e.g., *Pseudomonas aeruginosa*), *Moraxella* sp. (e.g., *Moraxella catarrhalis*), *Neisseria* sp. (e.g., *Neisseria gonorrhoeae, Neisseria meningitidis*), *Helicobacter* sp., (e.g., *Helicobacter pylori*) *Stenotrophomonas* sp., *Vibrio* sp. (e.g., *Vibrio cholerae*), *Legionella* sp. (*Legionella pneumophila*), *Hemophilus* sp. (e.g., *Hemophilus influenzae*), *Klebsiella* sp. (e.g., *Klebsiella pneumoniae*), *Proteus* sp. (e.g., *Proteus mirabilis*), *Serratia* sp. (*Serratia marcescens*).

The term Gram-positive, in the context of bacteria, refers to bacteria that are stained dark blue or violet by Gram staining. Gram-positive bacteria retain the crystal violet stain because of the high amount of peptidoglycan in the cell wall. The cell walls of Gram-positive bacteria typically lack the outer membrane found in Gram-negative bacteria. Some Gram-positive bacteria are pathogens in humans, for example, some species of *Streptococcus* sp., *Staphylococcus* sp., *Corynebacterium* sp., *Listeria* sp., and *Clostridium* sp.

The term non-pathogenic refers to a microorganism, e.g., a bacterium, that does not typically cause a disease in a subject exposed to it. In some embodiments, whether or not a bacterium is pathogenic depends on the type of exposure or administration of the bacterium to the subject. For example, a bacterium may be non-pathogenic or even beneficial if administered into the gastrointestinal tract, but may be pathogenic, e.g., causing inflammation or other disease or disorder, upon exposure of an open wound, administration into the bloodstream, or inhalation. In some embodiments, a non-pathogenic bacterium is a bacterium that does not cause a disease or disorder in a subject, e.g., a human subject, when administered orally, parenterally, subcutaneously, intravenously, intramuscularly, into the lung, into the blood, topically, or into the respiratory tract.

The term pathogen refers to an agent or organism that causes a disease or disorder in a subject, e.g., a human subject. In some embodiments, the pathogen is a bacterium. Bacterial pathogens are well known to those of skill in the art. Bacterial genera comprising bacterial pathogens and exemplary bacterial pathogens include, without limitation, *Bacillus* sp. (e.g., *Bacillus anthracis*) *Bordetella* sp. (e.g., *Bordetella pertussis*); *Borrelia* sp. (e.g., *Borrelia burgdorferi*); *Brucella* sp. (e.g., *Brucella abortus, Brucella canis, Brucella melitensis, Brucella suis*); *Campylobacter* sp. (e.g., *Campylobacter jejuni*); *Chlamydia* sp. and *Chlamydophila* sp. (e.g., *Chlamydia pneumoniae, Chlamydia trachomatis, Chlamydophila psittaci*); *Clostridium* sp. (e.g., *Clostridium botulinum, Clostridium difficile, Clostridium perfringens, Clostridium tetani*); *Corynebacterium* sp. (e.g., *Corynebacterium diphtheriae*); *Enterococcus* sp. (e.g., *Enterococcus faecalis, Enterococcus faecium*); *Escherichia* sp. (e.g., *Escherichia coli*, Enterotoxic *E. coli*, enteropathogenic *E. coli; E. coli* O157:H7); *Francisella* sp. (e.g., *Francisella tularensis*); *Haemophilus* sp. (e.g., *Haemophilus influenzae*); *Helicobacter* sp. (e.g., *Helicobacter pylori*); *Legionella* sp. (e.g., *Legionella pneumophila*); *Leptospira* sp. (e.g., *Leptospira interrogans*); *Listeria* sp. (e.g., *Listeria monocytogenes*); *Mycobacterium* sp. (e.g., *Mycobacterium leprae, Mycobacterium tuberculosis, Mycobacterium ulcerans*); *Mycoplasma* sp. (e.g., *Mycoplasma pneumoniae*); *Neisseria* sp. (e.g., *Neisseria gonorrhoeae, Neisseria meningitidis*); *Pseudomonas* sp. (e.g., *Pseudomonas aeruginosa*); *Rickettsia* sp. (e.g., *Rickettsia rickettsii*); *Salmonella* sp. (e.g., *Salmonella typhi, Salmonella typhimurium*); *Shigella* sp. (e.g., *Shigella sonnei*); *Staphylococcus* sp. (e.g., *Staphylococcus aureus, Staphylococcus epidermidis, Staphylococcus saprophyticus*); *Streptococcus* sp. (e.g., *Streptococcus agalactiae, Streptococcus pneumoniae, Streptococcus pyogenes*); *Treponema* sp. (e.g., *Treponema pallidum*); *Vibrio* sp. (e.g., *Vibrio cholerae*); *Yersinia* sp. (e.g., *Yersinia pestis*).

The term biofilm refers to an aggregate of microorganisms, e.g., bacteria, on a surface. In some embodiments, a biofilm comprises bacterial cells that are embedded within an extracellular matrix comprising extracellular polysaccharides, also sometimes referred to as EPS. Extracellular polysaccharides are also referred to herein as exopolysaccharides. In some embodiments, extracellular matrix components, e.g., exopolysaccharides, are produced and secreted by the cells within the biofilm. Bacterial cells within a biofilm adhere to the extracellular matrix of the biofilm by molecules, e.g., proteins, expressed on the surface of the cells that bind to the biofilm EPS.

The term exopolysaccharide refers to a high-molecular-weight polysaccharide that is secreted by a microorganism.

Typically, exopolysaccharides comprise a polymer of monosaccharides. Some exopolysaccharides, however, also comprise non-carbohydrate substituents (such as acetate, pyruvate, succinate, and phosphate). Exemplary exopolysaccharides include, without limitation acetan (*Acetobacter xylinum*), alginate (*Azotobacter vinelandii*), cellulose (*Acetobacter xylinum*), chitosan (*Mucorales* sp.), curdlan (*Alcaligenes faecalis* var. *myxogenes*), cyclosophorans (*Agrobacterium* sp., *Rhizobium* sp. and *Xanthomonas* sp.), dextran (*Leuconostoc mesenteroides, Leuconostoc dextranicum* and *Lactobacillus hilgardii*), emulsan (*Acinetobacter calcoaceticus*), galactoglucopolysaccharides (*Achromobacter* sp., *Agrobacterium radiobacter, Pseudomonas marginalis, Rhizobium* sp. and *Zooglea* sp.), gellan (*Aureomonas elodea* and *Sphingomonas paucimobilis*), glucuronan (*Sinorhizobium meliloti*), N-acetyl-glucosamine (*Staphylococcus epidermidis*), N-acetyl-heparosan (*Escherichia coli*), hyaluronic acid (*Streptococcus equi*), indican (*Beijerinckia indica*), kefiran (*Lactobacillus hilgardii*), lentinan (*Lentinus elodes*), levan (*Alcaligenes viscosus, Zymomonas mobilis, Bacillus subtilis*), pullulan (*Aureobasidium pullulans*), scleroglucan (*Sclerotium rolfsii, Sclerotium delfinii* and *Sclerotium glucanicum*), schizophyllan (*Schizophylum commune*), stewartan (*Pantoea stewartii* subsp. *stewartii*), succinoglycan (*Alcaligenes faecalis* var *myxogenes, Sinorhizobium meliloti*), xanthan (*Xanthomonas campestris*), and welan (*Alcaligenes* sp.).

The term exopolysaccharide-associated protein refers to a protein that binds to an exopolysaccharide via non-covalent interactions with a $K_D$ of <$10^{-5}$ M, <$10^{-6}$ M, <$10^{-7}$ M, <$10^{-8}$ M, <$10^{-9}$ M, <$10^{-10}$ M, <$10^{-11}$ M, or <$10^{-12}$ M. The term exopolysaccharide-binding fragment, in the context of exopolysaccharide-associated proteins, refers to a fragment of an exopolysaccharide-associated protein, wherein the fragment retains the exopolysaccharide binding characteristics of the parent protein, or binds the exopolysaccharide with a $K_D$ of <$10^{-5}$ M, <$10^{-6}$M, <$10^{-7}$ M, <$10^{-8}$ M, <$10^{-9}$ M, <$10^{-10}$ M, <$10^{-11}$ M, or <$10^{-12}$ M. Exopolysaccharide-associated proteins are known to those of skill in the art. Some exemplary exopolysaccharide-associated proteins and exopolysaccharide-binding fragments thereof are described herein, including, but not limited to Bap1, RbmA, RbmC, and HlyA. Below are exemplary, representative sequences of Bap1, RbmA, RbmC, and HlyA from *Vibrio cholerae*. It is to be understood that these sequences are for illustration purposes only and are not meant to limit the scope of this disclosure. Those of skill in the art will know or will be able to ascertain additional sequences of Bap1, RbmA, RbmC, and HlyA, and of additional exopolysaccharide-binding proteins, both from *Vibrio* sp. and from other bacteria based on this disclosure and knowledge in the art. The disclosure is not limited in this respect.

Bap1
>vch:VC1888 hemolysin-like protein (A)

(SEQ ID NO: 1)
MKQTKTLTAISVLALSHLMTQSTAFASSSSDIQTKLKWSWSTSVFHPES

NQVMAAPIVVQLNDDNGDKIDEKDVADIIVVTFEGNKYANGGYIRALS

GVDGSELWSYSNGGVIADARYAPAAADLDGDGLIEIVSTSALTPYINIL

DHQGNIKKQLLKSASGWRSVGDIALADINGDGNIEILAADGVYSYESGL

LFSHDWAPSSIAFDSNGDGQREVFANGTLYQNNGAYLWQYQANDTVWFS

SVANLDGDDKPELVVSVPASLSTPENSEIAVLEHDGSVKWRVNNLSNPG

GSVQAVSSFLGKPSSSATTVDAQSAVYGYTDWAHQQRVLAENHQLAIRS

GAVVDAIGANSQNMIGGSGGSLSTIDTSKVRAIDVTYGKNKYTWKYGVL

EMSFTLDNGAKVTVGSKDSAFTYLGLEWKTKTVPYLGVEWRTKTVSYWF

FGWHTKQVAYLAPVWKEKTIPYAVPVTLSKSTTVRYDIPQGSQLLGMNV

WSKEKHLFKHKQQVNAVQFLVGKVTADQSHMGIVYAGYYAVDMYDAQGN

KVWSVANDDLNSGKIGVSAYDFTGDGIDEVLVQDRLRMRILDGQTGRVM

GIIANSSGTLWEYPVVADLEGNNASLIMVANDYDRESQVNHGVFVYESA

NPSKPWRNATRIWNQYAFNFSDINANGTIPTNAQPSWLTHNSFRSATIR

VPLK

EF Hand domain: residues 63-78
VCBS domain: residues 77-135
PQQ enzyme repeat: residues 90-113
FG-GAP repeat: residues 119-13
VCBS domain: residues 125-184
FG-GAP repeat: residues 170-185
FG-GAP repeat: residues 246-267
FG-GAP repeat: residues 555-571
RbmA
>vch:VC0928 hypothetical protein (A)

(SEQ ID NO: 2)
MSNFKGSIMNKRHYYLASCLALLFSTASYAEVDCELQPVIEANLSLNQN

QLASNGGYISSQLGIRNESCETVKFKYWLSIKGPEGIYFPAKAVVGVDT

AQQESDALTDGRMLNVTRGFWVPEYMADGKYTVSLQVVAENGKVFKANQ

EFVKGVDLNSLPELNGLTIDIKNQFGINSVESTGGFVPFTVDLNNGREG

EANVEFWMTAVGPDGLIIPVNAREKWVIASGDTYSKVRGINFDKSYPAG

EYTINAQVVDIVSGERVEQSMTVVKK

Signal peptide: residues 1-30
RbmC
>vch:VC0930 hemolysin-like protein (A)

(SEQ ID NO: 3)
MTSHYIALAVGLLSLSSNVVQATTNEAEGCIISRLNGEKYCLKVGERSG

YSLPSWIYAHPVDVQAPSGVSVMLSDWDNLSYNRLAVFDRYTGNEDLKN

VKAYNGAYLDFSKPRSMRVLASETYPEACIVSRQTGERFCLKEGERSGY

SLPAYIYGHEVDVEAPLGLGVMLSDWDNLSYNRLAVFGGNTQNEQMRAV

KAYNGETLDFSKPRSMRVVPYDGDSSALNMKLKWSWQGSAFQPNSNQVM

VTPIVAQLNDDNGDGKIDEKDVADLIVVTFEGNKYANGGLVRALSGVDG

SELWSYANGGVIADARYSPAVGDLDGDGIVEIVTTNNRDQFITILDNQG

NIKKQIPTTESGWRIVGDITLADLDHDGSVEILAADGVYNYHSGLVFNH

PWAPSSINVDVDGDQQQEVFSGGTLFQNNGAINWQYQANDAVWFSSLVN

LDNDAEPEIVASVPATFATGDNARFAVLEHDGTIKWEINNTANPGGGVQ

AVSNFLGKAQAVETSEFSKVYGYQPNNNPASIALAVDGKISVRSGFAID

AIGASASTLVGGTGGNLNAAVNVKDIKAIDLTWGKYYWGGYHLLALDFR

MSNGSVISMGSKNYAYSKQTERFTVPAGSRIKGIKAWTAGWLLDGVQFE

LATQNGTNDLDVKGIVYAGYAAVDMYNSKGERVWSVANDDTGSGKIGVS

```
AYDFDNDGIDEVLVQDHARVRVLDGKTGKERASLAHSTATLWEYPIVVD

LEGDNNAELIVAANDFDRQYSINHGVYVYQSADSSKPWKNATRIWNQHA

FHLTNINQDGTLPTFVEPSWLSHNTYRSSTLRAAVGGESPIFGYSNTQQ

SQRVVTADNLMYLRSGFAIDAIGTTVNNLVGGPVQGTNGGVLRAPIALD

QLQSVEVTSGLYNWGGYHIVAIKFTMKDGSSVLLGSTHYASNKKVETYT

VPQGKRIKQINVWTGGWLVEGFQFVY
```

Signal peptide: residues 1-20
FG-GAP repeat: residues 311-328
FG-GAP repeat: residues 684-709
Jacalin type lectin (beta prism) domain: residues 529-639
Jacalin type lectin (beta prism) domain: residues 832-957
HlyA
>vch:VCA0219 haemolysin; K10948 hemolysin (A)

```
                                              (SEQ ID NO: 4)
MPKLNRCAIAIFTILSAISSPTLLANINEPSGEAADIISQVADSHAIKY

YNAADWQAEDNALPSLAELRDLVINQQKRVLVDFSQISDAEGQAEMQAQ

FRKAYGVGFANQFIVITEHKGELLFTPFDQAEEVDPQLLEAPRTARLLA

RSGFASPAPANSETNTLPHVAFYISVNRAISDEECTFNNSWLWKNEKGS

RPFCKDANISLIYRVNLERSLQYGIVGSATPDAKIVRISLDDDSTGAGI

HLNDQLGYRQFGASYTTLDAYFREWSTDAIAQDYRFVFNASNNKAQILK

TFPVDNINEKFERKEVSGFELGVTGGVEVSGDGPKAKLEARASYTQSRW

LTYNTQDYRIERNAKNAQAVSFTWNRQQYATAESLLNRSTDALWVNTYP

VDVNRISPLSYASFVPKMDVIYKASATETGSTDFIIDSSVNIRPIYNGA

YKHYYVVGAHQFYHGFEDTPRRRITKSASFTVDWDHPVFTGGRPVNLQL

ASFNNRCIQVDAQGRLAANTCDSQQSAQSFIYDQLGRYVSASNTKLCLD

GEALDALQPCNQNLTQRWEWRKGTDELTNVYSGESLGHDKQTGELGLYA

SSNDAVSLRTITAYTDVFNAQESSPILGYTQGKMNQQRVGQDHRLYVRA

GAAIDALGSASDLLVGGNGGSLSSVDLSGVKSITATSGDFQYGGQQLVA

LTFTYQDGRQQTVGSKAYVTNAHEDRFDLPAAAKITQLKIWSDDWLVKG

VQFDLN
```

Signal peptide: residues 1-24
Hemolysin N domain:residues 2-187
Leukocidin domain: residues 215-477
Ricin-type beta trefoil domain (a lectin domain): residues 484-599
Jacalin-like=beta prism domain (a lectin domain): residues 620-741

The term protein is used herein interchangeably with the term polypeptide, and refers to a polymer of amino acid residues linked together by peptide bonds. The term refers to proteins, polypeptides, and peptides of any size, structure, or function. A protein may be a naturally occurring protein, a fragment of a naturally occurring protein, or an engineered protein, for example, a recombinant protein, or a protein in which one or more amino acid residues are non-naturally occurring residues, e.g., modified amino acid residues, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. In some embodiments, the term protein refers to a polymer of three or more amino acids linked by a peptide bond, e.g., between 3 and 30, 12 and 60, or 30 and 300, or over 300 amino acids in length. In some embodiments, the protein includes one or more amino acids that does not occur in nature. In some embodiments, the polypeptide includes only natural amino acids. In some embodiments, a protein includes one or more post-translational or post-synthesis modifications, e.g., a glycosylation, amidation, phosphorylation, SUMOylation, PEGylation, or nitrosylation.

The terms conjugating, conjugated, and conjugation refer to an association of two entities, for example, of two molecules (e.g., two proteins), two domains (e.g., a binding domain and an catalytic domain), or a protein and an agent, e.g., a protein binding domain and a small molecule. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., an exopolysaccharide-associated protein and an antigen or enzyme, to form a protein fusion, the two proteins may be conjugated via a polypeptide linker, e.g., an amino acid sequence connecting the C-terminus of one protein to the N-terminus of the other protein.

The term fusion protein refers to a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

The term heterologous, in the context of molecules, e.g., of proteins, peptides, nucleic acids, and small molecules, refers to a molecule that is not in its natural context, e.g., in that it is conjugated with another molecule that it is not naturally conjugated to, or it is expressed in a cell that does not naturally express the molecule. For example, a heterologous protein in the context of a fusion protein is a protein that does not naturally occur as a fusion with the specific fusion partner. For example, an antigen that is not naturally conjugated to, or fused with, an exopolysaccharide-associated protein, e.g., Bpa1, RbmA, RbmC, or HlyA, is a heterologous protein in the context of conjugates or fusion proteins comprising the antigen and the exopolysaccharide-associated protein. Similarly, a nucleic acid that is not typically operably linked to another nucleic acid is heterologous in the context of a nucleic acid construct comprising both nucleic acids operably linked together.

The term secreted protein refers to a protein that is secreted from a cell, for example, from a bacterium. Accordingly, in some embodiments, a secreted protein is a protein that is synthesized within the cell and then released into the extracellular space surrounding the cell. In some embodiments, the protein comprises a signaling peptide, e.g., at the N-terminus of the protein, that targets the protein for secretion. Such signaling peptides, also sometimes referred to as signal peptides or signal sequences, are well known to those of skill in the art. Exemplary signal peptides include, but are not limited to those disclosed by the SPdb Signal Peptide Resource (see, e.g., Choo K H, Tan T W, Ranganathan S. 2005. SPdb—a signal peptide database. BMC Bioinformatics 6:249, accessible at "proline(.)bic(.)nus(.)edu(.)sg/spdb"—last accessed on Mar. 13, 2013; the entire contents of each of which are incorporated herein by reference); the Signal Peptide Database (see, e.g., Katja Kapp, *Signal Peptide Database*. Heidelberg & Thpr.net, accessible at "www(.)signalpeptide(.)de/index.php?m=listspdb_bacteria"—last accessed on Mar. 13, 2013, the entire contents of which are incorporated herein by reference). Exemplary signal suitable peptide sequences include, without limitation, signal peptide sequences from Lectin-like protein BA14k (MNIFKQTCVGAFAVIFGAT-SIAPTMA, SEQ ID NO: 6); Antigen 85-C (MKFLQQM-RKLFGLAAKFPARLTIAVIGTALLAGLVGVVGDTAI-AVA, SEQ ID NO: 7); Alginate biosynthesis protein algF (MNPMTRRHTWTRLACALSLGVAAFAAQA, SEQ ID NO: 8); Probable N-acetylmuramoyl-L-alanine amidase amiA (MSTFKLLKTLTSRRQVLKTGLAALTLSGM-SHAVA, SEQ ID NO: 9); Alpha-amylase (MKLAAC-FLTLLPGFAVA. SEQ ID NO: 10); Beta-lactamase (MHPSTSRPSRRTLLTATAGAALAAATLVPGTAHAS-SGGR; SEQ ID NO: 11); and Chitinase 63 (MRFRH-KAAALAATLALPLAGLVGLASPAQA, SEQ ID NO: 12). Additional suitable signal peptide sequences will be apparent to those of skill in the art, and the disclosure is not limited in this respect.

In some embodiments, a secreted protein is released from a cell into the extracellular space in a manner that no association between the cell and the protein remains after release. In some embodiments, a secreted protein is released from a cell into the extracellular space, but remains attached to the surface of the cell via non-covalent interaction.

The term extracytoplasmic protein refers to a protein of a cell that is expressed on the surface of the cell and abuts or protrudes into the surrounding extracellular space. In some embodiments, an extracytoplasmic protein is not a secreted protein. For example, in some embodiments, an extracytoplasmic protein comprises a transmembrane domain that spans the cell membrane, thus anchoring the protein on the surface of the cell.

The term protein domain refers to a conserved part of a protein sequence and structure that can evolve, fold, function, and/or exist independently of the rest of the protein chain. A domain typically forms a characteristic three-dimensional structure and often can fold independently and stably regardless of its sequence context. Many proteins consist of several structural domains. Typically, protein domains vary in length from between about 25 amino acids up to 500 amino acids in length, even though longer and shorter protein domains exist. Some of the shortest protein domains such as zinc fingers, are stabilized by metal ions or disulfide bridges. Protein domains often form structural or functional units, such as the calcium-binding EF hand domain of calmodulin. Independently stable protein domains can be recombined or fused to produce chimeric proteins having the characteristics of the fused protein domains. For example, an exopolysaccharide binding protein domain can be fused with a binding domain of an antibody to produce a divalent binding protein.

The term β-prism lectin domain is used interchangeably with the term jacalin-like lectin domain, and refers to a mannose-binding lectin domain with a beta-prism fold consisting of three 4-stranded beta-sheets, with an internal pseudo 3-fold symmetry. Some lectins comprising this domain stimulate distinct T- and B-cell functions, such as Jacalin, which binds to the T-antigen and acts as an agglutinin. This domain is found in 1 to 6 copies in lectins. The domain is also found in the salt-stress induced protein from rice and an animal prostatic spermine-binding protein. Proteins containing this domain include: Jacalin, a tetrameric plant seed lectin and agglutinin from *Artocarpus heterophyllus* (jackfruit), which is specific for galactose; Artocarpin, a tetrameric plant seed lectin from *A. heterophyllus*; Lectin MPA, a tetrameric plant seed lectin and agglutinin from *Maclura pomifera* (Osage orange); Heltuba lectin, a plant seed lectin and agglutinin from *Helianthus tuberosus* (Jerusalem artichoke); Agglutinin from *Calystegia sepium* (Hedge bindweed); and Griffithsin, an antiviral lectin from red algae (*Griffithsia* species). See, e.g., Jeyaprakash et al., (2002) "Crystal structure of the jacalin-T-antigen complex and a comparative study of lectin-T-antigen complexes". J. Mol. Biol. 321 (4): 637-45; Jeyaprakash et al., (2004) "Structural basis for the carbohydrate specificities of artocarpin: variation in the length of a loop as a strategy for generating ligand specificity". J. Mol. Biol. 338 (4): 757-70; Lee et al., (1998) "Structure of the complex of *Maclura pomifera* agglutinin and the T-antigen disaccharide, Galbeta1,3GalNAc". J. Biol. Chem. 273 (11): 6312-8; Bourne et al., (1999) "*Helianthus tuberosus* lectin reveals a widespread scaffold for mannose-binding lectins". Structure 7 (12): 1473-82; Bourne et al., (2004) "The crystal structure of the *Calystegia sepium* agglutinin reveals a novel quaternary arrangement of lectin subunits with a beta-prism fold". J. Biol. Chem. 279 (1): 527-33; and Ziolkowska et al., (2006) "Domain-swapped structure of the potent antiviral protein griffithsin and its mode of carbohydrate binding". Structure 14 (7): 1127-35; the entire contents of each of which are incorporated herein by reference. Representative sequences and consensus sequences of β-prism lectin domains are well known to those of skill in the art, e.g., as published in Raval et al., *A database analysis of jacalin-like lectins: sequence-structure-function relationships* Glycobiology (2004) 14(12): 1247-1263; the entire contents of which are incorporated by reference. Based on the knowledge in the art, those of skill in the art will be able to ascertain whether a protein domain is a β-prism lectin domain and whether a protein comprises a β-prism lectin domain. Methods and algorithms for protein domain analysis and alignment are well known to those of skill in the art, and the disclosure is not limited in this respect.

The term FG-GAP domain is used interchangeably with the term FG-GAP repeat, and refers to an extracellular repeat that is found in up to seven copies in alpha integrins. The FG-GAP repeat has been predicted to fold into a beta propeller structure, and is called the FG-GAP repeat after two conserved motifs in the repeat. FG-GAP repeats are found in the N terminus of integrin alpha chains, a region that has been shown to be important for ligand binding. A putative $Ca^{2+}$ binding motif is found in some of the repeats. Representative sequences and consensus sequences of β-prism lectin domains are well known to those of skill in the art. See, e.g., Springer T A et al., Proc Natl Acad Sci USA 1997; 94:65-72. Folding of the N-terminal, ligand-binding region of integrin alpha-subunits into a beta-propeller domain; and Loftus J C, Smith J W, Ginsberg M H; J Biol Chem 1994; 269:25235-25238: Integrin-mediated cell adhesion: the extracellular face; the entire contents of each of which are incorporated herein by reference. Based on the knowledge in the art, those of skill in the art will be able to ascertain whether a protein domain is an FG-GAP domain and whether a protein comprises an FG-GAP domain. Methods and algorithms for protein domain analysis and alignment are well known to those of skill in the art, and the disclosure is not limited in this respect.

The term linker refers to a chemical group or a molecule linking two adjacent molecules or moieties, e.g., a binding domain and a cleavage domain of a nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The terms nucleic acid and nucleic acid molecule refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. The terms oligonucleotide and polynucleotide can be used interchangeably to refer to a polymer of nucleotides (e.g., a string of at least three nucleotides). In some embodiments, a nucleic acid encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms nucleic acid, DNA, RNA, and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications' A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term recombinant nucleic acid refers to a nucleic acid molecule that does not occur in nature, but has been engineered, e.g., in that it has been artificially synthesized, or produced from recombining or otherwise altering the nucleotide sequence of a naturally occurring nucleic acid. Suitable nucleic acid synthesis and engineering methods are well known to those of skill in the art.

The terms small molecule refers to an organic compound, whether naturally-occurring or artificially created (e.g., via chemical synthesis) that has a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, small molecules are monomeric organic compounds that have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body. In certain embodiments, the organic molecule is known to bind and/or cleave a nucleic acid. In some embodiments, the organic compound is an enediyne. In some embodiments, the organic compound is an antibiotic drug, for example, an anticancer antibiotic such as dynemicin, neocarzinostatin, calicheamicin, esperamicin, bleomycin, or a derivative thereof.

The term covalent bond refers to a form of chemical bonding that is characterized by the sharing of one or more pairs of electrons between atoms. A covalent bond formed between two reactive moieties may, for example, be an amide bond, an acyl bond, a disulfide bond, an alkyl bond, an ether bond, or an ester bond. A covalent bond formed between two reactive moieties may be, for example, a carbon-carbon bond, a carbon-oxygen bond, a carbon-nitrogen bond, a carbon-sulfur bond, a sulfur-sulfur bond, a carbon-phosphorus bond, a phosphorus-oxygen bond, or a phosphorus-nitrogen bond.

The term non-covalent bond is used interchangeably with the term non-covalent interaction, and refers to a type of interaction between two molecules that does not involve the sharing of electrons between the molecules, but involves variations of electromagnetic, electrostatic, or hydrophobic interactions.

The term enzyme refers to a molecule, for example, a peptide, a protein, or a nucleic acid (for example, a ribozyme or DNAzyme) that catalyzes a chemical reaction. An enzyme may be a biomolecule (a molecule made by a living organism), a derivative of a biomolecule (e.g., a mutated biomolecule, a fragment of a biomolecule, and/or a fusion product of a biomolecule, or fragment thereof, with a second molecule), or an artificially made molecule (e.g., a synthetic protein or nucleic acid). An enzyme may be an oxidoreductase, transferase, polymerase, hydrolase lyase, synthase, isomerase, or ligase. Accordingly, a protease and a nuclease are non-limiting examples of enzymes. In certain embodiments, the enzyme is a protein. In certain embodiments, the enzyme is a nucleic acid. In certain embodiments, the enzyme is an RNA enzyme, also referred as a ribozyme. In certain embodiments, the enzyme is a DNA enzyme, also referred to as a DNAzyme.

The term enzyme substrate refers to a molecule upon which an enzyme acts. An enzyme substrate is bound by an enzyme and transformed into one or more products in a chemical reaction catalyzed by the enzyme. The reaction product or products are usually released from the enzyme. For example, a protease catalyzes the hydrolysis of an amide bond in a protease substrate peptide or protein. The substrate peptide of a protease is generally bound specifically, meaning that only a peptide of a certain amino acid sequence or with a sequence similar to a consensus sequence is bound by the protease and cleaved into two or more fragments in a hydrolysis reaction.

The term binding agent refers to a molecule that binds to another molecule. In some embodiments, the binding is through non-covalent interaction. In some embodiments, the binding is specific, meaning that the binding agent binds only one particular type of molecule, or a narrow class of highly similar molecules with high affinity. Non-limiting examples of binding agents are antibodies, antibody fragments, aptamers, and adnectins. In some embodiments, the term binding agent, refers to a molecule, for example, a protein, nucleic acid, carbohydrate, or small molecule, that binds another molecule, referred to herein as a target molecule, with high affinity, e.g., with a dissociation constant ($K_D$) of less than $10^{-6}$ M, of less than $10^{-7}$ M, of less than $10^{-8}$ M, of less than $10^{-9}$ M, or of less than $10^{-10}$ M. In some embodiments, a binding agent is or comprises a protein, a peptide, an antibody, an antibody fragment, a ligand, a receptor, or a small molecule, that binds to a target molecule with a $K_D$ as specified above. In some embodiments, the binding agent binds to the target molecule with high affinity, e.g. with a $K_D$ of less than $10^{-8}$, of less than $10^{-9}$ M, of less than $10^{-10}$ M, of less than $10^{-11}$ M, or of less than $10^{-12}$ M. In some embodiments, the binding agent binds to the target molecule with high specificity, e.g., in that it does not bind to molecules other than the target molecule with a $K_D$ of less than $10^{-6}$ M, of less than $10^{-7}$ M, or of less than $10^{-8}$ M.

The term antibody refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term antibody encompasses antigen-binding fragments of antibodies (e.g., single chain antibodies; Fab, Fab', and sFab fragments; F(ab')$_2$ fragments; Fd fragments; Fv fragments; single-chain Fv antibodies (scFv); dAb fragments, and nanobodies) as well as complete antibodies.

The VH and VL regions can be further subdivided into regions of hypervariability, termed "complementarity determining regions" ("CDR"), interspersed with regions that are more conserved, termed "framework regions" ("FR"). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

The term antibody fragment refers to any derivative of an antibody which is less than full-length. Preferably, the antibody fragment retains at least a significant portion of the full-length antibody's specific binding ability. Examples of antibody fragments include, but are not limited to, Fab, Fab', F(ab')2, scFv, Fv, dsFv, diabody, single variable domain, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. Single-chain Fvs (scFvs) are recombinant antibody fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. Diabodies are dimeric scFvs. The components of diabodies typically have shorter peptide linkers than most scFvs, and they show a preference for associating as dimers. An Fv fragment is an antibody fragment which consists of one VH and one VL domain held together by non-covalent interactions. The term dsFv is used herein to refer to an Fv with an engineered intermolecular disulfide bond to stabilize the VH-VL pair. An F(ab')2 fragment is an antibody fragment essentially equivalent to that obtained from immunoglobulins (typically IgG) by digestion with an enzyme pepsin at pH 4.0-4.5. The fragment may be recombinantly produced. A Fab' fragment is an antibody fragment essentially equivalent to that obtained by reduction of the disulfide bridge or bridges joining the two heavy chain pieces in the F(ab')2 fragment. The Fab' fragment may be recombinantly produced. A Fab fragment is an antibody fragment essentially equivalent to that obtained by digestion of immunoglobulins (typically IgG) with the enzyme papain. The heavy chain segment of the Fab fragment is the Fd piece.

The term antigen-binding fragment of an antibody refers to one or more antibody fragments that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a monoclonal antibody or monoclonal antibody composition, which refer to a preparation of antibodies or fragments thereof of single molecular composition. The term isotype refers to the antibody class (e.g., IgM or IgG1) that is encoded by heavy chain constant region genes.

The term binding affinity refers to the apparent association constant or $K_A$. The $K_A$ is the reciprocal of the dissociation constant ($K_D$). A binding agent may, for example, have a binding affinity for a particular target molecule that is associated with a $K_D$ of $<10^{-6}$ M, $<10^{-7}$ M, $<10^{-8}$ M, $<10^{-9}$ M, $<10^{-10}$ M, or $<10^{-11}$ M, with lower $K_D$ values being associated with higher affinity. Higher affinity binding of a binding agent to a first target relative to a second target can be indicated by a higher $K_A$ (or a smaller numerical value $K_D$) for binding the first target than the $K_A$ (or numerical value $K_D$) for binding the second target. In such cases, the binding agent specifically binds the first target relative to the second target. Differences in binding affinity (e.g., for specificity or other comparisons) can be at least 1.5, 2, 3, 4, 5, 10, 15, 20, 50, 70, 80, 100, 500, 1000, 10000, 100000, or 1000000-fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound] = N \cdot [Free]/((1/Ka) + [Free]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term epitope refers to the site on a target molecule that is bound by a binding agent (e.g., an antibody such as a Fab or full length antibody). In the case where the target molecule is a protein, the site can be entirely composed of amino acid components, entirely composed of chemical modifications of amino acids of the protein (e.g., glycosyl moieties), or composed of combinations thereof. Overlapping epitopes include at least one common amino acid residue.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In one embodiment, at least 70, 75, 80, 85, 90, 92, 95, or 98% of, or the entire of, the antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term ligand refers to a binding molecule that binds non-covalently to a second binding molecule with high affinity. In some embodiments, a high-affinity bond is characterized by a $K_D<10^{-6}$ M, a $K_D<10^{-7}$ M, a $K_D<10^{-8}$ M, a $K_D<10^{-9}$ M, a $K_D<10^{-10}$ M, a $K_D<10^{-11}$ M, or a $K_D<10^{-12}$ M. In some embodiments, the ligand is a small molecule. In some embodiments, the ligand is a peptide or protein. In some embodiments, the ligand is a nucleic acid.

The term isolated, in the context of a composition refers to a composition that is removed from at least 90% of at least one component of a natural sample from which the isolated composition can be obtained. In some embodiments, compositions produced artificially or engineered are also encompassed within the scope of the term isolated.

The terms therapeutically effective dosage, therapeutically effective amount, or effective amount is an amount that, when administered to a subject, results in a desired clinical effect, e.g., in the vaccination or immunization of a subject, or in an amelioration of a symptom that is clinically manifest in the subject.

The term affinity tag refers to a tag, for example, a peptide tag that is N-terminally or C-terminally fused to a protein, e.g., an exopolysaccharide-associated protein, that binds to a ligand with high affinity and thus allows for the detection and/or isolation of the tagged protein. Affinity tags are well known to those of skill in the art and examples of suitable affinity tags include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. In some embodiments, the tag is a biotin tag or a biotin variant tag, for example, desthiobiotin (DTB). Some affinity tags and methods for the use of affinity tags are described herein and other suitable tags and methods will be apparent to those of skill in the art, e.g., as described in Lichty J J, Malecki J L, Agnew H D, Michelson-Horowitz D J, Tan S. Comparison of affinity tags for protein purification. Protein Expr Purif. 2005; 41:98-105; and Kimple, M. E., and Sondek, J. *Overview of affinity tags for protein purification*. Curr Protoc Protein Sci. 2004 September; Chapter 9:Unit 9.9; the contents of each of which are incorporated in their entirety herein for disclosure of affinity tags and related methods. Those of skill in the art will appreciate that the invention is not limited in this respect.

The term detection agent is used interchangeably with the term detectable label, and refers to a moiety that has at least one element, isotope, or a structural or functional group incorporated that enables detection of a molecule, e.g., a protein or polypeptide, or other entity, to which the detection agent is attached. A detection agent can be directly attached (e.g., via a bond) or can be attached by a tether or linker. A detection agent can also be conjugated to the molecule, e.g., via non-covalent interactions. It will be appreciated that a detection agent may be attached to or incorporated into a molecule, for example, an exopolysaccharide-associated protein, a fusion protein, a polypeptide, or other entity, at any position, but preferably in a manner that does not interfere with the structural or functional characteristics of the molecule, e.g., the binding of the molecule (e.g., a protein) to a binding partner (e.g., an exopolysaccharide). In general, a detection agent can fall into any one (or more) of five classes: a) an agent which contains isotopic moieties, which may be radioactive or heavy isotopes, including, but not limited to, 2H, 3H, 13C, 14C, 15N, 18F, 31P, 32P, 35S, 67Ga, 76Br, 99mTc (Tc-99m), 111In, 123I, 125I, 131I, 153Gd, 169Yb, and 186Re; b) an agent which contains an immune moiety, which may be an antibody or antigen, which may be bound to an enzyme (e.g., such as horseradish peroxidase); c) an agent comprising a colored, luminescent, phosphorescent, or fluorescent moiety (e.g., such as the fluorescent label fluoresceinisothiocyanat (FITC); d) an agent which has one or more photo affinity moieties; and e) an agent which is a ligand for one or more known binding partners (e.g., biotin-streptavidin, His-NiTNAFK506-FKBP). In certain embodiments, a detection agent comprises a radioactive isotope, preferably an isotope which emits detectable particles, such as β particles. In certain embodiments, a detection agent comprises a fluorescent moiety. In certain embodiments, the detection agent comprises a dye, e.g., a fluorescent dye, e.g., fluorescein isothiocyanate, Texas red, rhodamine, Cy3, Cy5, Cy5.5, ALEXA® 647 and derivatives. In certain embodiments, the detection agent comprises a ligand moiety with one or more known binding partners. In certain embodiments, the detection agent comprises biotin. In some embodiments, a detection agent is a fluorescent polypeptide (e.g., GFP or a derivative thereof such as enhanced GFP (EGFP)) or a luciferase (e.g., a firefly, *Renilla*, or *Gaussia* luciferase). It will be appreciated that, in certain embodiments, a detection agent may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, Tag-BFP, mTurquoise, ECFP, Cerulean, TagCFP, mTFPl, mUkGl, mAGl, AcGFPl, TagGFP2, EGFP, mWasabi, EmGFP, TagYPF, EYFP, Topaz, SYFP2, Venus, Citrine, mKO, mK02, mOrange, mOrange2, TagRFP, TagRFP-T, mStrawberry, mRuby, mCherry, mRaspberry, mKate2, mPlum, niNeptune, T-Sapphire, niAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3): 1103-63, 2010 for discussion of GFP and numerous other fluorescent or luminescent proteins. In some embodiments, a detection agent comprises a dark quencher, e.g., a substance that absorbs excitation energy from a fluorophore and dissipates the energy as heat.

The term antigen refers to a molecule or part of a molecule that is bound by the antigen-binding site of an antibody. In some embodiments, an antigen is a molecule or moiety that, when administered to a subject, activates or increases the production of antibodies that specifically bind the antigen. In some embodiments, an antigen is a protein or a polysaccharide. Antigens of pathogens are well known to those of skill in the art and include, but are not limited to parts (coats, capsules, cell walls, flagella, fimbriae, and toxins) of bacteria, viruses, and other microorganisms. A vaccine typically comprises an antigen, and is intentionally administered to a subject to induce an immune response in the recipient subject.

The term adjuvant refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Many adjuvants suitable for use in the context of embodiments of this disclosure are known to those of skill in the art, including, but not limited to, aluminum salts, liposomes, lipopolysaccharide (LPS), molecular cages for antigen, components of bacterial cell walls, endocytosed nucleic acids such as double-stranded RNA (dsRNA), single-stranded DNA (ssDNA), and unmethylated CpG dinucleotide-containing DNA.

The term vaccine refers to a composition that activates or enhances a subject's immune response to an antigen after the vaccine is administered to the subject. In some embodiments, a vaccine typically contains an antigen characteristic for a pathogen, e.g., a pathogenic microorganism, such as a pathogenic bacterium. In some embodiments, a vaccine comprises a weakened (attenuated), inactivated, or killed pathogen. In some embodiments, a vaccine comprises an antigen found on a toxin or a surface protein of a pathogen. In some embodiments, a vaccine stimulates the subject's immune system to recognize the antigen as foreign, and enhances the subject's immune response if the subject is later exposed to the pathogen, whether attenuated, inactivated, killed, or not. Vaccines may be prophylactic, for example, preventing or ameliorating a detrimental effect of a future exposure to a pathogen, or therapeutic, for example, activating the subject's immune response to a pathogen after the subject has been exposed to the pathogen.

The terms immunizing and vaccinating a subject refer to a process of administering an immunogen, typically an antigen formulated into a vaccine, to the subject in an amount effective to increase or activate an immune response against the antigen and, thus, against a pathogen displaying the antigen. In some embodiments, the terms do not require the creation of complete immunity against the pathogen. In some embodiments, the terms encompass a clinically favorable enhancement of an immune response toward the antigen or pathogen. Methods for immunization, including formulation of a vaccine composition and selection of doses, routes of administration and the schedule of administration (e.g. primary dose and one or more booster doses), are well known in the art. In some cases, an evaluation of vaccine compositions can be performed in a subject, e.g., in human subjects. An immune response can, for example, be detected by an increased titer of circulating antibodies or by the presence of enhanced levels of circulating CTLs against bacterial cells bearing the antigen.

The term pharmaceutical composition refers to a composition that can be administrated to a subject in the context of treatment of a disease or disorder. In some embodiments, a pharmaceutical composition comprises an active ingredient, e.g. a nuclease or a nucleic acid encoding a nuclease, and a pharmaceutically acceptable excipient. In some embodiments, a pharmaceutical composition is sterile. In some embodiments, a pharmaceutical composition is free of undesired toxins, undesired allergens, undesired infectious agents, and/or undesired pathogens.

The term effective amount refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term subject refers to an individual organism. In some embodiments, is a mammal, for example, a human, a non-human primate, a mouse, a rat, a cat, a dog, a cattle, a goat, a pig, or a sheep. In some embodiments, the subject is a vertebrate.

The term target site refers to a site to which delivery of a molecule is desired, or that is targeted for delivery of a molecule. In some embodiments, the target site is an organ or a site of disease in a subject. In some embodiments, the target site is the gastrointestinal tract of a subject, e.g., a human. In some embodiments, the target site is the surface of a bioreactor or culture vessel adjacent to a culture medium within the bioreactor or the culture vessel. In some embodiments, the target site is a surface, e.g., a solid surface of a bioreactor or culture vessel that borders on a liquid phase, e.g., a culture medium in the bioreactor or culture vessel, or the surface of a body of water, e.g., a water/air interface.

The term surface, in the context of materials or target sites, refers to the exterior boundary or the outermost layer of a material. A surface typically constitutes the interface of a material with a different material and/or a different phase. For example, a surface may be the exterior boundary of a liquid material, for example, a culture medium in a bioreactor or culture dish, or liquid comprised in a body of water (e.g., a pond, a lake, an ocean), that is in contact with a solid material, e.g., a solid material comprised in the bioreactor or culture vessel, or a gaseous material, e.g., a gaseous phase overlaying the culture medium (e.g., air, oxygen, nitrogen, carbon dioxide, or a controlled mix of different gases (e.g., 5% Oxygen, 5% carbon dioxide, and 90% nitrogen), or overlaying the body of water (e.g., air). In some embodiments, a surface is an air/water interface, e.g., the region in which the outer layer of a body of water meets the outer layer of an adjacent body of air, or any material within 1 μm, 1 mm, 5 mm, 10 cm, 50 cm, 1 m, or 10 m from the air/water interface.

Engineered Exopolysaccharide-Associated Proteins

Some aspects of this disclosure provide engineered exopolysaccharide-associated proteins. Such proteins can embrace, for example, on secreted bacterial proteins that are retained in the bacterial biofilm matrix by association with the biofilm exopolysaccharide scaffold, as previously identified [1], or other exopolysaccharide-associated proteins, for example, as identified herein, or otherwise known to those of skill in the art.

Some aspects of this disclosure provide a composition comprising an exopolysaccharide-associated protein, or an exopolysaccharide-binding fragment thereof; and a heterologous molecule conjugated to the exopolysaccharide-associated protein, or an exopolysaccharide-binding fragment thereof. The exopolysaccharide-associated protein may be any exopolysaccharide-associated protein described herein or known to those of skill in the art. Similarly, the exopolysaccharide-binding fragment may be any such fragment described herein or known to those of skill in the art.

In some embodiments, the exopolysaccharide-associated protein is a secreted protein or an extracytoplasmic protein. In some embodiments, the exopolysaccharide associated protein remains attached to the cell after synthesis and cellular processing, for example, via noncovalent interactions with molecules on the surface of the cell in the case of a secreted protein, or by a tethering of a transmembrane domain to the cell membrane in the case of an extracytoplasmic protein. Accordingly, an engineered exopolysaccharide associated protein is provided herein, also remains attached to the cell after synthesis and cellular processing in such embodiments. In the case of an engineered secreted exopolysaccharide associated protein, the heterologous molecule conjugated to the exopolysaccharide associated protein will typically also be secreted. In the case of an engineered extracytoplasmic exopolysaccharide associated protein, it is preferable that the protein is engineered so that the heterologous molecule conjugated to the exopolysaccharide associated protein protrudes into the extracytoplasmic space after cellular processing of the engineered protein.

In some embodiments, an engineered exopolysaccharide-associated protein, as provided herein, comprises a known exopolysaccharide-associated protein, or fragment thereof, conjugated to a heterologous molecule. In some embodiments, the exopolysaccharide-associated protein is a type I β-prism lectin domain-containing protein, or an exopolysaccharide-binding fragment thereof. For example, in some embodiments, the exopolysaccharide-associated protein is Bap1 (SEQ ID NO: 1), RbmA (SEQ ID NO: 2), RbmC (SEQ ID NO: 3), or HlyA (SEQ ID NO:4). In some embodiments, the exopolysaccharide associated protein is an exopolysaccharide-binding fragment of Bap1 (SEQ ID NO: 1), RbmA (SEQ ID NO: 2), RbmC (SEQ ID NO: 3), or HlyA (SEQ ID NO:4). In some such embodiments, the fragment comprises a type I β-prism lectin domain contained in the respective full-length protein.

Exemplary known exopolysaccharide-associated proteins from V. cholerae are described in Table 1 and Table 2 below. Other exopolysaccharide-associated proteins from other bacteria strains, e.g., from other Vibrio sp. strains, other diarrheal pathogens, other pathogens, and other nonpathogenic organisms or molecules, are also useful according to some aspects of this invention. Homologous exopolysaccharide-associated proteins can be determined by those of skill in the art via homology determinations, e.g., based on sequence alignments. The sequences of some exemplary exopolysaccharide-associated proteins are provided elsewhere herein, including, the sequences of V. cholerae Bap1, RbmA, RbmC, and HlyA. Those of skill in the art will be able to identify homologous sequences in other Vibrio strains, other bacterial strains, and non-bacterial sources based on this sequence information, and will also be able to determine which of the identified proteins bind exopolysaccharides, e.g., based on the identified proteins comprising a polysaccharide-binding domain, such as, for example, a β-prism lectin domain or an FG-GAP domain.

TABLE 1

Secreted proteins identified in preparations of biofilm matrix.

| Genomic Locus | Annotation |
| --- | --- |
| VC0409 | MshA |
| VC0928 | RbmA |
| VC0930 | RbmC |
| VC2142 | FlaB |
| VC2143 | FlaD |
| VC2187 | FlaC |
| VC2188 | FlaA |
| VCA0027 | ChiA-2 |
| VCA0219 | HlyA |
| VCA0865 | HAP |

TABLE 2

Extracytoplasmic proteins of unknown location.

| Genomic Locus | Annotation |
| --- | --- |
| VC0174 | hypothetical |
| VC0430 | immunogenic protein |
| VC0483 | hypothetical |
| VC1101 | hypothetical |
| VC1154 | hypothetical |
| VC1334 | hypothetical |
| VC1384 | hypothetical |
| VC1523 | hypothetical |
| VC1834 | hypothetical |
| VC1853 | hypothetical |
| VC1887 | hypothetical |
| VC1894 | hypothetical |
| VC2168 | hypothetical |
| VC2517 | hypothetical |
| VCA0026 | hypothetical |
| VCA0058 | conserved, hypothetical |
| VCA0144 | immunogenic protein |
| VCA0900 | hypothetical |

Additional exopolysaccharide-associated proteins found in bacterial biofilms are well known to those of skill in the art and include, for example, those described in Oliver-Kozup et al., *The group A streptococcal collagen-like protein-1, Scl1, mediates biofilm formation by targeting the extra domain A-containing variant of cellular fibronectin expressed in wounded tissue*. Mol Microbiol. 2013; 87(3): 672-89; Diggle et al., *The galactophilic lectin, LecA, contributes to biofilm development in Pseudomonas aeruginosa*. Environ Microbiol. 2006 June; 8(6):1095-104; Johansson et al., *Inhibition and dispersion of Pseudomonas aeruginosa biofilms by glycopeptide dendrimers targeting the fucose-specific lectin LecB*. Chem Biol. 2008 Dec. 22; 15(12):1249-57; and Abdian et al., *RapA2 Is a Calcium-binding Lectin Composed of Two Highly Conserved Cadherin-like Domains That Specifically Recognize Rhizobium leguminosarum Acidic Exopolysaccharides*. J Biol Chem. 2013 25; 288(4):2893-904; the entire contents of each of which are incorporated herein by reference.

In some embodiments, an engineered exopolysaccharide-associated protein as provided herein comprises a β-prism lectin domain, or a fragment thereof, or an FG-GAP domain, or fragment thereof. In some embodiments, an exopolysaccharide-associated protein as provided herein comprises a β-prism lectin domain flanked by an FG-GAP domain. For example, in some embodiments, an engineered exopolysaccharide-associated protein provided herein comprises a structure N-[β-prism lectin domain]$_x$-[FG-GAP domain]$_y$-C;

N-[FG-GAP domain]$_n$-[β-prism lectin domain]$_m$-C;

N-[β-prism lectin domain]$_i$-[FG-GAP domain]$_{ii}$-[β-prism lectin domain]$_{iii}$C N-[FG-GAP]$_a$-[β-prism lectin domain]$_b$-[FG-GAP domain]$_c$-C;

wherein N: N-terminus; C: C-terminus; and x, y, n, m, i, ii, iii, a, b, and c representing, independently, an integer between 0 and 25, and preferably an integer between 1 and 10. In some such embodiments, a heterologous molecule is conjugated to either the N terminus or the C terminus of the provided structure. In some embodiments, the β-prism lectin domain and/or the FG-GAP domain comprises or is encoded by a sequence found in or derived from a naturally occurring exopolysaccharide-associated protein, e.g., from RbMC, Bap1, or HlyA, which are described in more detail elsewhere herein. In some such embodiments, the engineered exopolysaccharide-associated protein can be generated by recombinant methods in which the naturally occurring coding sequences are recombined to form their respective structure. In some embodiments, the β-prism lectin domain and/or the FG-GAP domain comprise a non-naturally occurring sequence, for example a sequence determined to be the minimal sequence required for exopolysaccharide binding. In some embodiments, exopolysaccharide binding its binding to a known exopolysaccharide, for example, an N-glycan, with an affinity characterized by a $K_D$ of $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. Some such minimal sequences are provided herein, and others are known to those of skill in the art, will be apparent to those of skill in the art based on the instant disclosure, or can be ascertained by those of skill in the art with no more than routine experimentation. For methods useful for the determination of the binding affinity of an exopolysaccharide-associated proteins or fragments thereof to an exopolysaccharide, see, e.g., Levan et al., *Vibrio cholerae Cytolysin Recognizes the Heptasaccharide Core of Complex N-Glycans with Nanomolar Affinity*. J Mol Biol. 2012 S0022-2836(12)00949-7; the entire contents of which are Incorporated herein by reference.

Both β-prism lectin domain and FG-GAP domain mediate protein adhesion to exopolysaccharides. In some embodiments, the heterologous molecule is conjugated to a fragment of an exopolysaccharide-associated protein that comprises a minimal exopolysaccharide-binding sequence. Exemplary minimal exopolysaccharide-binding sequences are described in more detail elsewhere herein, and additional minimal exopolysaccharide-binding sequences will be apparent to those of skill in the art based on the instant disclosure, or can be ascertained by those of skill in the art with no more than routine next fermentation.

The heterologous molecule may be any molecule that can be conjugated to an exopolysaccharide-associated protein, for example, a protein, a polypeptide, a nucleic acid, a lipid, a polysaccharide, a small molecule, a binding agent, or a detection agent. The heterologous molecule may be conjugated to the exopolysaccharide-associated protein, or fragment thereof, via covalent linkage, for example, direct covalent linkage, or indirectly via a linker. In some embodiments, the linker comprises a cleavage site, for example, a protease cleavage site. Inclusion of a cleavage site allows the controlled release of the heterologous molecule from the exopolysaccharide-associated protein, which is useful, among other instances, for the controlled release of the heterologous molecule from the exopolysaccharide-associated protein, for example, for isolation and/or purification of the heterologous molecule.

In some embodiments, the heterologous molecule comprises a heterologous protein, for example, an enzyme, or an antigen. In some such embodiments, the heterologous protein is fused to the exopolysaccharide-associated protein, or to the exopolysaccharide-binding fragment thereof, thus forming a fusion protein. The methods and compositions for the generation of fusion proteins are well known to those of skill in the art. In general, a fusion protein of an exopolysaccharide associated protein, or fragment thereof, and a heterologous protein can be created by generating a nucleic acid construct encoding both proteins in frame, optionally with a sequence encoding a linker sequence separating both protein-encoding sequences. Typically, such fusion protein encoding nucleic acid constructs are generated by recombinant technologies, which are well known to those of skill in the art. In some embodiments, a nucleic acid encoding a fusion protein, or a fusion protein itself, may also be synthesized de novo. Methods for synthesizing nucleic acids and proteins are also well known to those of skill in the art.

In some embodiments, the heterologous molecule comprises an antigen, for example, an antigen of a pathogen. Antigens, and, in particular, antigens of pathogens, are well known to those of skill in the art. Some antigens that are of particular interest in the context of some aspects of this disclosure, are antigens of diarrheal pathogens. Diarrheal pathogens include, without limitation, *V. cholerae, Salmonella* sp. (e.g., *Salmonella paratyphi*), *Campylobacter* sp. (e.g., *C. jejuni*) enterotoxic and enterophathogenic *E. coli* (e.g., EHEC, EPEC), and Norovirus. Immunogenic proteins and encoding genes or ORFs from various pathogens, including the diarrheal pathogens listed above, are well known to those of skill in the art, and include, without limitation, the antigens described in Adkins et al., *Bacteria and their toxins tamed for immunotherapy*. Curr Pharm Biotechnol. 2012 June; 13(8):1446-73; Nielsen et al., *Identification of immunogenic and virulence-associated Campylobacter jejuni proteins*. Clin Vaccine Immunol. 2012 February; 19(2):113-9; Yang et al., *Screening of the Salmonella paratyphi A CMCC 50973 strain outer membrane proteins for the identification of potential vaccine targets*. Mol Med Report. 2012 January; 5(1):78-83; Harro et al., *A combination vaccine consisting of three live attenuated enterotoxigenic Escherichia coli strains expressing a range of colonization factors and heat-labile toxin subunit B is well tolerated and immunogenic in a placebo-controlled double-blind phase I trial in healthy adults*. Clin Vaccine Immunol. 2011 December; 18(12):2118-27; Vasconcellos et al., *Generation of recombinant bacillus Calmette-Guérin and Mycobacterium smegmatis expressing BfpA and intimin as vaccine vectors against enteropathogenic Escherichia coli*. Vaccine. 2012 Sep. 7; 30(41):5999-6005; and Tan et al., *Norovirus P particle, a novel platform for vaccine development and antibody production*. J Virol. 2011 January; 85(2):753-64; the entire contents of each of which are incorporated herein by reference. Some exemplary antigens suitable as heterologous molecules according to some aspects of this disclosure are provided in Tables 3 and 4 below.

TABLE 3 highly immunogenic ORFs cloned from *Campylobacter jejuni* (see Nielsen et al., *Identification of immunogenic and virulence-associated Campylobacter jejuni proteins*. Clin Vaccine Immunol. 2012 February; 19(2): 113-9, the entire contents of which are incorporated herein by reference).

| ORF (NCTC 11168)[a] | Annotation |
|---|---|
| Cj0014c | Putative integral membrane protein |
| Cj0034c (4) | Putative periplasmic protein |
| Cj0111 (3) | Putative periplasmic protein |
| Cj0203 | Putative transmembrane transport protein |

TABLE 3-continued highly immunogenic ORFs cloned from *Campylobacter jejuni* (see Nielsen et al., *Identification of immunogenic and virulence-associated Campylobacter jejuni proteins*. Clin Vaccine Immunol. 2012 February; 19(2): 113-9, the entire contents of which are incorporated herein by reference).

| ORF (NCTC 11168)[a] | Annotation |
|---|---|
| Cj0383c | ribH, 6,7-dimethyl-8-ribityllumazine synthase |
| Cj0404 (3) | Putative transmembrane protein |
| Cj0408 | frdC, fumerate reductase cytochrome B subunit |
| Cj0477 | rplL, 50S ribosomal protein |
| Cj0525c (3) | pbpB, putative penicillin binding protein |
| Cj0645 (2) | Putative secreted tranglycosylase |
| Cj0774c (5) | ABC transport system ATP binding protein |
| Cj0811 | lpxK, tetrasyldisaccharide 4'-kinase |
| Cj0917c | cstA, carbon starvation protein A homolog |
| Cj0965c | Putative acyl coenzyme A thioester hydrolase |
| Cj1092c | secF, protein export membrane protein |
| Cj1094c | yajC, preprotein translocase subunit |
| Cj1163c (4) | Putative cation transport protein |
| Cj1174 (3) | Putative efflux protein |
| Cj1292 | dcd, dCTP deaminase |
| Cj1364c | fumC, fumerate hydratase |
| Cj1371 (2) | Putative periplasmic protein (vacJ homolog) |
| Cj1382c (4) | fldA, flavodoxin |
| Cj1529c (5) | purM, phosphoribosylaminoimidazole synthase |
| Cj1628 | exbB2, putative exbB/tolQ family transport protein |
| Cj1632c | Putative periplasmic protein |

TABLE 4 immunogenic proteins from *Salmonella paratyphi* (from Yang et al., *Screening of the Salmonella paratyphi A CMCC 50973 strain outer membrane proteins for the identification of potential vaccine targets*. Mol Med Report. 2012 January; 5(1): 78-83, the entire contents of which are incorporated herein by reference).

| NCBI GI identifier | Mass (Da) | pI (calc) | Protein | Gene |
|---|---|---|---|---|
| 56416031 | 50640 | 4.87 | Maltoporin precursor | LamB |
| 56415127 | 553649 | 5.43 | Outer membrane channel precursor protein | tolC |
| 56412835 | 41214 | 4.63 | Outer membrane protein C | ompC |
| 56412712 | 47675 | 4.90 | Long-chain fatty acid transport protein precursor | fadL |
| 56415967 | 68470 | 5.40 | Vitamin B12 receptor protein | btuB |
| 56412364 | 89861 | 5.30 | Organic solvent tolerance protein | imp |
| 56413481 | 39655 | 4.66 | New outer membrane protein: predicted bacterial porin | nmpC |
| 56413763 | 20090 | 6.28 | Outer membrane invasion protein | pagC |
| 56413343 | 22990 | 5.64 | Putative outer membrane protein | ompW |
| 56413933 | 37583 | 5.47 | Outer membrane protein A | OmpA |
| 56413728 | 28035 | 5.51 | Putative outer membrane protein | mipA |
| 56414068 | 18540 | 5.74 | Outer membrane protein x precursor | OmpX |

In some embodiments, the heterologous molecule is a bacterial toxin, for example, *Bordetella pertussis* adenylate cyclase toxin, *Bacillus anthracis* lethal and edema toxins, *Shigella dysenteriae* shiga toxin, *Escherichia coli* shiga-like toxin, *E. coli* α-hemolysin, *Vibrio cholerae* cholera toxin (e.g., cholera toxin B), *E. coli* heat-labile enterotoxin, *Bordetella pertussis* pertussis toxin, *Bacillus thuringiensis* Cry1A protein, *Clostridium perfringens* perfringolysin O, *Streptococcus intermedius* intermedilysin, *Streptococcus pneumoniae* pneumolysin, *Corynebacterium diphtheriae* diphtheria toxin, or a *Pseudomonas aeruginosa* exotoxin A-based immunotoxin. Bacterial toxins are well known to those of skill in the art, and while some exemplary suitable bacterial toxins are disclosed herein, this disclosure is not limited in this respect. Additional suitable toxins will be apparent to the skilled artisan based on the instant disclosure and the knowledge in the art, including, but not limited to, the toxins described in Adkins et al., *Bacteria and their toxins tamed for immunotherapy*. Curr Pharm Biotechnol. 2012 June; 13(8):1446-73, the entire contents of which are incorporated herein by reference.

In some embodiments, the heterologous molecule comprises an enzyme. Engineered exopolysaccharide-associated proteins comprising enzymes are useful for the generation of bacteria in biofilms that exhibits novel or increased enzymatic activities. Suitable enzymes for some embodiments of this disclosure, for example, oxidoreductases, transferases, polymerases, hydrolases, lyases, synthases, isomerases, and ligases. In some embodiments, the enzyme is a protein that is conjugated to the exopolysaccharide-associated protein by a covalent bond, thus forming a fusion protein. In certain embodiments, however, the enzyme is a non-protein enzyme, for example, a nucleic acid (e.g., a ribozyme or a DNAzyme). In some embodiments, the enzyme is a therapeutic enzyme. Therapeutic enzymes are well known to those of skill in the art and include, for example, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, or alginase. In some embodiments, an engineered exopolysaccharide-associated protein is provided that comprises an exopolysaccharide-associated protein conjugated to a digestive enzyme expressed in the mammalian digestive tract. Suitable digestive enzymes for conjugation to exopolysaccharide-associated proteins include, but are not limited to, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases. Enzymes that are particularly suitable as heterologous molecules in some embodiments of this disclosure are enzymes expressed throughout the lining of the small intestine, which are also referred to sometimes as "brush border enzymes." This brush border enzymes include, but are not limited to the disaccharidases listed above. Other suitable digestive enzymes that can be used according to some aspects of the instant disclosure will be apparent to those of skill in the art and the disclosure is not limited in this respect.

Engineered exopolysaccharide-associated proteins comprising a therapeutic enzyme as the heterologous molecule are useful for various therapeutic applications. For example, such engineered proteins allow the targeted delivery of digestive enzymes to specific target sites within the gastrointestinal tract. For example, an engineered exopolysaccharide-associated protein comprising an exopolysaccharide-associated protein that binds to the biofilm matrix in the small intestine may be conjugated to a digestive enzyme catalyzing a digestive reaction taking place in the small intestine. The engineered protein, or a bacterium expressing the engineer protein, may then be administered to a subject having a deficiency in the respective digestive enzyme. For example, a bacterium expressing a fusion protein of exopolysaccharide associated protein and the digestive enzyme lactase may be administered to a subject with a lactose intolerance to improve lactose digestion and the small intestine.

Importantly, this disclosure is not limited to embodiments of enzyme replacement, but the technology disclosed herein can also be used to transfer entirely new functionalities to biofilms, for example biofilms within the gastrointestinal tract. For example, engineered exopolysaccharide-associated proteins comprising a digestive enzyme not naturally occurring in the intestinal tract of a subject, for example, cellulase, maybe deliberate to the gastrointestinal tract of the subject to enable the subject to digest a previously unknown digestible food source, in this case, cellulose. In an exemplary embodiment, a human subject may be administered a bacterium that can colonize the gastrointestinal tract of the subject, and that expresses an engineered exopolysaccharide-associated protein fused to a cellulase. Upon colonization of the gastrointestinal tract of the subject with the engineered bacteria, the subject will be able to digest cellulose. In preferred embodiments, the bacterium and/or the exopolysaccharide-associated protein are present, and their non-modified form, in the intestinal tract of the subject.

In some embodiments, the heterologous molecule comprises an enzyme that can digest an environmental pollutant. Engineered exopolysaccharide-associated proteins comprising such enzymes allow for the generation of engineered bacteria and biofilms that can help in the cleanup of environmental pollutants. For example, in some embodiments, the heterologous molecule comprises an enzyme that can digest mineral oil contaminations in the environment, for example, in the form of an oil spill into the ocean. Such enzymes include, for example, alkane 1-monooxygenase, naphthalene 1,2-dioxygenase, E-phenylitaconyl-CoA hydratase, benzylsuccinyl-CoA dehydrogenase, methane monooxygenase. In some embodiments, the heterologous molecule comprises an enzyme that protects a bacterium from detrimental effects of an environmental pollutant, or that catalyzes a reaction that increases the capability of a bacterium to break down an environmental pollutant. Such enzymes may include, in some embodiments, enzymes that catalyze sulfite, phosphorus, or iron reduction, or enzymes that confer metal resistance to a bacterium. Such enzymes include, without limitation, sulfite reductases, exopolyphosphatases, and metal reductases. The structure and sequence of many enzymes that can digest or help in the digestion of environmental pollutants, or confer protection against environmental pollutants, are well known to those of skill in the art. Such enzymes include, for example, those described in Hazen et al., *Deep-sea oil plume enriches indigenous oil-degrading bacteria*. Science. 2010 Oct. 8; 330(6001):204-8, including supplemental content (see, e.g., Table S6 of Hazen et al.); Lu et al., *Microbial gene functions enriched in the Deepwater Horizon deep-sea oil plume*. ISME J. 2012 February; 6(2):451-60; Kostka et al., *Hydrocarbon-degrading bacteria and the bacterial community response in gulf of Mexico beach sands impacted by the deepwater horizon oil spill*. Appl Environ Microbiol. 2011 November; 77(22): 7962-74; and Wood et al., *Engineering biofilm formation and dispersal. Trends Biotechnol*. 2011 February; 29(2):87-94; the entire contents of each of which are incorporated herein by reference.

In some embodiments, the heterologous molecule comprises a binding agent. Engineered exopolysaccharide-associated proteins comprising a binding agent are useful for the generation of bacteria and biofilms that exhibits novel or improved binding capabilities. In some embodiments, In some embodiments, this allows for the specific delivery of bacteria or biofilms to a target site of interest, which may be, for example an abiotic surface, such as the surface of a bioreactor, a solid support, a liquid-gas interface, the surface of an environmental pollutant, a biotic surface, e.g., the surface of a living cell or tissue, for example, of a cell or tissue exhibiting a structural or functional deficiency, or a diseased cell or tissue, or a specific region within the gastrointestinal tract. Suitable binding agents are well known to those of skill in the art, and include, but are not limited to, antibodies and antibody fragments. For the preparation of fusion proteins comprising an exopolysaccharide-associated protein and a binding agent specifically binding to antigen, single chain antibodies, such as nanobodies and scFvs are particularly useful. In some embodiments, the binding agent is an adnectin, a lectin, a ligand, or an affinity tag. In embodiments, where an engineered bacterium or an engineered by of time is to be targeted to a specific target site, the binding agent is chosen to bind a molecule or moiety present at the target site. Accordingly, the nature and specificity of the binding agent will depend on the nature and structural characteristics of the target site. For example, in embodiments where an engineered bacterium expressing the fusion protein comprising an exopolysaccharide-associated protein and an antigen-binding antibody fragment is to be delivered to a specific cell or tissue, the binding agent will be chosen to bind an antigen expressed on the surface of the respective cell or tissue.

In some embodiments, the heterologous molecule comprises a detection agent. The generation of engineered exopolysaccharide-associated proteins comprising a detection agent is useful for the detection of engineered bacteria or engineered biofilms expressing such an engineered protein. While any detection agent that can be conjugated to an exopolysaccharide-associated protein, or an exopolysaccharide-binding fragment thereof, is suitable, the use of detectable proteins, e.g., a fluorescent proteins, allows for the generation of fusion proteins comprising an exopolysaccharide-associated protein, or fragment thereof and the detectable protein. The use of detection agents, such as fluorescent proteins or affinity tags, is preferable in some embodiments, because the respective fusion proteins with exopolysaccharide-associated proteins or fragments thereof can easily be expressed in a host cell, e.g., a bacterial cell.

In some embodiments, the compositions further comprises a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion. In some embodiments, the exopolysaccharide-associated protein or fragment thereof that is conjugated to the heterologous molecule comprises an endogenous signal peptide that is retained in the engineered protein, e.g., an engineered fusion protein comprising the respective exopolysaccharide-associated protein or fragment thereof fused to a heterologous protein. In particular, secreted exopolysaccharide-associated proteins comprise such signal peptides in their native sequences. In other embodiments, a heterologous signal peptide is fused to the engineered exopolysaccharide-associated protein, for example, at the N-terminus of the respective fusion protein. Suitable signal peptide sequences for expression of secreted proteins in bacteria are well known to those of skill in the art. Some exemplary signal peptides are described herein, and additional suitable signal peptide will be apparent to the skilled artisan based on the instant disclosure. The disclosure is not limited in this respect. Exemplary fusion proteins according to some aspects of this invention comprise a structure according to the general formula [signal peptide]-[exopolysaccharide-associated protein (or fragment)]-[heterologous molecule], wherein the hyphens represent a peptide bond or a linker. Methods and strategies for preparing such fusion proteins will be apparent to those of skill in the art in view of this disclosure, and exemplary suitable strategies for generating such fusion proteins are described in Absalon et al., The Bacterial Biofilm Matrix as a Platform for Protein Delivery. mBio 3(4): e00127-12, the entire contents of which are incorporated herein by reference.

Engineered Bacteria and Biofilms

Some aspects of this disclosure provide bacteria and biofilms comprising, or associated with, engineered exopolysaccharide-associated proteins. Some aspects of this disclosure provide a composition comprising a bacterium associated with an exopolysaccharide; an exopolysaccharide-associated protein, or an exopolysaccharide-binding fragment thereof; and a heterologous molecule conjugated to the exopolysaccharide-associated protein, or an exopolysaccharide-binding fragment thereof. For example, some aspects of this disclosure provide a bacterium associated with an exopolysaccharide, wherein the bacterium expresses or is associated with an engineered exopolysaccharide-associated protein, e.g., an exopolysaccharide-associated protein or an exopolysaccharide-binding fragment thereof conjugated to a heterologous molecule. In some embodiments, the bacterium expresses the engineered exopolysaccharide-associated protein, for example, from an expression construct encoding the engineered protein that is comprised within the bacterium, e.g., in the form of an expression vector, such as a plasmid. In some embodiments, a bacterium may be contacted with an isolated engineered exopolysaccharide-associated protein under conditions suitable for the protein to associate with the bacterium. In some embodiments, it is advantageous to express the engineered exopolysaccharide-associated protein from an expression vector within the bacterium, because this allows for constant or inducible production of the engineered exopolysaccharide-associated protein, which, in turn, circumvents the need for exogenous replacement of protein over time. This is particularly useful in embodiments where a bacterium is used to deliver a heterologous protein to a target site, e.g., to deliver a digestive enzyme to a cell, tissue, organ, or environmental target site. In such cases, a bacterium expressing the engineered exopolysaccharide-associated protein can, once at the target site, proliferate and replenish the engineered exopolysaccharide-associated protein, either continually or upon exposure to a molecular or environmental cue.

In some embodiments, an engineered exopolysaccharide-associated protein or exopolysaccharide-associated protein fragment described herein is expressed in a bacterium, for example, by contacting the bacterium with an expression construct encoding the engineered exopolysaccharide-associated protein or exopolysaccharide-associated protein fragment. Expression of such engineered proteins in bacteria will confer the engineered characteristics, e.g., engineered structural or functional characteristics, to the expressing bacteria. For example, if an engineered exopolysaccharide-associated protein or protein fragment comprising a fusion protein of an exopolysaccharide-associated protein and a digestive enzyme, e.g., lactase, is expressed in a bacterium, the bacterium will retain the fusion protein on its surface, and thus display lactase functionality. In some embodiments, the expression of an engineered exopolysaccharide-associated protein in a bacterium confers a structural or functional characteristic upon the bacterium that was not natively present in the bacterium, e.g., in the case of expression of the lactase-comprising fusion protein described above in a lactase-deficient bacterium. If such a bacterium can ferment the products of lactase digestion, the acquisition of lactase functionality will result in the bacterium being able to utilize lactose as a food source. Similarly, if the bacterium colonizes a site together with other bacteria that can ferment the products of lactase digestion, but cannot ferment lactose, the bacterial community can now utilize lactose as a food source. The same principle applies to other digestive enzymes, e.g., cellulases, amylases, disaccharidases, oil-degrading enzymes, and so forth.

The engineered exopolysaccharide-associated protein expressed by or contacted with the bacteria can be any engineered exopolysaccharide-associated protein provided herein, e.g., an engineered exopolysaccharide-associated protein comprising a heterologous protein, enzyme, antigen, binding agent, detection agent, small molecule, and so forth; an engineered exopolysaccharide-associated protein comprising an exopolysaccharide-associated protein or exopolysaccharide-binding fragment thereof, as described herein, e.g., as described in Table 1 or 2.

In some embodiments, the engineered bacterium can be any bacterium that can express an engineered exopolysaccharide-associated protein is suitable for use according to some aspects of this disclosure. In some embodiments, the bacterium is In some embodiments, the bacterium is a gram-negative bacterium. In some embodiments, the bacterium is a gram-positive bacterium. Gram-positive and gram-negative bacteria are well known to those of skill in the art. In addition, whether or not a bacterium is gram-positive or gram-negative can easily be determined without more than routine experimentation, e.g., by performing a routine gram staining procedure. In some embodiments, the bacterium is a non-pathogenic bacterium. The use of non-pathogenic bacteria is particularly useful in embodiments that include the delivery of a therapeutic heterologous molecule to a subject, and also in embodiments related to bioremediation, e.g., in embodiments that involve the cleanup of an environmental pollutant. In some embodiments, the bacterium is a pathogenic bacterium. The use of pathogenic bacteria is of particular use in some embodiments that involve or are related to the induction of an immune response, e.g., in embodiments involving the generation of a vaccine or a vaccination of a subject. Non-pathogenic and pathogenic bacteria are well known to those of skill in the art. Exemplary, non-limiting bacterial taxa, species, and strains, suitable for use in some embodiments of this disclosure, e.g., suitable for contacting with or for expression of an engineered exopolysaccharide-associated protein disclosed herein, are provided herein and include, without limitation, *Escherichia* sp., *Enterobacter* sp. (e.g., *Enterobacter cloacae*), *Salmonella* sp. (e.g., *Salmonella enteritidis, Salmonella typhi*), *Shigella* sp., *Pseudomonas* sp. (e.g., *Pseudomonas aeruginosa, Pseudomonas pachastrellae, Pseudomonas stutzeri*), *Moraxella* sp. (e.g., *Moraxella catarrhalis*), *Neisseria* sp. (e.g., *Neisseria gonorrhoeae, Neisseria meningitidis*), *Helicobacter* sp., (e.g., *Helicobacter pylori*) *Stenotrophomonas* sp., *Vibrio* sp. (e.g., *Vibrio cholerae*), *Legionella* sp. (*Legionella pneumophila*), *Hemophilus* sp. (e.g., *Hemophilus influenzae*), *Klebsiella* sp. (e.g., *Klebsiella pneumoniae*), *Proteus* sp. (e.g., *Proteus mirabilis*), *Serratia* sp. (*Serratia marcescens*), *Streptococcus* sp., *Staphylococcus* sp., *Corynebacterium* sp., *Listeria* sp., and *Clostridium* sp., *Bacillus* sp. (e.g., *Bacillus anthracis*) *Bordetella* sp. (e.g., *Bordetella pertussis*); *Borrelia* sp. (e.g., *Borrelia burgdorferi*); *Brucella* sp. (e.g., *Brucella abortus, Brucella canis, Brucella melitensis, Brucella suis*); *Campylobacter* sp. (e.g., *Campylobacter jejuni*); *Chlamydia* sp. and *Chlamydophila* sp. (e.g., *Chlamydia pneumoniae, Chlamydia trachomatis, Chlamydophila psittaci*); *Clostridium* sp. (e.g., *Clostridium botulinum, Clostridium difficile, Clostridium perfringens,* *Clostridium tetani*); *Corynebacterium* sp. (e.g., *Corynebacterium diphtheriae*); *Enterococcus* sp. (e.g., *Enterococcus faecalis, Enterococcus faecium*); *Escherichia* sp. (e.g., *Escherichia coli*, Enterotoxic *E. coli*, enteropathogenic *E. coli; E. coli* O157:H7); *Francisella* sp. (e.g., *Francisella tularensis*); *Haemophilus* sp. (e.g., *Haemophilus influenzae*); *Helicobacter* sp. (e.g., *Helicobacter pylori*); *Legionella* sp. (e.g., *Legionella pneumophila*); *Leptospira* sp. (e.g., *Leptospira interrogans*); *Listeria* sp. (e.g., *Listeria monocytogenes*); *Mycobacterium* sp. (e.g., *Mycobacterium leprae, Mycobacterium tuberculosis, Mycobacterium ulcerans*); *Mycoplasma* sp. (e.g., *Mycoplasma pneumoniae*); *Neisseria* sp. (e.g., *Neisseria gonorrhoeae, Neisseria meningitidis*); *Pseudomonas* sp. (e.g., *Pseudomonas aeruginosa*); *Rickettsia* sp. (e.g., *Rickettsia rickettsii*); *Salmonella* sp. (e.g., *Salmonella typhi, Salmonella typhimurium*); *Shigella* sp. (e.g., *Shigella sonnei*); *Staphylococcus* sp. (e.g., *Staphylococcus aureus, Staphylococcus epidermidis, Staphylococcus saprophyticus*); *Streptococcus* sp. (e.g., *Streptococcus agalactiae, Streptococcus pneumoniae, Streptococcus pyogenes*); *Treponema* sp. (e.g., *Treponema pallidum*); *Pseudodiomarina* sp. (e.g., *P. maritima*); *Marinobacter* sp. (e.g., *Marinobacter hydrocarbonoclasticus, Marinobacter vinifirmus*) *Alcanivorax* sp. (e.g., *alcanivorax dieselolei*); *Acetinobacter* sp. (e.g., *A. venetianus*); *Halomonas* sp. (e.g., *H. shengliensis*); *Labrenzia* sp.; *Microbulifer* sp. (e.g., *M. schleiferi*); *Shewanella* sp. (e.g., *S. algae*); *Vibrio* sp. (e.g., *Vibrio cholerae, Vibrio alginolyticus, Vibrio hepatarius*); and *Yersinia* sp. (e.g., *Yersinia pestis*). In some embodiments, the bacterium is a *Vibrio* sp. bacterium. In some embodiments, the bacterium is a *Vibrio cholerae* bacterium. In some embodiments, the bacterium is an *E. coli* bacterium. Other bacterial taxa and strains that are suitable in embodiments of this disclosure will be apparent to those of skill in the art.

Some aspects of this disclosure provide a bacterial biofilm comprising an engineered bacterium as described herein, for example, a bacterium associated with an exopolysaccharide that is bound by an exopolysaccharide-associated protein (or an exopolysaccharide-binding fragment thereof) conjugated to a heterologous molecule. Depending on the structure and function of the heterologous molecule, such engineered biofilms exhibit novel functional or structural characteristics as compared to the native, non-engineered biofilms.

For example, if the heterologous molecule comprises a binding agent and is conjugated to an exopolysaccharide-associated protein, or exopolysaccharide-binding fragment thereof that is expressed at the surface of the biofilm, the biofilm can bind to a molecule or surface comprising a moiety bound by the binding agent. This allows the engineering of bacterial biofilms to bind to, e.g., surfaces that the respective native biofilm cannot or does not bind to. For another example, if the heterologous molecule comprises a an enzyme and is conjugated to an exopolysaccharide-associated protein, or exopolysaccharide-binding fragment thereof that is expressed at the surface of the biofilm, the biofilm will be able to digest the substrate of the enzyme, e.g., a substrate that was previously inaccessible to the bacteria within the biofilm, or an environmental pollutant.

In some embodiments, an engineered biofilm comprises a combination of engineered exopolysaccharide-associated proteins, e.g., an engineered protein in which the heterologous molecule is a binding agent and an engineered protein in which the heterologous molecule is an enzyme, allowing targeted delivery of the enzyme to a surface bound by the binding agent. In some embodiments, the biofilm comprises a detection agent, e.g., as part of an engineered exopolysaccharide-associated protein expressed by bacteria comprised in the biofilm. This allows the engineering of bacterial biofilms that can be detected, e.g., when bound to a surface, for example, if the detection agent is a fluorescent agent, by fluorescent imaging.

Vaccines

Some aspects of this disclosure provide that engineered exopolysaccharide-associated proteins, as provided herein, are useful for the generation of vaccines. A vaccine typically comprises an agent that mimics or comprises an antigen of a pathogen and, when administered to the subject, and uses an immune response in the subject. When subsequently exposed to the real pathogen, the subject's vaccine-primed immune system is able to recognize and destroy the pathogen with increased efficiency as compared to the immune system of a non-vaccinated subject.

Some aspects of this disclosure provide vaccines that comprise engineered exopolysaccharide-associated proteins that are conjugated to an antigen. In some embodiments, this disclosure provides vaccines that comprise a bacterium associated with an exopolysaccharide; an exopolysaccharide-associated protein, or an exopolysaccharide-binding fragment thereof, that binds the exopolysaccharide; and an antigen conjugated to the exopolysaccharide-associated protein, or an exopolysaccharide-binding fragment thereof. In some such embodiments, the bacterium expresses the engineered exopolysaccharide-associated protein. In some embodiments, the vaccines provided herein are advantageous over currently available vaccines, in that they are easier and cheaper to produce, particularly in a resource-poor setting.

For example, one licensed cholera vaccine comprises killed whole *V. cholerae* bacterial cells combined with the purified B subunit of cholera toxin (CtxB), which serves as both an antigen and an adjuvant [7]. While the purified CtxB component improves short term protection, its production and isolation is cost-intensive, and the use of isolated CtxB negatively affects ease of delivery of the vaccine. As a result, cholera vaccines manufactured in resource-poor settings typically omit this component [8,9], resulting in less-than-optimal vaccinations.

Some aspects of this invention provide an engineered vaccine, for example, an engineered *V. cholerae* vaccine, in which an engineered exopolysaccharide-associated protein conjugated to an antigen or adjuvant is expressed in a bacterial cell, resulting in a decoration of the bacterial cell's exopolysaccharide with the antigen or adjuvant. In some such embodiments, the bacterium comprises a recombinant nucleic acid encoding the engineered exopolysaccharide-associated protein conjugated to the antigen or adjuvant.

For example, in some embodiments, a *V. cholerae* vaccine is provided that comprises a bacterium, for example, a *Vibrio* sp. bacterium (e.g., *V. cholerae*) that expresses an engineered exopolysaccharide-associated protein, e.g., an isolated *V. cholerae* exopolysaccharide-associated protein (e.g., Bap1, RbmA, RbmC, or HlyA), or an exopolysaccharide-binding fragment thereof, conjugated to an antigen or adjuvant, e.g., *V. cholerae* CtxB. One advantage of this type of vaccine over conventional vaccines is its ease of production. Instead of having to grow the bacteria and, separately, having to produce the antigen and/or adjuvant, the bacteria in this type of vaccine express the antigen and/or adjuvant, display it on their surface, and retain it based on the conjugation of the antigen and/or adjuvant to the exopolysaccharide-associated protein. In some embodiments, the antigen and/or adjuvant is a protein or polypeptide that is expressed as a fusion protein with the exopolysaccharide-associated protein, or exopolysaccharide-binding fragment thereof.

As described in more detail in the Examples section, expression of an engineered exopolysaccharide-associated protein comprising CtxB (the B subunit of cholera toxin) as the heterologous agent in *V. cholerae* resulted in a decoration of the bacterial cell's biofilm exopolysaccharide scaffold with CtxB. This integrated decoration avoids the need for a separate production and isolation of CtxB, and could greatly simplify the production and administration of a vaccine including CtxB and also potentially improve vaccine efficacy. In the a proof of principle experiment, wild-type *V. cholerae* was engineered to express an engineered exopolysaccharide-associated protein comprising RbmA with either the CtxB subunit or a FLAG affinity tag fused to its C-terminus. Biofilms were formed with these strains and the RbmA-CtxB fusion protein was observed to be sequestered to the biofilm matrix.

In some embodiments, a vaccine is provided that comprises a bacterium that is not genetically engineered, e.g., wild-type bacterium such as a wild-type *Vibrio* sp. bacterium (e.g., a wild-type *V. cholerae* bacterium), but that is contacted with an isolated engineered exopolysaccharide-associated protein conjugated to an antigen and/or adjuvant, e.g., an isolated *V. cholerae* exopolysaccharide-associated protein (e.g., Bap1, RbmA, RbmC, or HlyA), or an exopolysaccharide-binding fragment thereof, that is conjugated to an antigen or adjuvant, e.g., *V. cholerae* CtxB. In some such embodiments, the engineered exopolysaccharide-associated protein conjugated to the antigen and/or adjuvant can be contacted or combined with the bacterium in a biofilm, and will associate with the exopolysaccharide scaffold of the biofilm. The biofilm can then be dispersed and used for the production of a vaccine. Alternatively, the engineered exopolysaccharide-associated protein conjugated to the antigen and/or adjuvant can be contacted or combined with the bacterium in planktonic form, and will associate with the surface of the bacterium based on the expression of exopolysaccharides on the surface of the bacterium.

The vaccines provided herein, comprising an exopolysaccharide-associated protein, or exopolysaccharide-binding fragment thereof, conjugated to an antigen and/or adjuvant can be produced according to methods of vaccine production known to those of skill in the art. In some embodiments, the bacterium is killed or attenuated, while in other embodiments, the bacterium is alive and/or not attenuated. In some embodiments, the vaccine comprises a pathogenic bacterium, for example, the pathogenic bacterium described herein. In some embodiments, the vaccine comprises a nonpathogenic bacterium, for example a nonpathogenic bacterium as described herein.

In some embodiments, the vaccine comprises a pathogenic bacterium, e.g., a pathogenic *Vibrio* sp. bacterium, such as *Vibrio cholerae* or *Vibrio haemolyticus*, and an engineered exopolysaccharide associated protein comprising an antigen expressed by the pathogenic bacterium as the heterologous molecule. In some embodiments, the vaccine comprises a nonpathogenic bacterium and engineered exopolysaccharide-associated protein comprising an antigen expressed by a pathogenic bacterium as the heterologous molecule. For example, in some embodiments, the vaccine comprises a nonpathogenic *Vibrio* sp. strain, such as *Vibrio alginolyticus, Vibrio harveyi, Vibrio anguillarum*, or *Vibrio fluvialis*, and an engineered exopolysaccharide associated protein comprising an antigen expressed by a pathogenic bacterium, e.g., *Vibrio cholerae* or *Vibrio haemolyticus*, as the heterologous molecule. In some embodiments, the antigen expressed by a pathogenic bacterium is *Vibrio cholerae* CtxB.

In some embodiments, the exopolysaccharide-associated protein, or exopolysaccharide-binding fragment thereof, is fused to the antigen and/or adjuvant, thus forming a fusion protein. In some embodiments, the fusion protein is expressed by the bacterium, e.g., from a recombinant nucleic acid construct. In some embodiments, the exopolysaccharide-associated protein, or exopolysaccharide-binding fragment thereof that is conjugated to the antigen and/or adjuvant comprises a β-prism lectin domain and/or an FG-GAP domain. For example, in some embodiments, the exopolysaccharide-associated protein, or exopolysaccharide-binding fragment thereof that is conjugated to the antigen and/or adjuvant comprises a β-prism lectin domain flanked on one or both sides by an FG-GAP domain, and/or an FG-GAP domain flanked on one or both sides by a β-prism lectin domain. In some embodiments, the exopolysaccharide-associated protein is Bap1 (SEQ ID NO: 1), RbmA (SEQ ID NO: 2), RbmC (SEQ ID NO:3), or HlyA (SEQ ID NO: 4).

In some embodiments, the vaccine further comprises an adjuvant that is not comprised in the engineered exopolysaccharide-associated protein. Suitable adjuvants are known to those of skill in the art, include, without limitation, any adjuvants that are in use for vaccines known in the art. Exemplary suitable adjuvants include, without limitation, inorganic adjuvants, such as aluminium salts or gels (e.g., aluminium phosphate, aluminium hydroxide), alum, organic adjuvants, such as squalene (e.g., $ASO_3$), QS21, oil-based adjuvants (e.g., MF95), and virosomes (e.g., containing a membrane-bound hemagglutinin and neuraminidase derived from an influenza virus). Other adjuvants that are useful according to some aspects of this disclosure include imidazoquinoline amines, imidazopyridine amines, 6,7-fused cycloalkylimidazopyridine amines, 1,2-bridged imidazoquinoline amines, imiquimod and resiquimod, dsRNA, poly I:C, bacterial lipopolysacharide (LPS), VSV-G, and HMGB-1.

Some aspects of this disclosure provide vaccines that comprise engineered exopolysaccharide-associated proteins that are conjugated to an antigen and that also comprise an adjuvant. Some aspects of this disclosure provide vaccines that comprise engineered exopolysaccharide-associated proteins that are conjugated to an adjuvant. Some aspects of this disclosure provide vaccines that comprise engineered exopolysaccharide-associated proteins that are conjugated to an antigen and an adjuvant. For example, in some embodiments, a vaccine is provided that comprises a fusion protein of the general structure [exopolysaccharide-associated protein (or fragment thereof)]-[antigen] and an adjuvant. In some embodiments, a vaccine is provided that comprises a fusion protein of the general structure [exopolysaccharide-associated protein (or fragment thereof)]-[antigen]-[adjuvant] or [exopolysaccharide-associated protein (or fragment thereof)]-[adjuvant]-[antigen]. In some embodiments, a composition, e.g., a vaccine, is provided that comprises a fusion protein of the general structure [exopolysaccharide-associated protein (or fragment thereof)]-[adjuvant]. In some embodiments, the adjuvant comprises a peptide. For example, in some embodiments, the adjuvant comprises a cholera toxin B peptide, or a fragment thereof. In some embodiments, the adjuvant comprises a host defense peptide, e.g., a host defense peptide or other immuno stimulatory sequence as described in U.S. Patent Application Publication US20100239611, entitled *Combination Adjuvant Formulation*, published on Sep. 23, 2010; or in Hancock et al., *Synthetic peptides as antigens for antibody production*. Methods Mol Biol. 2005; 295:13-26; the entire contents of each of which are incorporated herein by reference. Exemplary suitable peptide adjuvants include, without limitation, ILPWKWPWWPWRR (SEQ ID NO: 13); VFLRRIRVIVIR (SEQ ID NO: 14); VFWRRIRVWVIR (SEQ ID NO: 15); VQLRAIRVRVIR (SEQ ID NO: 16); VQLRRIRVWVIR (SEQ ID NO: 17); VQWRAIRVRVIR (SEQ ID NO: 18); VQWRRIRVWVIR (SEQ ID NO: 19); GRFKRFRKKFK-KLFKKLSPVIPLLHLG (SEQ ID NO: 20); GGL-RSLGRKILRAWKKYGPIIVPIIRIG (SEQ ID NO: 21); RLARIVVIRVAR LLGDFFRKSKEKIG-KEFKRIVQRIKDFLRNLVPRTES (SEQ ID NO: 22); VQLRIRVAVIRA (SEQ ID NO: 23); VQRWLIVWRIRK (SEQ ID NO: 24); VRLIVAVRIWRR (SEQ ID NO: 25); IWVIWRR (SEQ ID NO: 26); I(Dhb)AI(Dha)LA(Abu)PGAK(Abu)GALMGANMK(Abu)A(Abu)ANASINV(Dha)L (SEQ ID NO: 27, Dhb: dehydrobutyrine, Dha: dehydroalanine, Abu: 2-aminobutyric acid); VXXRXIRVX-VIR (SEQ ID NO: 28); ILKWKWPWWPWRR (SEQ ID NO: 29); ILPWKKPWWPWRR (SEQ ID NO: 30); ILK-WKWPWWKWRR (SEQ ID NO: 31); and ILRWKWRW-WRWRR (SEQ ID NO: 32). For example, an exemplary fusion protein may comprise a structure as follows: [RbmA]-[CtxB]-[ILPWKWPWWPWRR (SEQ ID NO: 33)] or [RbmC]-[ILKWKWPWWPWRR (SEQ ID NO: 34)]. These two examples are merely to illustrate possible structures of fusion proteins provided herein, but are not limiting, as additional suitable combinations of exopolysaccharide-associated proteins or exopolysaccharide-binding fragments thereof with antigens and/or peptide adjuvants as provided herein will be apparent to those of skill in the art based on the instant disclosure.

In some embodiments, the vaccine is formulated into a pharmaceutical composition for administration (e.g., orally, intramuscularly, intradermally, or rectally) to a subject. In some embodiments, the vaccine is administered to a subject. Accordingly, some embodiments provide a method of vaccinating a subject against a pathogen. Typically, the method comprises administering to the subject an effective amount of a vaccine described herein. An effective amount, in some embodiments, is an amount that induces an immune reaction in the subject. For example, in some embodiments, an effective amount of a vaccine is an amount that, when administered to a subject, results in a measurable increase in immunity of the subject against a pathogen expressing an antigen comprised in the vaccine. In some embodiments, an effective amount of a vaccine is an amount that, when administered to a subject, results in a measurable immune response in the subject against a pathogen expressing an antigen comprised in the vaccine. For example, a measurable immune response may include an increased number or level of immunoglobulins specifically binding the antigen, or an increased number of immune cells recognizing or producing antibodies directed towards the antigen. In some embodiments, the vaccine is administered in an amount sufficient to elicit an immune response against the bacterium and/or against the antigen. In some embodiments, the vaccine is administered in an amount sufficient to immunize the subject against the bacterium and/or against the antigen. While total immunization against the antigen may be desirable and feasible in some embodiment, partial immunization is also beneficial in many cases. For example, such partial immunization may ameliorate the clinical manifestation of an exposure to a pathogen, e.g., as evident in a shortened period of sickness or a decrease in the symptoms associated with the pathogen, as compared to an average subject within a population or to a non-vaccinated subject.

The inventive vaccines may be administered by a variety of routes of administration, including but not limited to parenteral (such as subcutaneous, intramuscular, intravenous, or intradermal); oral; transnasal, transmucosal, rectal; ophthalmic, or transdermal.

Methods

Some aspects of this disclosure provide methods for delivering a molecule to a target site. In some embodiments, the method comprises delivering to the target site a bacterium associated with an exopolysaccharide that binds an exopolysaccharide-associated protein, or an exopolysaccharide-binding fragment thereof, wherein the exopolysaccharide-associated protein, or an exopolysaccharide-binding fragment thereof, binds the molecule. In some embodiments, the molecule is a heterologous molecule. In some embodiments, the molecule is conjugated to the exopolysaccharide-associated protein or the exopolysaccharide-binding fragment thereof, for example, via covalent bond or via non-covalent interaction. In some embodiments, the molecule is bound to the exopolysaccharide-associated protein, or the exopolysaccharide-binding fragment thereof, via a linker, for example via a linker comprising a sequence of immune acids that can be cleaved by a protease. In some embodiments, the molecule comprises a heterologous protein or polypeptide. In some embodiments, the polypeptide is fused to the exopolysaccharide-associated protein or the exopolysaccharide binding protein fragment. In some embodiments, the bacterium being delivered to the target site comprises a recombinant nucleic acid encoding the polypeptide fused to the exopolysaccharide-associated protein or the exopolysaccharide binding protein fragment.

In some embodiments, a method of delivering a protein of interest to a target site is disclosed herein can be used to deliver the protein to a target site that can be colonized by a bacterium expressing a fusion protein comprising the protein of interest and an exopolysaccharide-associated protein, or an exopolysaccharide-binding fragment thereof. In some embodiments, the protein of interest is a heterologous protein in relation to the exopolysaccharide-associated protein, or the exopolysaccharide-binding fragment thereof. In some embodiments, the heterologous protein comprises an antigen, an enzyme, a binding agent, a detection agent, a therapeutic agent, or an antibiotic agent. Any protein comprising an antigen, an enzyme, a binding agent, a detection agent, a therapeutic agent, or antibiotic agent described herein or otherwise known to those of skill in the art that can be fused to a exopolysaccharide-associated protein, or an exopolysaccharide-binding fragment thereof, can be delivered to a target site using the methods provided herein.

In some embodiments, the target site is a site within a subject that can be colonized by the bacterium. For example, in some embodiments, the target site is within the gastrointestinal tract, for example, within the stomach, the duodenum, the small intestine, the cecum, the appendix, or the colon, or within the oral cavity. In some embodiments, the target site is within the respiratory tract of the subject, for example, within the lung, within a primary bronchus, within a secondary bronchus, within a tertiary bronchus, within a bronchiole, within the trachea, or within the larynx. In some such embodiments, the method comprises administering to a subject a bacterium expressing a fusion protein comprising the protein of interest fused to an exopolysaccharide-associated protein or an exopolysaccharide-binding fragment thereof, in an amount sufficient for the bacterium to colonize the respective target site within the subject. In some embodiments, bacterial colonization of the target site refers to bacteria reaching the target site and proliferating and/or persisting at the target site for at least one day, at least two days, at least three days, at least four days, at least five days, at least six days, at least one week, at least two weeks, at least three weeks, at least four weeks, at least one month, at least two months, at least three months, at least four months, at least six months, at least one year, or at least two years.

For example, in some embodiments, a method is provided that comprises administering to a subject having a deficiency in and a digestive enzyme, for example, a lactase deficiency, a nonpathogenic bacterium that is able to colonize the gastrointestinal tract of the subject, for example, the small intestine, and that expresses a fusion protein comprising a digestive enzyme that the subject is deficient in, e.g., lactase, fused to an exopolysaccharide-associated protein or an exopolysaccharide-binding fragment thereof, in an amount sufficient for the bacterium to colonize the small intestines of the subject. In some embodiments, the bacterium is a bacterium that, in wild type form, colonizes the target site, for example the small intestine, of the subject, or is isolated from the target site, for example, from the small intestines, of the subject. In some embodiments, the subject is lactose intolerant, and the enzyme is lactase. In some embodiments, the subject has cystic fibrosis, and the enzyme is a pancreatic enzyme. In some embodiments, the bacterium is administered to the subject in the form of a probiotic. In some embodiments, administration route is oral or rectal.

In some embodiments, a method is provided that comprises administering to a subject having cystic fibrosis a nonpathogenic bacterium that is able to colonize the subject's respiratory tract, for example, the lung, the bronchi, the bronchioles, or the trachea, and that expresses a fusion protein comprising a mucus digesting enzyme, for example, a mucinase or alginase, fused to an exopolysaccharide-associated protein or an exopolysaccharide-binding fragment thereof, in an amount sufficient for the bacterium to colonize the respiratory tract of the subject. In some embodiments, the bacterium is a bacterium that, in wild type form, colonizes the respiratory tract, or part of the respiratory tract of the subject, or is a bacterium that is isolated from the pulmonary airway of a subject. In some embodiments, the bacterium is a nonpathogenic bacterium that can colonize the respiratory tract of a subject. In some embodiments, the bacterium is administered directly to the respiratory tract of the subject, e.g., via an aerosol or an inhalant. In some embodiments, the bacterium is of a nonpathogenic species that is found in the respiratory tract of a healthy subject, e.g., *Prevotella* sp., *Mesorhizobium* sp., *Microbacterium* sp., *Micrococcus* sp., *Veillonela* sp., *Rhizobium* sp., *Stenotrophomonas* sp., or *Lactococcus* sp. In some embodiments, the bacterium is a *Pseudomonas* sp. bacterium. In some embodiments, the bacterium is a nonpathogenic *Pseudomonas* bacterium, e.g., *Pseudomonas chlororaphis* or *Pseudomonas putida*.

In some embodiments, the target site is a surface. In some embodiments, the target site is an abiotic surface. In some embodiments, the surface is a liquid-gas interface, e.g., a water-air interface, or a culture media-air interface, for example, in a body of water, such as an ocean, a lake, or a pond, or in a bioreactor or culture vessel holding liquid media. In some embodiments, the target site is a liquid-solid interface, e.g., a water-soil interface, a water-metal interface, or a water-plastic interface. In some embodiments, the molecule to be delivered to the target site is an enzyme that can digest a substrate present at the target site. In some embodiments, the substrate is a contaminant that is present at the target site. For example, in some embodiments, the target site is a water-air interface and the substrate is an environmental pollutant, such as a toxic chemical or oil, for example, in the context of an oil spill. In some such embodiments, the enzyme expressed as a fusion protein with an exopolysaccharide-associated protein or exopolysaccharide-binding fragment thereof by a bacterium that forms a biofilm. The bacterium is then delivered to the target site, where it expresses the fusion protein and forms or integrates into a biofilm. The biofilm formed retains the fusion protein, and, thus, exhibits the functionality of the fusion protein, here an enzymatic activity directed towards the enzyme's substrate, e.g., a contaminant or an environmental pollutant.

Accordingly, the instantly disclosed technology can be used in the context of bioremediation, referring to the use of bacteria to remove, or aid in the removal of, pollutants from the environment. Engineered bacteria as provided herein can be delivered to sites of contamination and pollution and, through expression of an engineered exopolysaccharide-associated protein, e.g., a fusion protein comprising an enzyme that can break down the pollutant or contaminant.

In some embodiments related to bioremediation, the target site is an environmental surface. For example, in some embodiments, the target site is a polluted water-air interface, a polluted water-soil interface, or a polluted soil-air interface. In some embodiments, the molecule to be delivered to the target site is an enzyme that can break down a pollutant present at the target site. In some such embodiments, the enzyme is expressed as a fusion protein with an exopolysaccharide-associated protein or exopolysaccharide-binding fragment thereof by a bacterium that forms a biofilm. The bacterium is then delivered to the polluted target site, where it expresses the fusion protein and forms or integrates into a biofilm. The biofilm retains the fusion protein, and, thus, exhibits the functionality of the fusion protein, here an enzymatic activity that breaks down the pollutant.

For example, in some embodiments in the context of a marine oil spill, an engineered bacterium expressing an oil-degrading enzyme, e.g., an oil-degrading enzyme as described elsewhere herein, is delivered to the water-air interface of the contaminated body of water, where it proliferates and forms a biofilm expressing the oil-degrading enzyme functionality. Suitable enzymes that are useful in such embodiments include, without limitation, alkane 1-monooxygenase, naphthalene 1,2-dioxygenase, E-phenylitaconyl-CoA hydratase, benzylsuccinyl-CoA dehydrogenase, methane monooxygenase, and the enzymes described in Hazen et al., *Deep-sea oil plume enriches indigenous oil-degrading bacteria*. Science. 2010 Oct. 8; 330(6001):204-8, including supplemental content (see, e.g., Table S6 of Hazen et al.); Lu et al., *Microbial gene functions enriched in the Deepwater Horizon deep-sea oil plume*. ISME J. 2012 February; 6(2):451-60; Kostka et al., *Hydrocarbon-degrading bacteria and the bacterial community response in gulf of Mexico beach sands impacted by the deepwater horizon oil spill*. Appl Environ Microbiol. 2011 November; 77(22): 7962-74; and Wood et al., *Engineering biofilm formation and dispersal*. Trends Biotechnol. 2011 February; 29(2):87-94; the entire contents of each of which are incorporated herein by reference. Suitable bacterial genera and strains that are useful for expressing engineered exopolysaccharide-associated proteins as provided herein in the context of bioremediation scenarios, e.g., in the context of a marine oil spill, are known to those of skill in the art and include, without limitations, the bacterial taxa, genera, species, and strains described in Hazen et al., *Deep-sea oil plume enriches indigenous oil-degrading bacteria*. Science. 2010 Oct. 8; 330(6001):204-8; Kostka et al., *Hydrocarbon-degrading bacteria and the bacterial community response in gulf of Mexico beach sands impacted by the deepwater horizon oil spill*. Appl Environ Microbiol. 2011 November; 77(22):7962-74; and Wood et al., *Engineering biofilm formation and dispersal*. Trends Biotechnol. 2011 February; 29(2):87-94; the entire contents of each of which are incorporated herein by reference. Additional suitable enzymes and bacterial genera will be apparent to those of skill in the art, and the disclosure is not limited in this respect.

In some embodiments related to bioremediation, or otherwise to the release of engineered bacteria into the environment, it is preferable that the bacteria also comprise a safeguard measure that prevents uncontrolled proliferation in the environment. For example, in some embodiments, the bacteria exhibit a dependency on a nutrient that does not exist or is extremely rare in the environment. This nutrient can be dispersed at the target site, e.g., at the water-air interface affected by a marine oil spill, to allow the bacteria to survive, proliferate, and form biofilms. Once the bioremediation task is done, dispersal of the nutrient is discontinued, resulting in the death of the released bacteria. In some embodiments, the bacteria used are auxotrophs that require a nutrient not typically found at the site of release, or the environment exposed to the bacteria, for example, an amino acid (e.g., histidine), a vitamin (e.g., biotin), or a cell wall component (e.g., diaminopimelic acid).

Some aspects of this disclosure provide methods for using an engineered exopolysaccharide-associated protein, an engineered bacterium, or an engineered biofilm as provided herein for the purification of a product generated in a cell culture or in a bioreactor. In some such embodiments, engineered bacteria or biofilms function as a biocolumn, retaining and/or concentrating the product on their cell surface or within the biofilm. The bacteria or the biofilm can then be retrieved and the product isolated from the bacteria or the biofilm. The use of engineered bacteria or biofilms as provided herein as biocolumns is advantageous as compared to conventional strategies. Such conventional strategies typically rely on the desired product of a biofermentation being secreted by cells within a bioreactor into a liquid medium, separation of the cells from the liquid medium, and isolation of the product from the liquid medium. In many instances, this strategy required the processing of large amounts of liquid medium containing small amounts of the desired product. If the product is soluble, the subsequent isolation typically requires the use of binding agents conjugated to a solid support or the precipitation of the product from the liquid media.

In contrast, the methods for purifying a product from a bioreactor by using the engineered cells or biofilms provided herein as biocolumns allow for the separation of the product via a method that includes separating the bacteria or the biofilm from the liquid media in the bioreactor, and then isolating the product from the bacteria or biofilm. This obviates the use of binding agents for the isolation of the product from liquid media, and allows for a one-step purification method.

For example, in some embodiments, the product is a protein. In some such embodiments, the protein is expressed as a fusion protein with an exopolysaccharide-associated protein, or with an exopolysaccharide-binding fragment thereof. In some embodiments, the method of purifying the protein involves culturing a bacterium expressing the protein as a fusion protein with an exopolysaccharide-associated protein, or with an exopolysaccharide-binding fragment thereof in a liquid medium. In some embodiments, the fusion protein comprises a cleavable linker, e.g., a protease- or photocleavable linker, connecting the product protein to the exopolysaccharide-associated protein or the exopolysaccharide-binding fragment thereof. In some embodiments, the bacteria express the fusion protein. In some embodiments, the protein product is fused to the exopolysaccharide-associated protein or the exopolysaccharide-binding fragment thereof in manner that results in the product protein being located in the extracellular space. In some embodiments, the fusion protein is secreted by the bacteria. In some embodiments, the bacteria are in planktonic form and retain the product protein on their cell surface based on its fusion to an exopolysaccharide-associated protein, or with an exopolysaccharide-binding fragment thereof. In other embodiments, the bacteria form a biofilm and the product protein is retained within the biofilm based on its fusion to an exopolysaccharide-associated protein. In some embodiments, the method includes isolating the bacteria, e.g., by pelleting planktonic bacteria (e.g., by centrifugation), or by retrieving a biofilm from a surface within a bioreactor. In some embodiments, the method further includes separating the protein product from its fusion partner, e.g., the exopolysaccharide-associated protein or the exopolysaccharide-binding fragment thereof, for example, by cleavage of the cleavable linker. In some embodiments, the cleaved-off protein product is then eluted from the bacteria, which will retain the cleaved-off portion of the fusion protein that comprises the exopolysaccharide-associated protein or the exopolysaccharide-binding fragment thereof.

For example, in some embodiments, the product is a secreted molecule. In some such embodiments, the bacteria express the secreted molecule and a fusion protein comprising a protein binding agent that binds the secreted product molecule (e.g., an affinity tag, antibody fragment, adnectin, or aptamer) fused to an exopolysaccharide-associated protein or an exopolysaccharide-binding fragment thereof. In some embodiments, the method of purifying the protein involves culturing a bacterium expressing the secreted product and a protein binding agent that binds the secreted product molecule (e.g., an affinity tag, antibody fragment, adnectin, or aptamer) fused to an exopolysaccharide-associated protein or an exopolysaccharide-binding fragment thereof in a liquid medium. In some embodiments, the fusion protein comprises a cleavable linker, e.g., a protease- or photocleavable linker, connecting the binding agent to the exopolysaccharide-associated protein or the exopolysaccharide-binding fragment thereof. The binding agent in such embodiments is fused to the exopolysaccharide-associated protein or the exopolysaccharide-binding fragment thereof in manner that results in the binding agent being located in the extracellular space. In some embodiments, the fusion protein is secreted by the bacteria. In some embodiments, the bacteria are in planktonic form and retain the binding agent on their cell surface based on its fusion to an exopolysaccharide-associated protein or an exopolysaccharide-binding fragment thereof. In other embodiments, the bacteria form a biofilm and the binding agent is retained within the biofilm based on its fusion to an exopolysaccharide-associated protein or an exopolysaccharide-binding fragment thereof. The bacteria are cultured under conditions that permit the binding agent on the surface of the bacteria or within the biofilm to bind the product molecule. In some embodiments, the method includes isolating the bacteria, e.g., by pelleting planktonic bacteria (e.g., by centrifugation), or by retrieving a biofilm from a surface within a bioreactor. In some embodiments, the method further includes separating the product molecule from the binding agent, e.g., by eluting the product molecule. In some embodiments, the method includes cleaving the binding agent from its fusion partner, e.g., the exopolysaccharide-associated protein or the exopolysaccharide-binding fragment thereof, for example, by cleavage of the cleavable linker. In some embodiments, the cleaved-off binding agent, bound to the product molecule, is then separated from the bacteria, e.g., by elution, and subsequently the product molecule is isolated, e.g., eluted from the binding agent. The nature of the binding agent will depend on the product molecule to be purified. Binding agents for various product molecules are well known to those of skill in the art, and the disclosure is not limited in this respect.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Materials and Methods

Bacterial strains, plasmids, and media. The bacterial strains and plasmids used in this study are listed in Table 5:

TABLE 5 bacterial strains and plasmids. All listed references (Ref.) are incorporated herein by reference in their entirety.

| Bacterial Strains | Genotype and/or phenotype | Ref. |
|---|---|---|
| *E. coli* strains | | |
| SM10λpir | thi thr leu tonA lacY supE recA::RP4-2-Tc::MuλpirR6K;Km$^r$ | [1] |
| *V. cholerae* strains | | |
| PW249 | MO10; Sm$^r$ | [2] |
| PW328 | MO10 ΔvpsL, Sm$^r$ | [3] |
| PW357 | MO10 lacZ::vpsLp→lacZ; Sm$^r$ | [3] |
| PW454 | MO10 ΔvpsL lacZ::gfp; Sm$^r$ | |
| PW707 | MO10 Δbap1ΔrbmC; lacZ::vpsLp→lacZ; Sm$^r$ | |
| PW1085 | MO10 rbmA-flag; lacZ::vpsLp→lacZ; Sm$^r$Ap$^r$ | |
| PW1086 | MO10 bap1-flag; lacZ::vpsLp→lacZ; Sm$^r$Ap$^r$ | |
| PW1087 | MO10 ΔrbmA; lacZ::vpsLp→lacZ; Sm$^r$ | |
| PW1088-90 | MO10 Δbap1ΔrbmC, Sm$^r$ | |

TABLE 5-continued bacterial strains and plasmids. All listed references (Ref.)
are incorporated herein by reference in their entirety.

| Bacterial Strains | Genotype and/or phenotype | Ref. |
|---|---|---|
| Plasmids | | |
| pWM91 | oriR6KmobRP4 lacI pTac tnp miniTn10Km; Ap$^r$ | [4] |
| pWM91Δbap1 | pWM91 carrying a fragment of bap1 harboring an internal, unmarked deletion; Ap$^r$ | [5] |
| pWM91ΔrbmC | pWM91 carrying a fragment of rbmC harboring an internal, unmarked deletion; Ap$^r$ | |
| pWM91ΔrbmA | pWM91 carrying a fragment of rbmA harboring an internal, unmarked deletion; Ap$^r$ | |
| pGP704::bap1-flag | pGP704 carrying 3' end of bap1 fused to a flag tag; Ap$^r$ | |
| pGP704::rbmA-flag | pGP704 carrying 3' end of rbmA fused to a flag tag; Ap$^r$ | |
| pJZ111 | Plac::gfp::lacZ in pCVD442; Ap$^r$ | [6] |
| pBAD-TOPO-rbmA | pBAD-TOPO carrying the gene at locus VC0928 (rbmA); Ap$^r$ | |
| pFLAG-chiA-2 | pFLAG-CTC carrying the gene at locus VCA0027 (chiA-2); Ap$^r$ | |
| pFLAG-hlyA | pFLAG-CTC carrying the gene at locus VCA0219 (hlyA); Ap$^r$ | |
| pFLAG-hapA | pFLAG-CTC carrying the gene at locus VCA0865 (hapA); Ap$^r$ | |
| pFLAG-tcpG | pFLAG-CTC carrying the gene at locus VC0034 (tcpG); Ap$^r$ | |
| pFLAG-mshA | pFLAG-CTC carrying the gene at locus VC0409 (mshA); Ap$^r$ | |
| pFLAG-rbmA | pFLAG-CTC carrying the gene at locus VC0928 (rbmA); Ap$^r$ | |
| pFLAG-crr | pFLAG-CTC carrying the gene at locus VC0964 (crr); Ap$^r$ | |
| pFLAG-bap1 | pFLAG-CTC carrying the gene at locus VC1888 (bap1); Ap$^r$ | |

Vectors used for protein expression included an IPTG inducible promoter driving expression of the protein of interest with a C-terminal FLAGtag (pFLAG-CTC, Sigma-Aldrich). Bacteria were cultivated in Luria-Bertani broth (LB) supplemented with ampicillin (100 µg/ml). Because adequate protein expression was observed without induction, the growth medium was not supplemented with IPTG.

Construction of plasmids for protein expression. The ORFs of interest were amplified by PCR using primers including the start and stop codons of each gene of interest. Kpn I restriction sites were included in the primers used for amplification of chiA-2. These restriction sites were used to insert chiA-2 between rbmA and the FLAG tag in expression vector pFLAG-rbmA [1]. Kpn I and Sal I restriction sites were used to fuse ctxB to the C-terminal end of rbmA pFLAG-rbmA. In this case, the FLAG tag was removed. All insertions were confirmed by sequence analysis. Before use, we confirmed that the RbmA-CtxB and RbmA-ChiA-2-FLAG fusion proteins did not interfere with formation of the wild-type V. cholerae biofilm.

Mutant construction. The V. cholerae Δbap1ΔrbmCΔrbmA mutant was constructed as previously described [14] using the strain V. cholerae Δbap1ΔrbmC mutant (PW707) and the suicide plasmid pWM91ΔrbmA [1].

Biofilm assays. A single colony of V. cholerae was inoculated into 1 ml of LB broth and allowed to grow to mid exponential phase. The culture was then diluted in LB broth to yield an OD$_{655}$ of 0.05 and divided into three disposable glass culture tubes (10 mm×75 mm). These tubes were incubated statically at 27° C. After 24 hrs, planktonic cells were removed, and the OD$_{655}$ of the cells was measured. Remaining biofilms were washed with 0.1 M phosphate-buffered saline solution (PBS) (pH 7.0) and then disrupted with 1 mm beads (Biospec). The OD$_{655}$ of the resulting cell suspension was measured. For assays of biofilm integrity, biofilms were formed as described above in 24 well plates and then vortexed.

Immunofluorescence. Immunofluorescence experiments were performed as previously described with the following modifications [1]. To detect the RbmA-CtxB fusion protein, an anti-CtxB antibody (Sigma) (1:1000 dilution) followed with an ALEXA FLUOR® 488 Goat Anti-Rabbit Antibody (Invitrogen) was used. To detect ChiA-2-FLAG and RbmA-Chia-2-FLAG, an anti-FLAG M2 antibody (1:1000 dilution) (Sigma-Aldrich) was used followed by an incubation with DYLIGHT® 549 AffiniPure Rabbit Anti-Mouse IgG H+L (1:1000 dilution) (Jackson ImmunoResearch). Confocal images were acquired at the Children's Hospital, Boston Imaging Core with a LSM700 microscope (Zeiss) equipped with a 63× objective and 405, 488, and 555 nm laser lines. A computer equipped with ZEN 2009 software was used to acquire and process images.

Chitinase assays. For assays of protein activity, cells were cultured in LB broth supplemented with ampicillin at 27° C. for approximately 5 hours and then back-diluted in the same medium to yield an OD$_{655}$ of 0.05. For assays of activity within the biofilm, three 80 µl aliquots of each culture were transferred to the wells of a 96 well, black microtiter dish and three to wells of a polystyrene 96 well plate. Both plates were incubated statically at 27° C. for 24 hours. The planktonic fractions of the resulting cultures were removed, fractions from one well of the black plate and one well of the polystyrene plate were pooled, an OD$_{655}$ was recorded, and the cell suspensions were centrifuged. A 5 µl volume of the supernatant was removed and assayed for chitinase activity. Biofilms remaining in the black 96 well plates were rinsed twice with PBS and assayed directly for chitinase activity. For assays of the Δbap1ΔrbmAΔrbmC mutant, cells were cultured in 1 ml of LB broth at 27° C. with shaking overnight. An OD$_{655}$ was recorded. The cell suspension was pelleted, and the supernatant was removed. Cells were rinsed once with PBS and then resuspended in an equal volume of PBS. 5 µl of the cell suspension and supernatant were assayed for chitinase activity. Chitinase activity was measured using a fluorometric chitinase assay kit (Sigma-Aldrich) according to the manufacturer's protocol including the following steps. Bacterial cells, biofilms, or supernatants were incubated in substrate buffer containing 0.2 mg/ml 4-methylumbelliferyl N,N'-diacetylchitobioside hydrate chitobiose for 20 minutes at 37° C. in the dark prior to measurement of fluorescence with an Infinite 200 spectrophotometer (Tecan).

Statistical analysis. Three experimental replicates were included in all quantitative experiments, and each experiment was repeated at least twice. Reported values represent the mean of the three experimental replicates, error bars represent the standard deviation, and statistical significance was calculated using a student's t-test.

Example 1

The bacterial biofilm matrix is comprised of exopolysaccharide, proteins, and DNA [2]. A model is emerging in which the biofilm exopolysaccharide is a scaffold to which adhesive proteins are anchored rather than the glue that holds the biofilm structure together [1,3]. We and others recently identified three such adhesive V. cholerae proteins, Bap1, RbmA, and RbmC [1,4-6]. Here we demonstrate the feasibility of using RbmA as a biofilm matrix targeting moiety for proteins of biological significance.

One licensed cholera vaccine includes killed whole V. cholerae cells combined with the purified B subunit of cholera toxin (CtxB), which serves as both an antigen and an adjuvant [7]. The purified CtxB component improves short term protection but also decreases affordability and ease of delivery. As a result, cholera vaccines manufactured in resource-poor settings have omitted this component [8,9]. We reasoned that engineering *V. cholerae* to decorate its biofilm exopolysaccharide scaffold with CtxB could greatly simplify the production and administration of a vaccine including CtxB and also potentially improve vaccine efficacy. In a proof of principle experiment, we engineered wild-type *V. cholerae* to express RbmA with either the CtxB subunit or a FLAG affinity tag fused to its C-terminus. Biofilms were formed with these strains. To determine if the RbmA-CtxB fusion protein was sequestered to the biofilm matrix, we subjected these biofilms to immunofluorescence using an antibody recognizing CtxB.

Figures 1A, 1B:
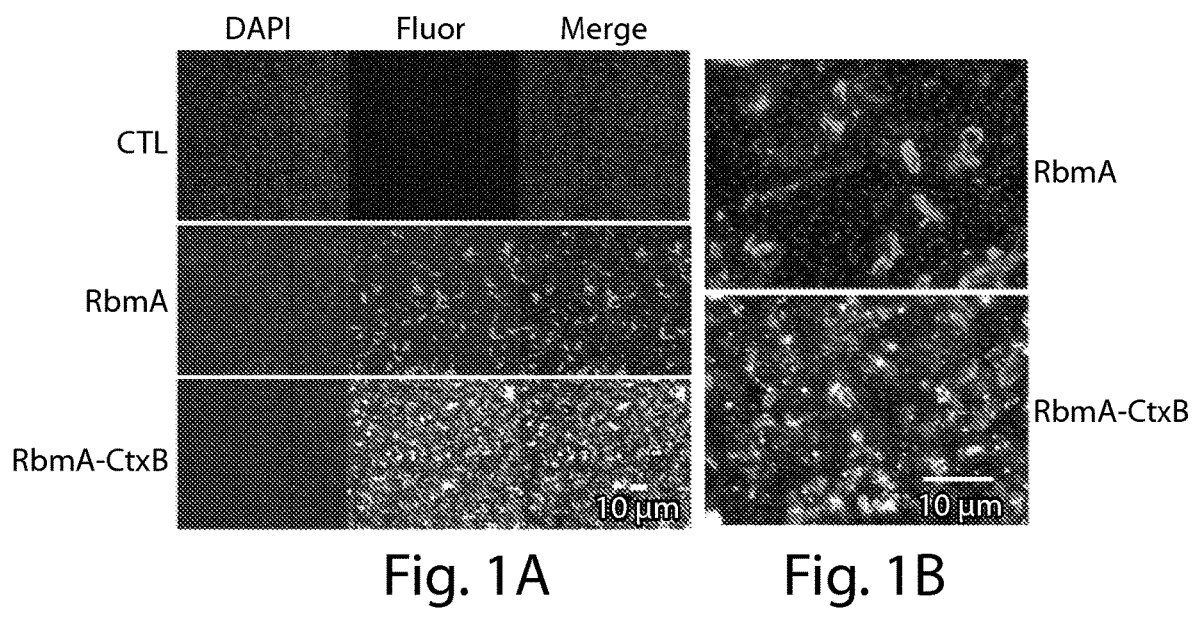

As a control, a biofilm formed by wild-type *V. cholerae* carrying an empty vector was also subjected to immunofluorescence using an anti-CtxB antibody. As shown in FIG. 1, the RbmA-CtxB fusion was visualized in the biofilm in a distribution similar to that of RbmA-FLAG. However, the anti-CtxB antibody did not associate with the biofilm in the absence of the RbmA-CtxB fusion protein. This result suggests that bacteria can be engineered to deliver and concentrate antigens or adjuvants at their surfaces by fusion to biofilm matrix-associated proteins. Such engineered bacterial strains could be candidates for live-attenuated or killed whole cell vaccines. Exemplary sequences of the respective fusions are provided below:

RbmA-FLAG:

(SEQ ID NO: 35)

```
MSNFKGSIMNKRHYYLASCLALLFSTASYAEVDCELQPVIEANLSLNQN
QLASNGGYISSQLGIRNESCETVKFKYWLSIKGPEGIYFPAKAVVGVDT
AQQESDALTDGRMLNVTRGFWVPEYMADGKYTVSLQVVAENGKVFKANQ
EFVKGVDLNSLPELNGLTIDIKNQFGINSVESTGGFVPFTVDLNNGREG
EANVEFWMTAVGPDGLIIPVNAREKWVIASGDTYSKVRGINFDKSYPAG
EYTINAQVVDIVSGERVEQSMTVVKKDYKDDDDK
```

RbmA-CtxB (SEQ ID NO: 36)

```
MSNFKGSIMNKRHYYLASCLALLFSTASYAEVDCELQPVIEANLSLNQN
QLASNGGYISSQLGIRNESCETVKFKYWLSIKGPEGIYFPAKAVVGVDT
AQQESDALTDGRMLNVTRGFWVPEYMADGKYTVSLQVVAENGKVFKANQ
EFVKGVDLNSLPELNGLTIDIKNQFGINSVESTGGFVPFTVDLNNGREG
EANVEFWMTAVGPDGLIIPVNAREKWVIASGDTYSKVRGINFDKSYPAG
EYTINAQVVDIVSGERVEQSMTVVKKMIKLKFGVFFTVLLSSAYAHGTP
QNITDLCAEYHNTQIYTLNDKIFSYTESLAGKREMAIITFKNGAIFQVE
VPGSQHIDSQKKAIERMKDTLRIAYLTEAKVEKLCVWNNKTPHAIAAIS
MAN
```

RbmA-ChiA-FLAG (SEQ ID NO: 37)

```
MSNFKGSIMNKRHYYLASCLALLFSTASYAEVDCELQPVIEANLSLNQN
QLASNGGYISSQLGIRNESCETVKFKYWLSIKGPEGIYFPAKAVVGVDT
AQQESDALTDGRMLNVTRGFWVPEYMADGKYTVSLQVVAENGKVFKANQ
EFVKGVDLNSLPELNGLTIDIKNQFGINSVESTGGFVPFTVDLNNGREG
EANVEFWMTAVGPDGLIIPVNAREKWVIASGDTYSKVRGINFDKSYPAG
EYTINAQVVDIVSGERVEQSMTVVKKMNRMTLCAASIACALASTAMAAP
SAPSVDVYGSNNLQFSKIELAMETTAGYNQMVKYHEEAPITLKFNQWSG
VTGNTYKIYFDGVEVATGPISGSQTTAQFTYPKGGVYQLVIEACDATGC
TKSAPSEITIADTDGSHLKPLKMNVDPNNKSYTIPQNTVIGTYFVEWSI
YDRKFTVDNIPGQNLTHILYGFIPICGPNESLKSVGGNSFNALQTACKG
VPDFEVVIHDPWAAYQKSFPQAGHQYSSPIKGNYAMLMALKKTYPDLKI
IPSIGGWTLSDPFFSFTDKAKRDVFVASVKRFLKTWKFYDGVDIDWEYP
GGGGQAADLGDPVKDGPAYVALMAELRAMLDELEAETGRKYELTSAIGV
GHDKIEDVNYGQAVQYMDYIFAMTYDFYGGWNNVLGHQTALYCGSFMRP
GQCDGKGVDENGEPYKGPAYTTDNGIQLLLAQGVPPSKLVVGAAMYGRG
WEGVTPASLKDPNDPMTGVGNGKLKGTTAQGVWEAGVIDYKGVKNFMLG
ANKTGVNGFEYGYDEQAEAPWVWNRTTGQLVTFDDDRSVKAKGAYVRNL
GLAGLFSWEIDADNGDILNAMHEGLAGGTTTPPVNKAPVANAGADITVT
GPAAVSLDGSASKDSDGSIASYLWEQTAGPAVTLTGANSAKASFNAAEV
TEKQTFTFKLTVTDNKGATATDTVVVTVNPKSTTPVNTAPVAALSAPAS
VKAGATVVVDASASSDADQDPLSFTWDLPVGVNATVQGAKVTFVAGEYT
QDTTLDFTVTVSDGKATSKASASVLVEKKAGTGGDACTNLWNAESIYTG
GQQVTWAGKTWEAKWWTRGEDPSKSGQWGVWKDLGAASCSTH DYKDDD
DK
```

Additionally, we reasoned that this technology might be used to deliver a functional enzyme to a surface. To model this, we inserted a secreted *V. cholerae* chitinase between RbmA and a C-terminal FLAG tag (RbmA-ChiA-2-FLAG) and expressed this fusion protein from a plasmid in wild-type *V. cholerae*. As controls, we also generated wild-type *V. cholerae* carrying an empty vector or the same vector encoding ChiA-2-FLAG. Biofilms were formed with these three strains, and immunofluorescence was performed using an anti-FLAG antibody. As shown in FIGS. 2A and B, the RbmAChiA-2-FLAG fusion was concentrated in the biofilm, whereas the ChiA-2-FLAG protein alone was not.

To be useful in surface modification, enzymes directed to the biofilm matrix must retain their activity. Therefore, we assessed whether the biofilm-associated RbmA-ChiA-2 fusion protein retained enzymatic activity. We formed biofilms with wild-type $V.$ $cholerae$ expressing RbmA-CtxB, ChiA-2-FLAG, or RbmA-ChiA-2-FLAG from a plasmid. As an additional control, a wild-type strain carrying an empty vector was included. Planktonic cells were removed, the biofilms were rinsed, and the chitinase activity of the biofilms and cell supernatants was tested. As shown in FIG. 2C, chitinase activity was approximately 15 times greater in the biofilm formed by the strain expressing the RbmAChiA-2-FLAG fusion than in any of the other biofilms tested. Because chitinase is a secreted protein native to $V.$ $cholerae$, chitinase activity was high in all the cell supernatants, particularly those expressing either ChiA-2-FLAG alone or the RbmAChiA-2-FLAG fusion protein (FIG. 2D). These experiments show that the biofilm matrix can be used to deliver active enzymes to surfaces.

For some applications, it may be advantageous to anchor proteins to planktonic cells. Bap1 and RbmC are found at the biofilm-surface interface and are important for anchoring the biofilm to surfaces. When biofilms are formed under static growth conditions, a $V.$ $cholerae$ Δbap1ΔrbmC mutant forms a multicellular structure or pellicle at the air-water interface, but this structure does not adhere to the walls of the well. Therefore, in quantitative assays of biofilm association, the Δbap1ΔrbmC mutant pellicle is easily dislodged, and the resulting measurement is indistinguishable from that of an exopolysaccharide mutant [1,5]. In contrast, RbmA is distributed throughout the biofilm and cements intercellular interactions. The ΔrbmA mutant biofilm forms a pellicle at the air-water interface that remains strongly attached to the surface. However, the pellicle is easily dispersed by vortexing [1,4]. The biofilm defects of both the Δbap1ΔrbmC mutant and the ΔrbmA mutant can rescued by addition of these purified proteins to the culture medium 1. This suggests that the exopolysaccharide scaffold is synthesized and exported in the absence of matrix protein synthesis.

Figure 3B:
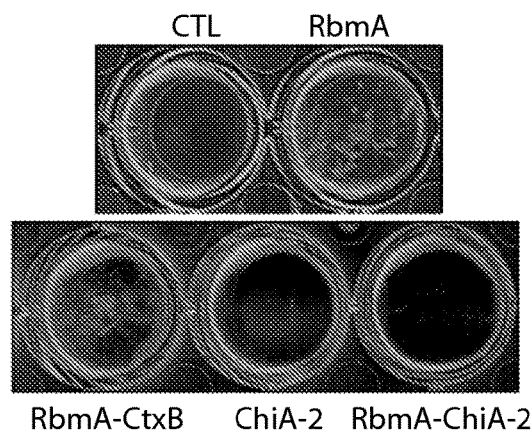

We hypothesized that a Δbap1 ΔrbmA ΔrbmC mutant would be defective in cell-surface and cell-cell interactions and, therefore, unable to form a biofilm. To test this, we created this triple mutant and assessed biofilm formation. As shown in FIGS. 3A and B, the triple mutant did not associate with the surfaces in quantitative assays and did not form a pellicle. Pellicle formation was rescued, however, by a plasmid encoding RbmA-FLAG or RbmA-CtxB (FIG. 3B). Expression of ChiA-2-FLAG and the RbmAChiA-2-FLAG from a plasmid did not rescue pellicle formation by the triple mutant. This suggests that, unlike RbmA and RbmA-CtxB, the RbmA-ChiA-2-FLAG protein is unable to mediate intercellular interactions.

Figure 3C:
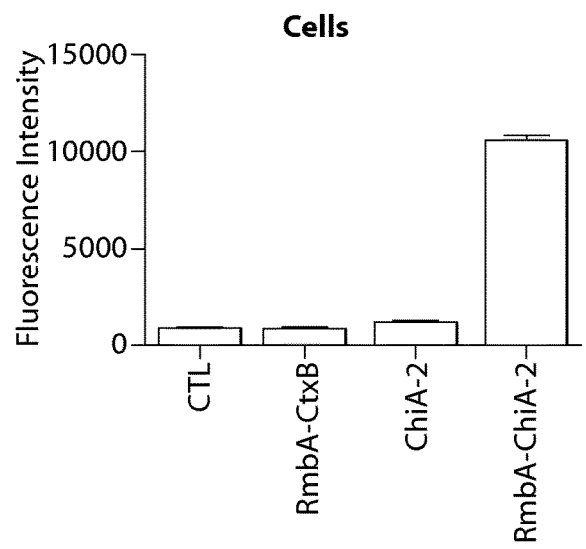
Figure 3D:
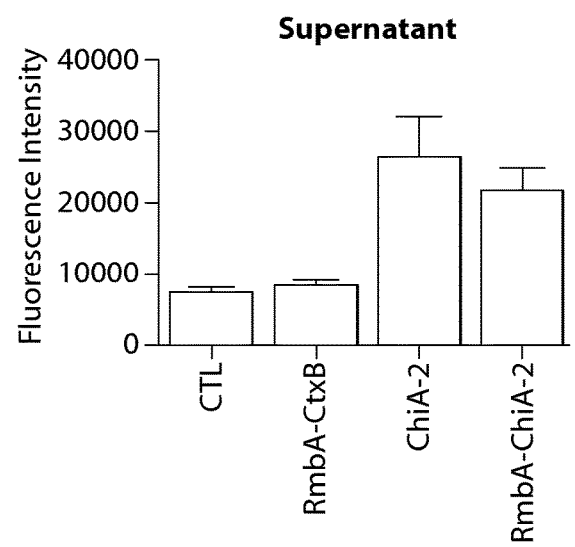

To determine whether the RbmA-ChiA2-FLAG fusion remained associated with cells in the absence of biofilm formation, a triple mutant expressing RbmA-ChiA-2-FLAG was cultured with agitation, cells were pelleted, and the chitinase activity of both the cellular fraction and the supernatant was assayed. As shown in FIGS. 3C and D, chitinase activity was sequestered to cells expressing the RbmA-ChiA-2-FLAG fusion but not to cells expressing ChiA-2-FLAG or RbmA-CtxB. This suggests that RbmA-ChiA-2-FLAG is cell-associated even in the absence of a biofilm structure. We hypothesize that the biofilm matrix exopolysaccharide is produced and exported by the triple mutant.

Furthermore, although RbmA-ChiA-2-FLAG is unable to mediate intercellular interactions, it likely retains the ability to associate with this matrix exopolysaccharide and remains functional on the cell surface. These experiments suggest that this protein presentation platform can also be adapted for use in planktonic bacterial cells.

Example 2

Like other bacteria, $Vibrio$ $cholerae$ synthesizes a highly regulated extracellular matrix that enables attachment to surfaces in a complex, three-dimensional multicellular structure known as a biofilm. Components of the biofilm matrix include exopolysaccharide, protein, and DNA. The polysaccharide component of the biofilm matrix has often been thought of as the glue that stabilizes the biofilm structure. We have recently completed the first proteomic analysis of a Gram-negative bacterial biofilm matrix [1]. Our findings suggest that the $V.$ $cholerae$ biofilm exopolysaccharide is tightly associated with the cell of origin, while secreted matrix-associated proteins are a communal resource required for cell-cell and cell-surface interactions. Furthermore, once secreted, these proteins segregate to distinct regions of the biofilm matrix to maintain the structural integrity of the biofilm.

Biofilm matrix-associated proteins can be harnessed to target enzymes or antigens of interest to specific regions of the biofilm matrix of Gram-negative bacteria. Engineered peptides that attach to the biofilm matrix in distinct distributions are provided herein. Proof of principle experiments in which a heterologous molecule (e.g., the enzyme chitinase or the cholera toxin B subunit) conjugated to an exopolysaccharide-associated protein or protein fragment is delivered to a biofilm comprising the exopolysaccharide, either uniformly or in a specific spatial distribution are also described herein. As described in more detail herein, engineered biofilm matrix-associated proteins for antigen presentation and targeting of enzymes to surfaces can be used for antigen presentation in vaccine development and to expand the enzymatic functionality of the bacterial biofilm matrix for therapeutic and bioengineering applications.

Proteins associated with the biofilm matrix. A recently published study represents the first comprehensive analysis of proteins associated with the Gram-negative biofilm matrix. [1] The experiments described here will advance the understanding of the mechanisms by which proteins are retained in the biofilm matrix, the spectrum of functions carried out by biofilm matrix-associated proteins, and the mechanisms by which proteins maintain spatial segregation in the biofilm.

In contrast to current views of the biofilm matrix proteins as the "glue" that holds the biofilm together, in which the biofilm matrix polysaccharide is depicted as a secreted, continuous matrix in which biofilm-associated bacteria are embedded, the preliminary results provided herein suggest that the $V.$ $cholerae$ matrix exopolysaccharide is tightly associated with cells and provides a scaffold for biofilm matrix-associated proteins. It is these proteins that mediate the intercellular and cell-surface contacts that provide structure to the biofilm.

Based on this understanding, different uses of bacterial biofilm matrix proteins and of biofilm matrix-associated proteins or protein fragments in novel applications is envisioned. For example, as described herein, biofilm matrix-associated proteins are spatially localized. For another example, the use of the biofilm matrix as a platform for presentation of antigens and delivery of functional enzymes to surfaces is envisioned. Heterologous molecules of interest, e.g., heterologous antigens or enzymes, can be strategically targeted to specific parts of a biofilm by conjugating them to proteins or protein fragments that associate with particular regions of the biofilm matrix.

Bacterial Biofilm Formation.

Biofilm formation is the process by which bacteria attach to a living or non-living surface. In biofilms comprised of multiple layers of bacteria, cell-cell and cell-surface interactions are mediated by a secreted matrix of natural polymers that may include exopolysaccharides, protein, and DNA. This matrix is secreted in response to specific environmental cues.

The *Vibrio cholerae* Multilayer Biofilm Matrix.

*V. cholerae* is an epidemic diarrheal pathogen of humans and a natural inhabitant of estuarine environments. When environmental conditions are favorable, *V. cholerae* forms a multilayer biofilm by elaborating a matrix that contains several proteins as well as the VPS polysaccharide, whose synthesis is largely encoded by the vps genes. It was recently demonstrated that the VPS polysaccharide is tightly associated with cells. Preliminary results suggest that it does not mediate biofilm formation directly. Rather, secreted biofilm matrix-associated proteins mediate the cell-cell and cell-surface interactions. [1].

Proteins in the *V. cholerae* Biofilm Matrix.

The first complete proteomic analysis of a bacterial biofilm matrix was recently published [1]. In that study, 10 proteins that are known to be secreted into the extracellular space were identified (Table 1) as well as 18 proteins that are predicted to be extracytoplasmic (Table 2).

Figure 4A:
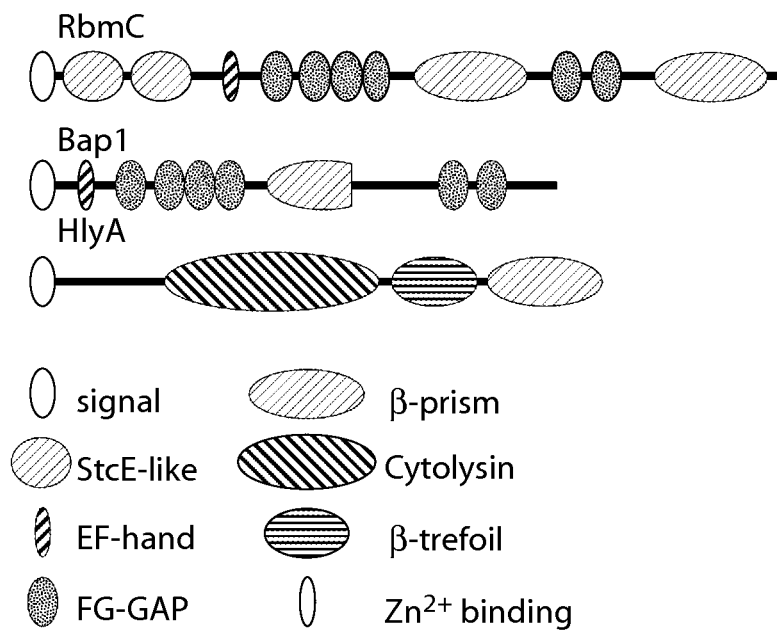
Figure 4B:
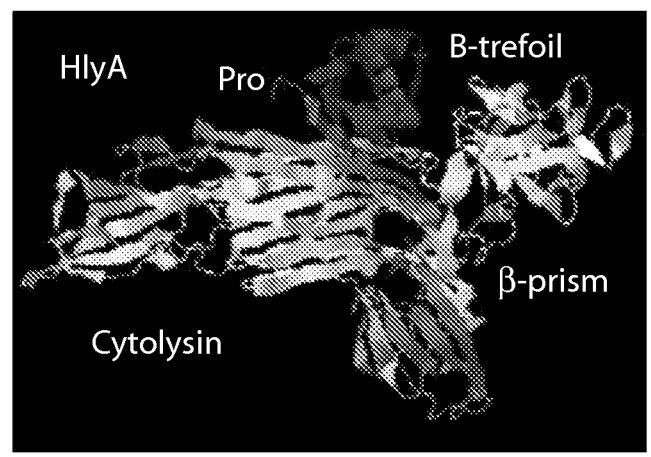

Type I β-Prism Domain-Containing Proteins in the *V. cholerae* Biofilm Matrix. Bap1, RbmC, and HlyA, three biofilm matrix-associated proteins identified, form a paralogous family of Type 1 β-prism lectin domain-containing proteins. Type I β-prism domains were first described in jacalin, a lectin found in the seeds of the Jack Fruit [15, 16]. Bap1 and RbmC are highly similar proteins with overlapping functions that are essential for biofilm formation [1, 6, 5]. These proteins contain multiple, conserved FG-GAP domains surrounding a β-prism domain (FIG. 4A). As a result, the β-prism domain is predicted to be part of a larger, β-propeller-like structure. While RbmC has conserved N and C terminal domains not found in Bap1, Bap1 represents the minimal peptide required to rescue the biofilm defect of a Δbap1ΔrbmC mutant. HlyA, a pore-forming toxin, is secreted as a protoxin and is activated by cleavage of the 15 kDa N-terminal chaperone-like domain. Activated HlyA consists of spatially separated cytolysin, β-trefoil, and β-prism domains (FIG. 4B) [17]. This protein forms heptameric pores in cholesterol and sphingolipid-rich cell membranes leading to membrane depolarization and/or hemoloysis [18, 19, 20]. There is evidence that HlyA associates with the *V. cholerae* biofilm matrix [1]. RbmA is a novel biofilm matrix-associated protein. RbmA is a secreted protein encoded in the VPS island. It has no conserved domains. Deletion of RbmA was originally noted to result in a weakened biofilm structure [4].

Figure 5:
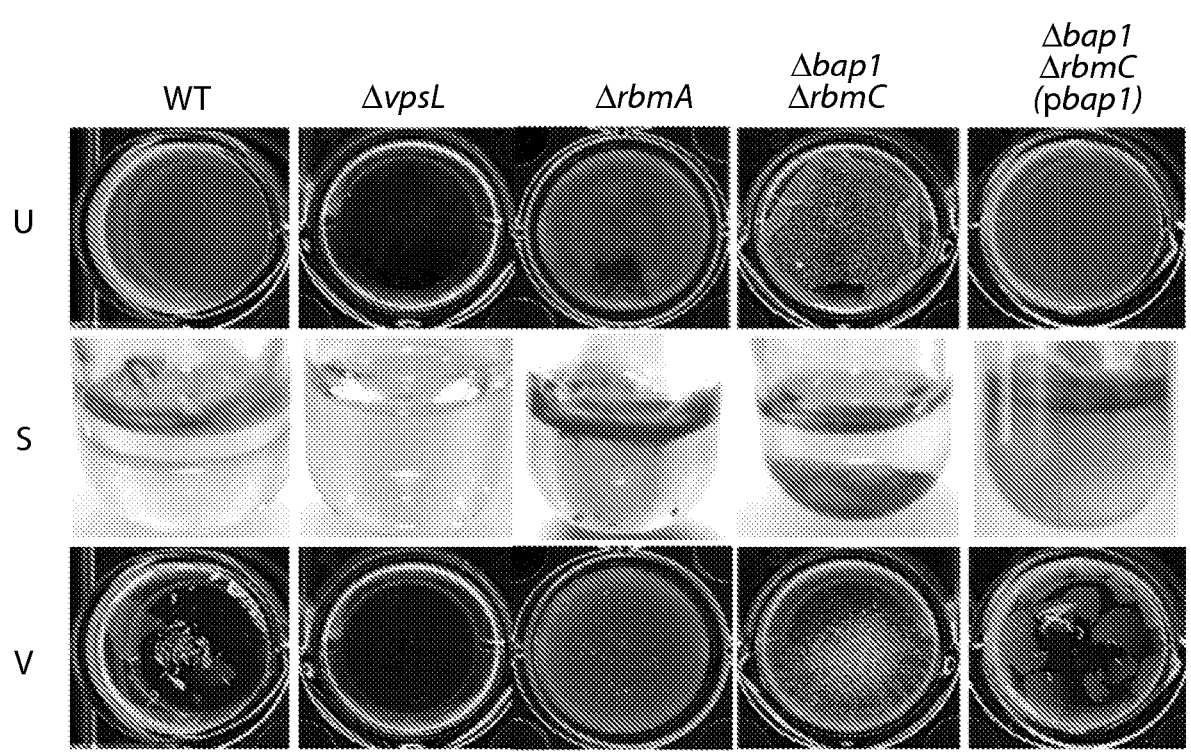

Bap1 reinforces the attachment of the biofilm to the surface, while RbmA strengthens intercellular contacts. The results shown herein suggest that RbmA plays a role in biofilm formation that is distinct from that of Bap1 and RbmC. As shown in FIG. 5, the Δbap1ΔrbmC mutant is able to form a pellicle, which is a biofilm structure found at the air-water interface. However, this pellicle is only weakly attached to the surrounding solid surface and, therefore, can be easily dissociated from the surface by gentle shaking. In contrast, ΔRbmA mutants form strong attachments to the surface that are not disrupted by shaking. However, when vortexed, the ΔrbmA mutant biofilm disperses into much smaller particles than the Δbap1ΔrbmC mutant biofilm, suggesting that RbmA reinforces intercellular contacts. The biofilm made by a Δbap1ΔrbmAΔrbmC mutant is indistinguishable from that made by a ΔvpsL mutant (data not shown).

Figure 6A:
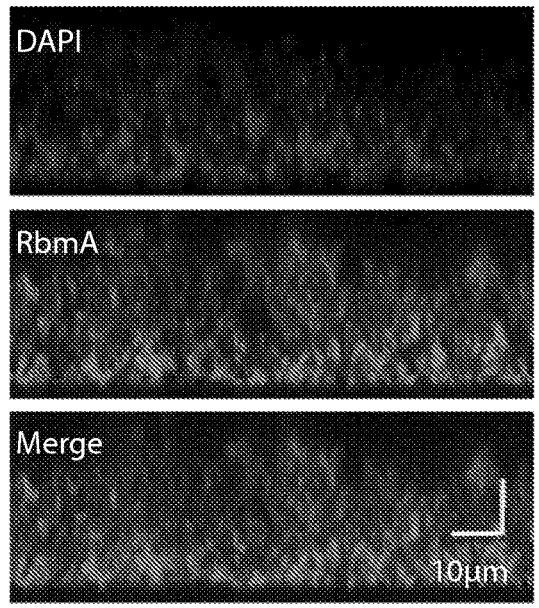
Figure 6B:
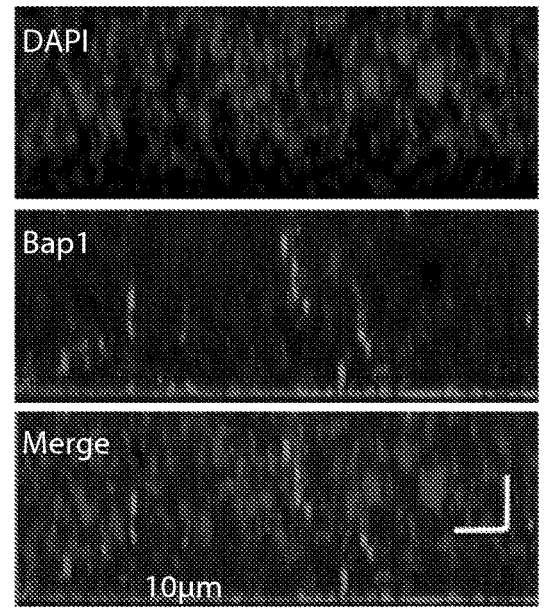
Figure 6C:
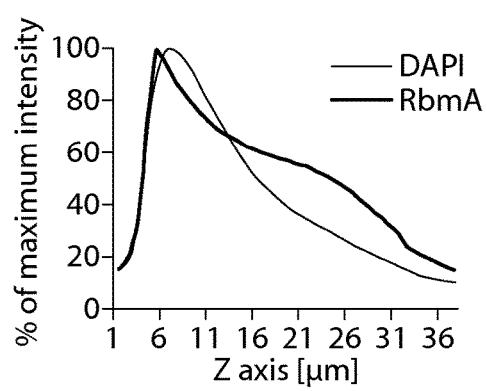
Figure 6C:
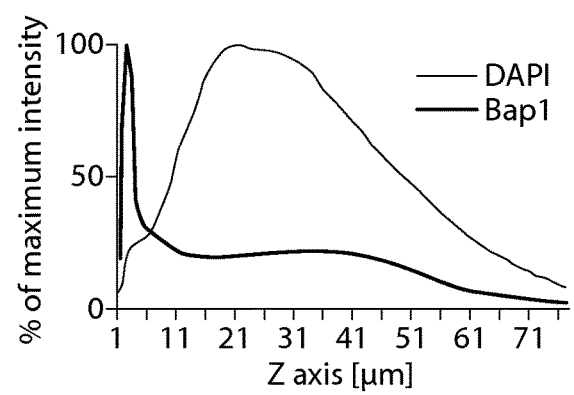

Bap1 and RbmC localize to the base of the biofilm, while RbmA is distributed throughout the biofilm. To correlate the observed biofilm formation defects of Δbap1ΔrbmC and ΔrbmA mutants with the distribution of these proteins in native biofilms, we added a FLAG affinity tag to the C-terminal end of Bap1, RbmC, and RbmA expressed from their native promoters and performed immunofluorescence microscopy on intact, viable biofilms (FIGS. 6A and B). To quantify the protein distribution, we measured the total fluorescence in each transverse section as a function of distance from the substratum (FIG. 6C). Controls were performed to demonstrate that: (i) all proteins were well-expressed and secreted, (ii) FLAG-tagged proteins did not disrupt biofilm formation, and (iii) cytoplasmic, periplasmic proteins, and other unrelated secreted proteins were NOT visible by this method.

Bap1 and RbmC were noted to localize to the biofilm-surface interface, while RbmA was distributed throughout the biofilm ([1] and data not shown). A similar protein distribution was observed when expression of these proteins was driven by a constitutive promoter on a plasmid, suggesting that spatial localization of proteins in the biofilm is not the result of differential transcription [1].

Addition of purified Bap1 or RbmA can restore wild-type biofilm formation to a Δbap1ΔrbmC or ΔrbmA mutant, respectively. Affinity-tagged Bap1 and RbmA were purified from the supernatants of *V. cholerae* strains. Each mutant was allowed to form a biofilm in the presence of the purified protein that it lacked. Addition of purified Bap1 or RbmA rescued the biofilm defect of the corresponding mutant [1].

Four biofilm matrix-associated proteins, Bap1, RbmA, RbmC, and HlyA were characterized. The resulting data suggest that these proteins are spatially segregated in the biofilm and adhere to the exopolysaccharide component of the matrix. Accordingly, these proteins can be used to target heterologous molecules, such as functional proteins to specific regions of the biofilm matrix.

Example 3 (Prophetic)

Structure-Function analysis of HlyA. Of the β-prism domain-containing proteins specifically discussed herein, HlyA has been most intensively studied because of its hemolytic activity [17, 18, 19]. Although it has not previously been implicated in biofilm formation, researchers have postulated a role for HlyA in the environment because it is well-represented in environmental strains of *V. cholerae* [21, 22]. In this experiment, the role of HlyA in biofilm formation is characterized and the minimal HlyA peptide required for association with the biofilm, or, in other words, the minimal exopolysaccharide-binding HlyA fragment, is identified.

Characterization of the Role of Full Length HlyA in Biofilm Formation.

First, an in-frame deletion of HlyA in a wild-type genetic background is constructed to determine if HlyA plays a role in biofilm surface attachment and/or structure. The impact of HlyA deletion in a Δbap1ΔrbmC mutant background is also assessed in order to determine if the function of HlyA overlaps at all with that of Bap1 and RbmC. Surface attachment is quantified and the resistance of ΔhlyA and ΔhlyA Δbap1ΔrbmC biofilms to shaking and vortexing is analyzed in analogy to the analyses performed for ΔrbmA and Δbap1ΔrbmC biofilms. If a biofilm phenotype is observed, rescue experiments are performed with an HlyA-FLAG construct encoded on a plasmid. Adequate protein expression is confirmed by Western analysis.

Distribution of HlyA in the Biofilm Matrix.

In this experiment, the transverse and vertical distributions of HlyA in the *V. cholerae* biofilm matrix are defined. The goal of this experiment is two-fold: first, to better understand the roles of the conserved domains of HlyA in spatial localization within the biofilm; and second, to identify additional proteins with distinct matrix distributions within the biofilm that may be useful to target proteins to different regions within the biofilm matrix. To this end, strains are constructed that express HlyA-FLAG both from its native promoter on the chromosome and from a constitutive promoter on a plasmid. After these tagged HlyA constructs are confirmed to be well expressed by Western analysis, the distribution of these proteins in the biofilm are examined by coupling confocal microscopy with immunofluorescence. The distribution of HlyA in the biofilm matrix is compared to that of Bap1, RbmA, and RbmC.

Role of the HlyA Cytolysin, β-Trefoil, and β-Prism Domains in Biofilm Matrix association.

As illustrated in the crystal structure shown in FIG. 4, the domains of HlyA are spatially separated. The minimal peptide required for attachment to the *V. cholerae* biofilm matrix is identified. From a plasmid, a series of six FLAG-tagged, HlyA-based peptides are constitutively expressed. These engineered peptides include either one or two conserved domains of HlyA. After establishing expression and stability, association of these peptides with the biofilm matrix is assessed by immunofluorescence. A negative result is not informative as it might reflect severe compromise of the three-dimensional domain structure. However, a positive result allows to assign roles in biofilm association to one or more domains of HlyA. If HlyA plays an essential role in biofilm formation, these experiments are performed in a wild-type genetic background only. Otherwise, these experiments are performed in ΔhlyA and Δbap1ΔrbmC mutant g backgrounds as well as in wild-type *V. cholerae.*

Functional Analysis of HlyA Point Mutants.

If the β-trefoil and β-prism domains are required for biofilm matrix association, mutation of the conserved sugar-binding residues within these domains will decrease protein retention within the biofilm. In this experiment, residues in the β-trefoil and β-prism lectin domains of HlyA that are predicted to be critical for binding to the polysaccharide component of the biofilm matrix are mutated.

The β-trefoil domain of HlyA contains two out of three QXW sugar-binding motifs that are conserved in ricin-like lectins (Q537/F539 and Q574/W576). In the crystal structures of β-prism domains of jacalin-like lectins, several conserved amino acids are known to make contacts with the bound sugar. These include an aspartate in a GXXXD motif that forms a hydrogen bond with the sugar and two aromatic residues that form stacking interactions with the bound sugar [23]. The β-prism domain of HlyA contains these conserved putative sugar binding residues (G647, D651, Y698, and Y723). FLAG-tagged versions of full length HlyA and HlyA peptides found to be matrix-associated in the experiment above are constructed with one or more of the conserved residues replaced by alanine. Mutant proteins are expressed from a plasmid along with a C-terminal FLAG-tag in wild-type *V. cholerae* as well as in ΔhlyA and Δbap1ΔrbmC mutants. After ascertaining that these mutant proteins are adequately expressed and stable by Western analysis, their biofilm retention and spatial localization within the pellicle or biofilm matrix is assessed by immunofluorescence. The creation of point mutations by alanine substitution is unlikely to disturb the protein structure. If a mutation of a residue has no effect on matrix binding, it can be concluded that this residue is not essential for matrix binding function.

Example 4 (Prophetic)

Identification of Additional Biofilm Matrix-Binding Proteins.

Eighteen additional candidate matrix-associated proteins that were identified in a preliminary proteomic analysis are characterized (see Table 2). While all of these proteins are predicted to be secreted, their function and role in biofilm formation has not been characterized. The preliminary results are validated by characterizing the role and distribution of confirmed biofilm matrix-associated proteins using an approach that has been successful in characterization of Bap1, RbmA, and RbmC [1].

Confirmation of Protein Secretion.

To establish that the proteins listed in Table 2 are secreted outside the cell, the relevant gene is cloned along with its native signal sequence and a C-terminal FLAG affinity tag into an IPTG-inducible expression vector. These vectors are electroporated into wild-type *V. cholerae*. The engineered strains are grown to mid-log phase in the presence and absence of inducer (IPTG). Cells are pelleted and separated from the supernatant. Western analysis is carried out on both the cell pellet and supernatant to determine if the proteins are expressed and secreted. Similarly treated strains expressing FLAG-tagged cytoplasmic and periplasmic proteins are used as controls to establish that the experimental treatment does not release cytoplasmic and periplasmic contents into the medium. Importantly, the controls behaved appropriately in previous experiments that are now published [1].

Assessment of biofilm matrix association. To determine whether secreted proteins are selectively retained in the matrix, biofilms are formed with strains expressing the FLAG-tagged proteins and the proteins are visualized in the biofilm matrix using immunofluorescence. Similarly expressed cytoplasmic and periplasmic proteins are used as controls. Only proteins that are secreted and visualized in the biofilm matrix are pursued further.

Native Distribution of Proteins in the Biofilm Matrix.

The native distributions of proteins found to associate with the biofilm matrix is characterized. Strains are constructed in which the protein of interest is expressed from its native promoter with the addition of a C-terminal FLAG affinity tag. Biofilms are formed with these strains, and immunofluorescence is used to image the distribution of the protein in the biofilm.

Role of Biofilm Matrix-Associated Proteins in Biofilm Formation.

In order to determine the function of biofilm matrix-associated proteins in biofilm formation, *V. cholerae* carrying in-frame deletions in the genes encoding these proteins are created. Biofilm formation by these mutants is quantified and compared to that by wild-type *V. cholerae*. The resistance of mutant biofilms to surface dissociation and dispersal is also tested by shaking and vortexing. If no phenotype is observed, it is concluded that the respective protein does not play a structural role in biofilm formation.

Identification of Minimum Biofilm-Association Peptides.

For any multi-domain proteins that are identified in these experiments, experiments similar to those described for HlyA are performed to identify the minimal peptide required for association with the biofilm.

Example 5 (Prophetic)

There is evidence that matrix-associated proteins fulfill similar roles in the biofilms of other organisms [12, 13, 24, 25]. While *V. cholerae* may not be a suitable host for some applications, the "proof of principle" experiments described herein serve as a model for application development in other bacteria.

Targeting a Secreted, Active Enzyme to a Specific Location within the Biofilm Matrix.

ChiA-2 is an efficiently secreted chitinase that is not concentrated in the biofilm matrix [1]. In this experiment, ChiA-2 is targeted to the biofilm matrix via conjugation to an exopolysaccharide-associated protein. The tagged versions of each of the exopolysaccharide-associated proteins described herein are fused to the C-terminus of ChiA-2 via recombinant technology, and the recombinant nucleic acids encoding the resulting chimeric proteins are placed in a neutral chromosomal location such as the lacZ gene of wild-type *V. cholerae*. Immunofluorescence is used to compare the levels and distribution of ChiA-2 in the biofilm matrix in the presence and absence of the recombinant proteins. For all chimeric proteins that successfully localize ChiA-2 in the biofilm matrix, a fluorescent chitinase substrate is used to compare biofilm-associated chitinase activity in the presence and absence of matrix-associated ChiA-2.

It is expected that it is possible to target a protein, e.g., ChiA-2 to either the substrate-biofilm interface or the biofilm apex by using specific exopolysaccharide-associated proteins as fusion partners for the protein. In some embodiments, surface-active proteins (e.g., proteins with antibacterial, glycolytic, lipolytic, or proteolytic activity) are targeted to concentrate at the biofilm matrix-surface interface for purposes of medical treatment or bioremediation.

Targeting a Secreted Antigen to the Biofilm Matrix.

The oral cholera vaccine currently licensed in Europe consists of whole cell, killed *V. cholerae* strains combined with the purified cholera toxin B subunit (CtxB) [26]. This vaccine affords some protection against cholera and traveler's diarrhea but is expensive to produce and administer. Therefore, simpler whole cell, killed vaccines have been developed in Vietnam and India [9].

A whole cell, killed vaccine strain that concentrates CtxB in the biofilm matrix would be less expensive to administer and produce and could be more immunogenic. Furthermore, one could engineer a strain that also incorporated protein antigens affording protection against other diarrheal diseases, thus generating a broad spectrum diarrheal vaccine.

To explore this application, a strain of *V. cholerae* is engineered in which CtxB is targeted to the biofilm matrix via fusion to an exopolysaccharide-associated protein. The resulting biofilm is processed into a killed-cell vaccine according to methods known to those of skill in the art. The vaccine is administered to a human subject, resulting in an immune response similar to that of a currently licensed *V. cholerae* vaccine.

REFERENCES

1. Absalon, C., Van Dellen, K. & Watnick, P. I. A communal bacterial adhesin anchors biofilm and bystander cells to surfaces. PLoS Pathog 7, e1002210 (2011).
2. Karatan, E. & Watnick, P. Signals, regulatory networks, and materials that build and break bacterial biofilms. Microbiol Mol Biol Rev 73, 310-347 (2009).
3. Nadell, C. D. & Bassler, B. L. A fitness trade-off between local competition and dispersal in *Vibrio cholerae* biofilms. Proc Natl Acad Sci USA 108, 14181-14185 (2011).
4. Fong, J. C., Karplus, K., Schoolnik, G. K. & Yildiz, F. H. Identification and characterization of RbmA, a novel protein required for the development of rugose colony morphology and biofilm structure in *Vibrio cholerae*. J Bacteriol 188, 1049-1059 (2006).
5. Fong, J. C. & Yildiz, F. H. The rbmBCDEF gene cluster modulates development of rugose colony morphology and biofilm formation in *Vibrio cholerae*. J Bacteriol 189, 2319-2330 (2007).
6. Moorthy, S. & Watnick, P. I. Identification of novel stage-specific genetic requirements through whole genome transcription profiling of *Vibrio cholerae* biofilm development. Mol Microbiol 57, 1623-1635 (2005).
7. Svennerholm, A. M. From cholera to enterotoxigenic *Escherichia coli* (ETEC) vaccine development. Indian J Med Res 133, 188-196 (2011).
8. Saha, A., et al. Safety and immunogenicity study of a killed bivalent (O1 and O139) whole-cell oral cholera vaccine Shanchol, in Bangladeshi adults and children as young as 1 year of age. Vaccine 29, 8285-8292 (2011).
9. Lopez-Gigosos, R. M., Plaza, E., Diez-Diaz, R. M. & Calvo, M. J. Vaccination strategies to combat an infectious globe: oral cholera vaccines. J Glob Infect Dis 3, 56-62 (2011).
10. Romero, D., Aguilar, C., Losick, R. & Kolter, R. Amyloid fibers provide structural integrity to *Bacillus subtilis* biofilms. Proc Natl Acad Sci USA 107, 2230-2234.
11. Vidal, O., et al. Isolation of an *Escherichia coli* K-12 mutant strain able to form biofilms on inert surfaces: involvement of a new ompR allele that increases curli expression. J Bacteriol 180, 2442-2449 (1998).
12. Diggle, S. P., et al. The galactophilic lectin, LecA, contributes to biofilm development in *Pseudomonas aeruginosa*. Environ Microbiol 8, 1095-1104 (2006).
13. Tielker, D., et al. *Pseudomonas aeruginosa* lectin LecB is located in the outer membrane and is involved in biofilm formation. Microbiology 151, 1313-1323 (2005).
14. Haugo, A. J. & Watnick, P. I. *Vibrio cholerae* CytR is a repressor of biofilm development. Mol Microbiol 45, 471-483 (2002).
15. Sankaranarayanan R, Sekar K, Banerjee R, Sharma V, Surolia A, et al. (1996) A novel mode of carbohydrate recognition in jacalin, a Moraceae plant lectin with a beta-prism fold. Nat Struct Biol 3: 596-603.
16. Roque-Barreira M C, Campos-Neto A (1985) Jacalin: an IgA-binding lectin. J Immunol 134: 1740-1743.
17. Olson R, Gouaux E (2005) Crystal structure of the *Vibrio cholerae* cytolysin (VCC) protoxin and its assembly into a heptameric transmembrane pore. J Mol Biol 350: 997-1016.
18. Krasilnikov O V, Merzlyak P G, Lima V L, Zitzer A O, Valeva A, et al. (2007) Pore formation by *Vibrio cholerae* cytolysin requires cholesterol in both monolayers of the target membrane. Biochimie 89: 271-277.
19. Zitzer A, Zitzer O, Bhakdi S, Palmer M (1999) Oligomerization of *Vibrio cholerae* cytolysin yields a pentameric pore and has a dual specificity for cholesterol and sphingolipids in the target membrane. J Biol Chem 274: 1375-1380.

20. Singh D V, Matte M H, Matte G R, Jiang S, Sabeena F, et al. (2001) Molecular analysis of *Vibrio cholerae* O1, O139, non-O1, and non-O139 strains: clonal relationships between clinical and environmental isolates. Appl Environ Microbiol 67: 910-921.
21. Rahman M H, Biswas K, Hossain M A, Sack R B, Mekalanos J J, et al. (2008) Distribution of genes for virulence and ecological fitness among diverse *Vibrio cholerae* population in a cholera endemic area: tracking the evolution of pathogenic strains. DNA Cell Biol 27: 347-355.
22. Goel A K, Jain M, Kumar P, Kamboj D V, Singh L Virulence profile and clonal relationship among the *Vibrio cholerae* isolates from ground and surface water in a cholera endemic area during rainy season. Folia Microbiol (Praha) 55: 69-74.
23. Raval S, Gowda S B, Singh D D, Chandra N R (2004) A database analysis of jacalin-like lectins: sequence-structure-function relationships. Glycobiology 14: 1247-1263.
24. Borlee B R, Goldman A D, Murakami K, Samudrala R, Wozniak D J, et al. *Pseudomonas aeruginosa* uses a cyclic-di-GMP-regulated adhesin to reinforce the biofilm extracellular matrix. Mol Microbiol 75: 827-842.
25. Danese P N, Pratt L A, Dove S L, Kolter R (2000) The outer membrane protein, antigen 43, mediates cell-to-cell interactions within *Escherichia coli* biofilms. Mol Microbiol 37: 424-432.
26. Lopez-Gigosos R, Garcia-Fortea P, Reina-Dona E, Plaza-Martin E (2007) Effectiveness in prevention of travelers' diarrhea by an oral cholera vaccine WC/rBS. Travel Med Infect Dis 5: 380-384. 2

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A live attenuated *Vibrio cholerae* that produces a biofilm exopolysaccharide, wherein the *Vibrio cholerae* is engineered to comprise a recombinant nucleic acid encoding a fusion protein comprising the RbmA exopolysaccharide-associated protein fused to a heterologous protein antigen of a pathogen, wherein the RbmA comprises the amino acid sequence of SEQ ID NO: 2 and the live attenuated *Vibrio cholerae* induces an immune response to the heterologous protein antigen upon its administration in an effective amount to a mammalian subject.

2. The live attenuated vaccine of claim 1, wherein the heterologous protein antigen is of a pathogenic bacterium.

3. The live attenuated vaccine of claim 2, wherein the heterologous protein antigen is cholera toxin B subunit (CtxB).

4. The live attenuated vaccine of claim 3, wherein the fusion protein is RbmA-CtxB fusion protein comprising the amino acid sequence of SEQ ID NO: 36.

5. A composition comprising the engineered live attenuated *Vibrio cholerae* of claim 1.

6. A method of immunizing a mammalian subject against a pathogen, the method comprising administering to the mammalian subject an amount of the composition of claim 5 sufficient to elicit an immune response to the heterologous protein antigen of the pathogen in the subject.

* * * * *

SEQUENCE LISTING

<160> NUMBER OF SEQ ID NOS: 37

<210> SEQ ID NO 1
<211> LENGTH: 691
<212> TYPE: PRT
<213> ORGANISM: Artificial Sequence
<220> FEATURE:
<223> OTHER INFORMATION: Synthetic Polypeptide

<400> SEQUENCE: 1

```
Met Lys Gln Thr Lys Thr Leu Thr Ala Ile Ser Val Leu Ala Leu Ser
1               5                   10                  15

His Leu Met Thr Gln Ser Thr Ala Phe Ala Ser Ser Ser Asp Ile
            20                  25                  30

Gln Thr Lys Leu Lys Trp Ser Trp Ser Thr Ser Val Phe His Pro Glu
        35                  40                  45

Ser Asn Gln Val Met Ala Ala Pro Ile Val Gln Leu Asn Asp Asp
    50                  55                  60

Asn Gly Asp Gly Lys Ile Asp Glu Lys Asp Val Ala Asp Ile Ile Val
65                  70                  75                  80

Val Thr Phe Glu Gly Asn Lys Tyr Ala Asn Gly Gly Tyr Ile Arg Ala
                85                  90                  95

Leu Ser Gly Val Asp Gly Ser Glu Leu Trp Ser Tyr Ser Asn Gly Gly
            100                 105                 110

Val Ile Ala Asp Ala Arg Tyr Ala Pro Ala Ala Asp Leu Asp Gly
        115                 120                 125

Asp Gly Leu Ile Glu Ile Val Ser Thr Ser Ala Leu Thr Pro Tyr Ile
    130                 135                 140

Asn Ile Leu Asp His Gln Gly Asn Ile Lys Lys Gln Leu Leu Lys Ser
145                 150                 155                 160

Ala Ser Gly Trp Arg Ser Val Gly Asp Ile Ala Leu Ala Asp Ile Asn
                165                 170                 175

Gly Asp Gly Asn Ile Glu Ile Leu Ala Ala Asp Gly Val Tyr Ser Tyr
            180                 185                 190

Glu Ser Gly Leu Leu Phe Ser His Asp Trp Ala Pro Ser Ser Ile Ala
        195                 200                 205

Phe Asp Ser Asn Gly Asp Gly Gln Arg Glu Val Phe Ala Asn Gly Thr
    210                 215                 220

Leu Tyr Gln Asn Asn Gly Ala Tyr Leu Trp Gln Tyr Gln Ala Asn Asp
225                 230                 235                 240

Thr Val Trp Phe Ser Ser Val Ala Asn Leu Asp Gly Asp Lys Pro
                245                 250                 255

Glu Leu Val Val Ser Val Pro Ala Ser Leu Ser Thr Pro Glu Asn Ser
            260                 265                 270

Glu Ile Ala Val Leu Glu His Asp Gly Ser Val Lys Trp Arg Val Asn
        275                 280                 285

Asn Leu Ser Asn Pro Gly Gly Ser Val Gln Ala Val Ser Ser Phe Leu
    290                 295                 300

Gly Lys Pro Ser Ser Ser Ala Thr Thr Val Asp Ala Gln Ser Ala Val
305                 310                 315                 320

Tyr Gly Tyr Thr Asp Trp Ala His Gln Gln Arg Val Leu Ala Glu Asn
                325                 330                 335

His Gln Leu Ala Ile Arg Ser Gly Ala Val Val Asp Ala Ile Gly Ala
            340                 345                 350

Asn Ser Gln Asn Met Ile Gly Gly Ser Gly Gly Ser Leu Ser Thr Ile
```

```
            355                 360                 365
Asp Thr Ser Lys Val Arg Ala Ile Asp Val Thr Tyr Gly Lys Asn Lys
    370                 375                 380

Tyr Thr Trp Lys Tyr Gly Val Leu Glu Met Ser Phe Thr Leu Asp Asn
385                 390                 395                 400

Gly Ala Lys Val Thr Val Gly Ser Lys Asp Ser Ala Phe Thr Tyr Leu
                405                 410                 415

Gly Leu Glu Trp Lys Thr Lys Thr Val Pro Tyr Leu Gly Val Glu Trp
            420                 425                 430

Arg Thr Lys Thr Val Ser Tyr Trp Phe Phe Gly Trp His Thr Lys Gln
        435                 440                 445

Val Ala Tyr Leu Ala Pro Val Trp Lys Glu Lys Thr Ile Pro Tyr Ala
    450                 455                 460

Val Pro Val Thr Leu Ser Lys Ser Thr Thr Val Arg Tyr Asp Ile Pro
465                 470                 475                 480

Gln Gly Ser Gln Leu Leu Gly Met Asn Val Trp Ser Lys Glu Lys His
                485                 490                 495

Leu Phe Lys His Lys Gln Gln Val Asn Ala Val Gln Phe Leu Val Gly
            500                 505                 510

Lys Val Thr Ala Asp Gln Ser His Met Gly Ile Val Tyr Ala Gly Tyr
        515                 520                 525

Tyr Ala Val Asp Met Tyr Asp Ala Gln Gly Asn Lys Val Trp Ser Val
    530                 535                 540

Ala Asn Asp Asp Leu Asn Ser Gly Lys Ile Gly Val Ser Ala Tyr Asp
545                 550                 555                 560

Phe Thr Gly Asp Gly Ile Asp Glu Val Leu Val Gln Asp Arg Leu Arg
                565                 570                 575

Met Arg Ile Leu Asp Gly Gln Thr Gly Arg Val Met Gly Ile Ile Ala
            580                 585                 590

Asn Ser Ser Gly Thr Leu Trp Glu Tyr Pro Val Ala Asp Leu Glu
        595                 600                 605

Gly Asn Asn Asn Ala Ser Leu Ile Met Val Ala Asn Asp Tyr Asp Arg
    610                 615                 620

Glu Ser Gln Val Asn His Gly Val Phe Val Tyr Glu Ser Ala Asn Pro
625                 630                 635                 640

Ser Lys Pro Trp Arg Asn Ala Thr Arg Ile Trp Asn Gln Tyr Ala Phe
                645                 650                 655

Asn Phe Ser Asp Ile Asn Ala Asn Gly Thr Ile Pro Thr Asn Ala Gln
            660                 665                 670

Pro Ser Trp Leu Thr His Asn Ser Phe Arg Ser Ala Thr Ile Arg Val
        675                 680                 685

Pro Leu Lys
    690

<210> SEQ ID NO 2
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 2

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
```

```
            20                  25                  30
Asp Cys Glu Leu Gln Pro Val Ile Glu Ala Asn Leu Ser Leu Asn Gln
            35                  40                  45

Asn Gln Leu Ala Ser Asn Gly Gly Tyr Ile Ser Ser Gln Leu Gly Ile
 50                  55                  60

Arg Asn Glu Ser Cys Glu Thr Val Lys Phe Lys Tyr Trp Leu Ser Ile
 65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
            115                 120                 125

Tyr Thr Val Ser Leu Gln Val Val Ala Glu Asn Gly Lys Val Phe Lys
            130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
            195                 200                 205

Pro Asp Gly Leu Ile Ile Pro Val Asn Ala Arg Glu Lys Trp Val Ile
            210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys
            260                 265                 270

<210> SEQ ID NO 3
<211> LENGTH: 957
<212> TYPE: PRT
<213> ORGANISM: Artificial Sequence
<220> FEATURE:
<223> OTHER INFORMATION: Synthetic Polypeptide

<400> SEQUENCE: 3

Met Thr Ser His Tyr Ile Ala Leu Ala Val Gly Leu Leu Ser Leu Ser
 1               5                  10                  15

Ser Asn Val Val Gln Ala Thr Thr Asn Glu Ala Glu Gly Cys Ile Ile
            20                  25                  30

Ser Arg Leu Asn Gly Glu Lys Tyr Cys Leu Lys Val Gly Glu Arg Ser
            35                  40                  45

Gly Tyr Ser Leu Pro Ser Trp Ile Tyr Ala His Pro Val Asp Val Gln
            50                  55                  60

Ala Pro Ser Gly Val Ser Val Met Leu Ser Asp Trp Asp Asn Leu Ser
 65                  70                  75                  80

Tyr Asn Arg Leu Ala Val Phe Asp Arg Tyr Thr Gly Asn Glu Asp Leu
                85                  90                  95

Lys Asn Val Lys Ala Tyr Asn Gly Ala Tyr Leu Asp Phe Ser Lys Pro
            100                 105                 110

Arg Ser Met Arg Val Leu Ala Ser Glu Thr Tyr Pro Glu Ala Cys Ile
```

```
            115                 120                 125
Val Ser Arg Gln Thr Gly Glu Arg Phe Cys Leu Lys Glu Gly Glu Arg
130                 135                 140

Ser Gly Tyr Ser Leu Pro Ala Tyr Ile Tyr Gly His Glu Val Asp Val
145                 150                 155                 160

Glu Ala Pro Leu Gly Leu Gly Val Met Leu Ser Asp Trp Asp Asn Leu
                165                 170                 175

Ser Tyr Asn Arg Leu Ala Val Phe Gly Gly Asn Thr Gln Asn Glu Gln
            180                 185                 190

Met Arg Ala Val Lys Ala Tyr Asn Gly Glu Thr Leu Asp Phe Ser Lys
        195                 200                 205

Pro Arg Ser Met Arg Val Val Pro Tyr Asp Gly Asp Ser Ser Ala Leu
210                 215                 220

Asn Met Lys Leu Lys Trp Ser Trp Gln Gly Ser Ala Phe Gln Pro Asn
225                 230                 235                 240

Ser Asn Gln Val Met Val Thr Pro Ile Val Ala Gln Leu Asn Asp Asp
                245                 250                 255

Asn Gly Asp Gly Lys Ile Asp Glu Lys Asp Val Ala Asp Leu Ile Val
            260                 265                 270

Val Thr Phe Glu Gly Asn Lys Tyr Ala Asn Gly Gly Leu Val Arg Ala
        275                 280                 285

Leu Ser Gly Val Asp Gly Ser Glu Leu Trp Ser Tyr Ala Asn Gly Gly
290                 295                 300

Val Ile Ala Asp Ala Arg Tyr Ser Pro Ala Val Gly Asp Leu Asp Gly
305                 310                 315                 320

Asp Gly Ile Val Glu Ile Val Thr Thr Asn Asn Arg Asp Gln Phe Ile
                325                 330                 335

Thr Ile Leu Asp Asn Gln Gly Asn Ile Lys Lys Gln Ile Pro Thr Thr
            340                 345                 350

Glu Ser Gly Trp Arg Ile Val Gly Asp Ile Thr Leu Ala Asp Leu Asp
        355                 360                 365

His Asp Gly Ser Val Glu Ile Leu Ala Ala Asp Gly Val Tyr Asn Tyr
370                 375                 380

His Ser Gly Leu Val Phe Asn His Pro Trp Ala Pro Ser Ser Ile Asn
385                 390                 395                 400

Val Asp Val Asp Gly Asp Gln Gln Gln Glu Val Phe Ser Gly Gly Thr
                405                 410                 415

Leu Phe Gln Asn Asn Gly Ala Ile Asn Trp Gln Tyr Gln Ala Asn Asp
            420                 425                 430

Ala Val Trp Phe Ser Ser Leu Val Asn Leu Asp Asn Asp Ala Glu Pro
        435                 440                 445

Glu Ile Val Ala Ser Val Pro Ala Thr Phe Ala Thr Gly Asp Asn Ala
450                 455                 460

Arg Phe Ala Val Leu Glu His Asp Gly Thr Ile Lys Trp Glu Ile Asn
465                 470                 475                 480

Asn Thr Ala Asn Pro Gly Gly Val Gln Ala Val Ser Asn Phe Leu
                485                 490                 495

Gly Lys Ala Gln Ala Val Glu Thr Ser Glu Phe Ser Val Tyr Gly
            500                 505                 510

Tyr Gln Pro Asn Asn Pro Ala Ser Ile Ala Leu Ala Val Asp Gly
        515                 520                 525

Lys Ile Ser Val Arg Ser Gly Phe Ala Ile Asp Ala Ile Gly Ala Ser
530                 535                 540
```

```
Ala Ser Thr Leu Val Gly Gly Thr Gly Gly Asn Leu Asn Ala Ala Val
545                 550                 555                 560

Asn Val Lys Asp Ile Lys Ala Ile Asp Leu Thr Trp Gly Lys Tyr Tyr
            565                 570                 575

Trp Gly Gly Tyr His Leu Leu Ala Leu Asp Phe Arg Met Ser Asn Gly
        580                 585                 590

Ser Val Ile Ser Met Gly Ser Lys Asn Tyr Ala Tyr Ser Lys Gln Thr
            595                 600                 605

Glu Arg Phe Thr Val Pro Ala Gly Ser Arg Ile Lys Gly Ile Lys Ala
        610                 615                 620

Trp Thr Ala Gly Trp Leu Leu Asp Gly Val Gln Phe Glu Leu Ala Thr
625                 630                 635                 640

Gln Asn Gly Thr Asn Asp Leu Asp Val Lys Gly Ile Val Tyr Ala Gly
                645                 650                 655

Tyr Ala Ala Val Asp Met Tyr Asn Ser Lys Gly Glu Arg Val Trp Ser
            660                 665                 670

Val Ala Asn Asp Asp Thr Gly Ser Gly Lys Ile Gly Val Ser Ala Tyr
            675                 680                 685

Asp Phe Asp Asn Asp Gly Ile Asp Glu Val Leu Val Gln Asp His Ala
        690                 695                 700

Arg Val Arg Val Leu Asp Gly Lys Thr Gly Lys Glu Arg Ala Ser Leu
705                 710                 715                 720

Ala His Ser Thr Ala Thr Leu Trp Glu Tyr Pro Ile Val Val Asp Leu
                725                 730                 735

Glu Gly Asp Asn Asn Ala Glu Leu Ile Val Ala Ala Asn Asp Phe Asp
            740                 745                 750

Arg Gln Tyr Ser Ile Asn His Gly Val Tyr Val Tyr Gln Ser Ala Asp
            755                 760                 765

Ser Ser Lys Pro Trp Lys Asn Ala Thr Arg Ile Trp Asn Gln His Ala
            770                 775                 780

Phe His Leu Thr Asn Ile Asn Gln Asp Gly Thr Leu Pro Thr Phe Val
785                 790                 795                 800

Glu Pro Ser Trp Leu Ser His Asn Thr Tyr Arg Ser Ser Thr Leu Arg
                805                 810                 815

Ala Ala Val Gly Gly Glu Ser Pro Ile Phe Gly Tyr Ser Asn Thr Gln
                820                 825                 830

Gln Ser Gln Arg Val Val Thr Ala Asp Asn Leu Met Tyr Leu Arg Ser
            835                 840                 845

Gly Phe Ala Ile Asp Ala Ile Gly Thr Thr Val Asn Asn Leu Val Gly
            850                 855                 860

Gly Pro Val Gln Gly Thr Asn Gly Gly Val Leu Arg Ala Pro Ile Ala
865                 870                 875                 880

Leu Asp Gln Leu Gln Ser Val Glu Val Thr Ser Gly Leu Tyr Asn Trp
                885                 890                 895

Gly Gly Tyr His Ile Val Ala Ile Lys Phe Thr Met Lys Asp Gly Ser
            900                 905                 910

Ser Val Leu Leu Gly Ser Thr His Tyr Ala Ser Asn Lys Lys Val Glu
            915                 920                 925

Thr Tyr Thr Val Pro Gln Gly Lys Arg Ile Lys Gln Ile Asn Val Trp
            930                 935                 940

Thr Gly Gly Trp Leu Val Glu Gly Phe Gln Phe Val Tyr
945                 950                 955
```

```
<210> SEQ ID NO 4
<211> LENGTH: 741
<212> TYPE: PRT
<213> ORGANISM: Artificial Sequence
<220> FEATURE:
<223> OTHER INFORMATION: Synthetic Polypeptide

<400> SEQUENCE: 4
```

| Met | Pro | Lys | Leu | Asn | Arg | Cys | Ala | Ile | Ala | Ile | Phe | Thr | Ile | Leu | Ser |
|---|---|---|---|---|---|---|---|---|---|---|---|---|---|---|---|
| 1 | | | | 5 | | | | | 10 | | | | | 15 | |

Ala Ile Ser Ser Pro Thr Leu Leu Ala Asn Ile Asn Glu Pro Ser Gly
            20                  25                  30

Glu Ala Ala Asp Ile Ile Ser Gln Val Ala Asp Ser His Ala Ile Lys
        35                  40                  45

Tyr Tyr Asn Ala Ala Asp Trp Gln Ala Glu Asp Asn Ala Leu Pro Ser
    50                  55                  60

Leu Ala Glu Leu Arg Asp Leu Val Ile Asn Gln Gln Lys Arg Val Leu
65                  70                  75                  80

Val Asp Phe Ser Gln Ile Ser Asp Ala Glu Gly Gln Ala Glu Met Gln
                85                  90                  95

Ala Gln Phe Arg Lys Ala Tyr Gly Val Gly Phe Ala Asn Gln Phe Ile
            100                 105                 110

Val Ile Thr Glu His Lys Gly Glu Leu Leu Phe Thr Pro Phe Asp Gln
        115                 120                 125

Ala Glu Glu Val Asp Pro Gln Leu Leu Glu Ala Pro Arg Thr Ala Arg
    130                 135                 140

Leu Leu Ala Arg Ser Gly Phe Ala Ser Pro Ala Pro Ala Asn Ser Glu
145                 150                 155                 160

Thr Asn Thr Leu Pro His Val Ala Phe Tyr Ile Ser Val Asn Arg Ala
                165                 170                 175

Ile Ser Asp Glu Glu Cys Thr Phe Asn Asn Ser Trp Leu Trp Lys Asn
            180                 185                 190

Glu Lys Gly Ser Arg Pro Phe Cys Lys Asp Ala Asn Ile Ser Leu Ile
        195                 200                 205

Tyr Arg Val Asn Leu Glu Arg Ser Leu Gln Tyr Gly Ile Val Gly Ser
    210                 215                 220

Ala Thr Pro Asp Ala Lys Ile Val Arg Ile Ser Leu Asp Asp Ser
225                 230                 235                 240

Thr Gly Ala Gly Ile His Leu Asn Asp Gln Leu Gly Tyr Arg Gln Phe
                245                 250                 255

Gly Ala Ser Tyr Thr Thr Leu Asp Ala Tyr Phe Arg Glu Trp Ser Thr
            260                 265                 270

Asp Ala Ile Ala Gln Asp Tyr Arg Phe Val Phe Asn Ala Ser Asn Asn
        275                 280                 285

Lys Ala Gln Ile Leu Lys Thr Phe Pro Val Asp Asn Ile Asn Glu Lys
    290                 295                 300

Phe Glu Arg Lys Glu Val Ser Gly Phe Glu Leu Gly Val Thr Gly Gly
305                 310                 315                 320

Val Glu Val Ser Gly Asp Gly Pro Lys Ala Lys Leu Glu Ala Arg Ala
                325                 330                 335

Ser Tyr Thr Gln Ser Arg Trp Leu Thr Tyr Asn Thr Gln Asp Tyr Arg
            340                 345                 350

Ile Glu Arg Asn Ala Lys Asn Ala Gln Ala Val Ser Phe Thr Trp Asn
        355                 360                 365

```
Arg Gln Gln Tyr Ala Thr Ala Glu Ser Leu Leu Asn Arg Ser Thr Asp
370                 375                 380

Ala Leu Trp Val Asn Thr Tyr Pro Val Asp Val Asn Arg Ile Ser Pro
385                 390                 395                 400

Leu Ser Tyr Ala Ser Phe Val Pro Lys Met Asp Val Ile Tyr Lys Ala
                405                 410                 415

Ser Ala Thr Glu Thr Gly Ser Thr Asp Phe Ile Ile Asp Ser Ser Val
            420                 425                 430

Asn Ile Arg Pro Ile Tyr Asn Gly Ala Tyr Lys His Tyr Tyr Val Val
        435                 440                 445

Gly Ala His Gln Phe Tyr His Gly Phe Glu Asp Thr Pro Arg Arg Arg
450                 455                 460

Ile Thr Lys Ser Ala Ser Phe Thr Val Asp Trp Asp His Pro Val Phe
465                 470                 475                 480

Thr Gly Gly Arg Pro Val Asn Leu Gln Leu Ala Ser Phe Asn Asn Arg
                485                 490                 495

Cys Ile Gln Val Asp Ala Gln Gly Arg Leu Ala Ala Asn Thr Cys Asp
                500                 505                 510

Ser Gln Gln Ser Ala Gln Ser Phe Ile Tyr Asp Gln Leu Gly Arg Tyr
            515                 520                 525

Val Ser Ala Ser Asn Thr Lys Leu Cys Leu Asp Gly Glu Ala Leu Asp
530                 535                 540

Ala Leu Gln Pro Cys Asn Gln Asn Leu Thr Gln Arg Trp Glu Trp Arg
545                 550                 555                 560

Lys Gly Thr Asp Glu Leu Thr Asn Val Tyr Ser Gly Glu Ser Leu Gly
                565                 570                 575

His Asp Lys Gln Thr Gly Glu Leu Gly Leu Tyr Ala Ser Ser Asn Asp
            580                 585                 590

Ala Val Ser Leu Arg Thr Ile Thr Ala Tyr Thr Asp Val Phe Asn Ala
        595                 600                 605

Gln Glu Ser Ser Pro Ile Leu Gly Tyr Thr Gln Gly Lys Met Asn Gln
610                 615                 620

Gln Arg Val Gly Gln Asp His Arg Leu Tyr Val Arg Ala Gly Ala Ala
625                 630                 635                 640

Ile Asp Ala Leu Gly Ser Ala Ser Asp Leu Leu Val Gly Gly Asn Gly
                645                 650                 655

Gly Ser Leu Ser Ser Val Asp Leu Ser Gly Val Lys Ser Ile Thr Ala
            660                 665                 670

Thr Ser Gly Asp Phe Gln Tyr Gly Gly Gln Gln Leu Val Ala Leu Thr
        675                 680                 685

Phe Thr Tyr Gln Asp Gly Arg Gln Gln Thr Val Gly Ser Lys Ala Tyr
690                 695                 700

Val Thr Asn Ala His Glu Asp Arg Phe Asp Leu Pro Ala Ala Ala Lys
705                 710                 715                 720

Ile Thr Gln Leu Lys Ile Trp Ser Asp Asp Trp Leu Val Lys Gly Val
                725                 730                 735

Gln Phe Asp Leu Asn
            740

<210> SEQ ID NO 5
<211> LENGTH: 124
<212> TYPE: PRT
<213> ORGANISM: Artificial Sequence
<220> FEATURE:
<223> OTHER INFORMATION: Synthetic Polypeptide
```

<400> SEQUENCE: 5

```
Met Ile Lys Leu Lys Phe Gly Val Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120
```

<210> SEQ ID NO 6
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 6

```
Met Asn Ile Phe Lys Gln Thr Cys Val Gly Ala Phe Ala Val Ile Phe
1               5                   10                  15

Gly Ala Thr Ser Ile Ala Pro Thr Met Ala
            20                  25
```

<210> SEQ ID NO 7
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 7

```
Met Lys Phe Leu Gln Gln Met Arg Lys Leu Phe Gly Leu Ala Ala Lys
1               5                   10                  15

Phe Pro Ala Arg Leu Thr Ile Ala Val Ile Gly Thr Ala Leu Leu Ala
            20                  25                  30

Gly Leu Val Gly Val Val Gly Asp Thr Ala Ile Ala Val Ala
        35                  40                  45
```

<210> SEQ ID NO 8
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 8

```
Met Asn Pro Met Thr Arg Arg His Thr Trp Thr Arg Leu Ala Cys Ala
1               5                   10                  15

Leu Ser Leu Gly Val Ala Ala Phe Ala Ala Gln Ala
            20                  25
```

```
<210> SEQ ID NO 9
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 9

Met Ser Thr Phe Lys Leu Leu Lys Thr Leu Thr Ser Arg Arg Gln Val
1               5                   10                  15

Leu Lys Thr Gly Leu Ala Ala Leu Thr Leu Ser Gly Met Ser His Ala
            20                  25                  30

Val Ala

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Met Lys Leu Ala Ala Cys Phe Leu Thr Leu Leu Pro Gly Phe Ala Val
1               5                   10                  15

Ala

<210> SEQ ID NO 11
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 11

Met His Pro Ser Thr Ser Arg Pro Ser Arg Arg Thr Leu Leu Thr Ala
1               5                   10                  15

Thr Ala Gly Ala Ala Leu Ala Ala Ala Thr Leu Val Pro Gly Thr Ala
            20                  25                  30

His Ala Ser Ser Gly Gly Arg
        35

<210> SEQ ID NO 12
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 12

Met Arg Phe Arg His Lys Ala Ala Ala Leu Ala Ala Thr Leu Ala Leu
1               5                   10                  15

Pro Leu Ala Gly Leu Val Gly Leu Ala Ser Pro Ala Gln Ala
            20                  25                  30

<210> SEQ ID NO 13
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 13

Ile Leu Pro Trp Lys Trp Pro Trp Trp Pro Trp Arg Arg
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 14

Val Phe Leu Arg Arg Ile Arg Val Ile Val Ile Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 15

Val Phe Trp Arg Arg Ile Arg Val Trp Val Ile Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 16

Val Gln Leu Arg Ala Ile Arg Val Arg Val Ile Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Val Gln Leu Arg Arg Ile Arg Val Trp Val Ile Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 18

Val Gln Trp Arg Ala Ile Arg Val Arg Val Ile Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 19

Val Gln Trp Arg Arg Ile Arg Val Trp Val Ile Arg
1               5                   10
```

```
<210> SEQ ID NO 20
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 20

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 21

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 22
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 22

Arg Leu Ala Arg Ile Val Val Ile Arg Val Ala Arg Leu Leu Gly Asp
1               5                   10                  15

Phe Phe Arg Lys Ser Lys Glu Lys Ile Gly Lys Glu Phe Lys Arg Ile
            20                  25                  30

Val Gln Arg Ile Lys Asp Phe Leu Arg Asn Leu Val Pro Arg Thr Glu
        35                  40                  45

Ser

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

Val Gln Leu Arg Ile Arg Val Ala Val Ile Arg Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Val Gln Arg Trp Leu Ile Val Trp Arg Ile Arg Lys
1               5                   10
```

```
<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 25

Val Arg Leu Ile Val Ala Val Arg Ile Trp Arg Arg
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 26

Ile Trp Val Ile Trp Arg Arg
1               5

<210> SEQ ID NO 27
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is dehydrobutyrine
<220> FEATURE:
<221> NAME/KEY: misc_feature
<222> LOCATION: (5)..(5)
<223> OTHER INFORMATION: Xaa is dehydroalanine
<220> FEATURE:
<221> NAME/KEY: misc_feature
<222> LOCATION: (8)..(8)
<223> OTHER INFORMATION: Xaa is 2-aminobutyric acid
<220> FEATURE:
<221> NAME/KEY: misc_feature
<222> LOCATION: (13)..(13)
<223> OTHER INFORMATION: Xaa is 2-aminobutyric acid
<220> FEATURE:
<221> NAME/KEY: misc_feature
<222> LOCATION: (23)..(23)
<223> OTHER INFORMATION: Xaa is 2-aminobutyric acid
<220> FEATURE:
<221> NAME/KEY: misc_feature
<222> LOCATION: (25)..(25)
<223> OTHER INFORMATION: Xaa is 2-aminobutyric acid
<220> FEATURE:
<221> NAME/KEY: misc_feature
<222> LOCATION: (33)..(33)
<223> OTHER INFORMATION: Xaa is dehydroalanine

<400> SEQUENCE: 27

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile Asn Val
            20                  25                  30

Xaa Leu

<210> SEQ ID NO 28
<211> LENGTH: 12
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 28

Val Xaa Xaa Arg Xaa Ile Arg Val Xaa Val Ile Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 29

Ile Leu Lys Trp Lys Trp Pro Trp Trp Pro Trp Arg Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 30

Ile Leu Pro Trp Lys Lys Pro Trp Trp Pro Trp Arg Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 31

Ile Leu Lys Trp Lys Trp Pro Trp Trp Lys Trp Arg Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 32

Ile Leu Arg Trp Lys Trp Arg Trp Trp Arg Trp Arg Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

<222> LOCATION: (1)..(1)
<223> OTHER INFORMATION: Xaa is RbmA-CtxB-I-

<400> SEQUENCE: 33

Xaa Leu Pro Trp Lys Trp Pro Trp Trp Pro Trp Arg Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is RbmC-I-

<400> SEQUENCE: 34

Xaa Leu Lys Trp Lys Trp Pro Trp Trp Pro Trp Arg Arg
1 5 10

<210> SEQ ID NO 35
<211> LENGTH: 279
<212> TYPE: PRT
<213> ORGANISM: Artificial Sequence
<220> FEATURE:
<223> OTHER INFORMATION: Synthetic Polypeptide

<400> SEQUENCE: 35

Met Ser Asn Phe Lys Gly Ser Ile Met Asn Lys Arg His Tyr Tyr Leu
1 5 10 15

Ala Ser Cys Leu Ala Leu Leu Phe Ser Thr Ala Ser Tyr Ala Glu Val
20 25 30

Asp Cys Glu Leu Gln Pro Val Ile Glu Ala Asn Leu Ser Leu Asn Gln
35 40 45

Asn Gln Leu Ala Ser Asn Gly Gly Tyr Ile Ser Ser Gln Leu Gly Ile
50 55 60

Arg Asn Glu Ser Cys Glu Thr Val Lys Phe Lys Tyr Trp Leu Ser Ile
65 70 75 80

Lys Gly Pro Glu Gly Ile Tyr Phe Pro Ala Lys Ala Val Val Gly Val
85 90 95

Asp Thr Ala Gln Gln Glu Ser Asp Ala Leu Thr Asp Gly Arg Met Leu
100 105 110

Asn Val Thr Arg Gly Phe Trp Val Pro Glu Tyr Met Ala Asp Gly Lys
115 120 125

Tyr Thr Val Ser Leu Gln Val Val Ala Glu Asn Gly Lys Val Phe Lys
130 135 140

Ala Asn Gln Glu Phe Val Lys Gly Val Asp Leu Asn Ser Leu Pro Glu
145 150 155 160

Leu Asn Gly Leu Thr Ile Asp Ile Lys Asn Gln Phe Gly Ile Asn Ser
165 170 175

Val Glu Ser Thr Gly Gly Phe Val Pro Phe Thr Val Asp Leu Asn Asn
180 185 190

Gly Arg Glu Gly Glu Ala Asn Val Glu Phe Trp Met Thr Ala Val Gly
195 200 205

Pro Asp Gly Leu Ile Ile Pro Val Asn Ala Arg Glu Lys Trp Val Ile
210 215 220

Ala Ser Gly Asp Thr Tyr Ser Lys Val Arg Gly Ile Asn Phe Asp Lys
225 230 235 240

Ser Tyr Pro Ala Gly Glu Tyr Thr Ile Asn Ala Gln Val Val Asp Ile

```
            245                 250                 255
Val Ser Gly Glu Arg Val Glu Gln Ser Met Thr Val Val Lys Lys Asp
            260                 265                 270

Tyr Lys Asp Asp Asp Lys
            275

<210> SEQ ID NO 36
<211> LENGTH: 395
<212> TYPE: PRT
<213> ORGANISM: Artificial Sequence
<220> FEATURE:
<223> OTHER INFORMATION: Synthetic Polypeptide

<400> SEQUENCE: 36

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
        35                  40                  45

Asn Gln Leu Ala Ser Asn Gly Gly Tyr Ile Ser Ser Gln Leu Gly Ile
    50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
    130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys Met
            260                 265                 270

Ile Lys Leu Lys Phe Gly Val Phe Phe Thr Val Leu Leu Ser Ser Ala
        275                 280                 285

Tyr Ala His Gly Thr Pro Gln Asn Ile Thr Asp Leu Cys Ala Glu Tyr
    290                 295                 300

His Asn Thr Gln Ile Tyr Thr Leu Asn Asp Lys Ile Phe Ser Tyr Thr
305                 310                 315                 320

Glu Ser Leu Ala Gly Lys Arg Glu Met Ala Ile Ile Thr Phe Lys Asn
                325                 330                 335
```

```
Gly Ala Ile Phe Gln Val Glu Val Pro Gly Ser Gln His Ile Asp Ser
                340                 345                 350

Gln Lys Lys Ala Ile Glu Arg Met Lys Asp Thr Leu Arg Ile Ala Tyr
            355                 360                 365

Leu Thr Glu Ala Lys Val Glu Lys Leu Cys Val Trp Asn Asn Lys Thr
370                 375                 380

Pro His Ala Ile Ala Ala Ile Ser Met Ala Asn
385                 390                 395

<210> SEQ ID NO 37
<211> LENGTH: 1128
<212> TYPE: PRT
<213> ORGANISM: Artificial Sequence
<220> FEATURE:
<223> OTHER INFORMATION: Synthetic Polypeptide

<400> SEQUENCE: 37

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
                20                  25                  30

Asp Cys Glu Leu Gln Pro Val Ile Glu Ala Asn Leu Ser Leu Asn Gln
            35                  40                  45

Asn Gln Leu Ala Ser Asn Gly Gly Tyr Ile Ser Ser Gln Leu Gly Ile
        50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
    130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys Met
            260                 265                 270

Asn Arg Met Thr Leu Cys Ala Ala Ser Ile Ala Cys Ala Leu Ala Ser
        275                 280                 285

Thr Ala Met Ala Ala Pro Ser Ala Pro Ser Val Asp Val Tyr Gly Ser
    290                 295                 300
```

```
Asn Asn Leu Gln Phe Ser Lys Ile Glu Leu Ala Met Glu Thr Thr Ala
305                 310                 315                 320

Gly Tyr Asn Gln Met Val Lys Tyr His Glu Ala Pro Ile Thr Leu
            325                 330                 335

Lys Phe Asn Gln Trp Ser Gly Val Thr Gly Asn Thr Tyr Lys Ile Tyr
                340                 345                 350

Phe Asp Gly Val Glu Val Ala Thr Gly Pro Ile Ser Gly Ser Gln Thr
            355                 360                 365

Thr Ala Gln Phe Thr Tyr Pro Lys Gly Val Tyr Gln Leu Val Ile
370                 375                 380

Glu Ala Cys Asp Ala Thr Gly Cys Thr Lys Ser Ala Pro Ser Glu Ile
385                 390                 395                 400

Thr Ile Ala Asp Thr Asp Gly Ser His Leu Lys Pro Leu Lys Met Asn
                405                 410                 415

Val Asp Pro Asn Asn Lys Ser Tyr Thr Ile Pro Gln Asn Thr Val Ile
            420                 425                 430

Gly Thr Tyr Phe Val Glu Trp Ser Ile Tyr Asp Arg Lys Phe Thr Val
                435                 440                 445

Asp Asn Ile Pro Gly Gln Asn Leu Thr His Ile Leu Tyr Gly Phe Ile
450                 455                 460

Pro Ile Cys Gly Pro Asn Glu Ser Leu Lys Ser Val Gly Gly Asn Ser
465                 470                 475                 480

Phe Asn Ala Leu Gln Thr Ala Cys Lys Gly Val Pro Asp Phe Glu Val
                485                 490                 495

Val Ile His Asp Pro Trp Ala Ala Tyr Gln Lys Ser Phe Pro Gln Ala
                500                 505                 510

Gly His Gln Tyr Ser Ser Pro Ile Lys Gly Asn Tyr Ala Met Leu Met
                515                 520                 525

Ala Leu Lys Lys Thr Tyr Pro Asp Leu Lys Ile Ile Pro Ser Ile Gly
530                 535                 540

Gly Trp Thr Leu Ser Asp Pro Phe Phe Ser Phe Thr Asp Lys Ala Lys
545                 550                 555                 560

Arg Asp Val Phe Val Ala Ser Val Lys Arg Phe Leu Lys Thr Trp Lys
                565                 570                 575

Phe Tyr Asp Gly Val Asp Ile Asp Trp Glu Tyr Pro Gly Gly Gly Gly
                580                 585                 590

Gln Ala Ala Asp Leu Gly Asp Pro Val Lys Asp Gly Pro Ala Tyr Val
                595                 600                 605

Ala Leu Met Ala Glu Leu Arg Ala Met Leu Asp Glu Leu Glu Ala Glu
                610                 615                 620

Thr Gly Arg Lys Tyr Glu Leu Thr Ser Ala Ile Gly Val Gly His Asp
625                 630                 635                 640

Lys Ile Glu Asp Val Asn Tyr Gly Gln Ala Val Gln Tyr Met Asp Tyr
                645                 650                 655

Ile Phe Ala Met Thr Tyr Asp Phe Tyr Gly Gly Trp Asn Asn Val Leu
                660                 665                 670

Gly His Gln Thr Ala Leu Tyr Cys Gly Ser Phe Met Arg Pro Gly Gln
                675                 680                 685

Cys Asp Gly Lys Gly Val Asp Glu Asn Gly Glu Pro Tyr Lys Gly Pro
            690                 695                 700

Ala Tyr Thr Thr Asp Asn Gly Ile Gln Leu Leu Leu Ala Gln Gly Val
705                 710                 715                 720
```

-continued

```
Pro Pro Ser Lys Leu Val Val Gly Ala Ala Met Tyr Gly Arg Gly Trp
            725                 730                 735
Glu Gly Val Thr Pro Ala Ser Leu Lys Asp Pro Asn Asp Pro Met Thr
        740                 745                 750
Gly Val Gly Asn Gly Lys Leu Lys Gly Thr Thr Ala Gln Gly Val Trp
    755                 760                 765
Glu Ala Gly Val Ile Asp Tyr Lys Gly Val Lys Asn Phe Met Leu Gly
770                 775                 780
Ala Asn Lys Thr Gly Val Asn Gly Phe Glu Tyr Gly Tyr Asp Glu Gln
785                 790                 795                 800
Ala Glu Ala Pro Trp Val Trp Asn Arg Thr Thr Gly Gln Leu Val Thr
            805                 810                 815
Phe Asp Asp Arg Ser Val Lys Ala Lys Gly Ala Tyr Val Arg Asn
            820                 825                 830
Leu Gly Leu Ala Gly Leu Phe Ser Trp Glu Ile Asp Ala Asp Asn Gly
            835                 840                 845
Asp Ile Leu Asn Ala Met His Glu Gly Leu Ala Gly Gly Thr Thr Thr
            850                 855                 860
Pro Pro Val Asn Lys Ala Pro Val Ala Asn Ala Gly Ala Asp Ile Thr
865                 870                 875                 880
Val Thr Gly Pro Ala Ala Val Ser Leu Asp Gly Ser Ala Ser Lys Asp
                885                 890                 895
Ser Asp Gly Ser Ile Ala Ser Tyr Leu Trp Glu Gln Thr Ala Gly Pro
            900                 905                 910
Ala Val Thr Leu Thr Gly Ala Asn Ser Ala Lys Ala Ser Phe Asn Ala
            915                 920                 925
Ala Glu Val Thr Glu Lys Gln Thr Phe Thr Phe Lys Leu Thr Val Thr
            930                 935                 940
Asp Asn Lys Gly Ala Thr Ala Thr Asp Thr Val Val Val Thr Val Asn
945                 950                 955                 960
Pro Lys Ser Thr Thr Pro Val Asn Thr Ala Pro Val Ala Ala Leu Ser
                965                 970                 975
Ala Pro Ala Ser Val Lys Ala Gly Ala Thr Val Val Asp Ala Ser
            980                 985                 990
Ala Ser Ser Asp Ala Asp Gln Asp Pro Leu Ser Phe Thr Trp Asp Leu
            995                1000                1005
Pro Val Gly Val Asn Ala Thr Val Gln Gly Ala Lys Val Thr Phe
    1010                1015                1020
Val Ala Gly Glu Tyr Thr Gln Asp Thr Thr Leu Asp Phe Thr Val
    1025                1030                1035
Thr Val Ser Asp Gly Lys Ala Thr Ser Lys Ala Ser Ala Ser Val
    1040                1045                1050
Leu Val Glu Lys Lys Ala Gly Thr Gly Gly Asp Ala Cys Thr Asn
    1055                1060                1065
Leu Trp Asn Ala Glu Ser Ile Tyr Thr Gly Gly Gln Gln Val Thr
    1070                1075                1080
Trp Ala Gly Lys Thr Trp Glu Ala Lys Trp Trp Thr Arg Gly Glu
    1085                1090                1095
Asp Pro Ser Lys Ser Gly Gln Trp Gly Val Trp Lys Asp Leu Gly
    1100                1105                1110
Ala Ala Ser Cys Ser Thr His Asp Tyr Leu Asp Asp Asp Lys
    1115                1120                1125
```